United States Patent [19]

Sprecker et al.

[11] Patent Number: 4,963,285
[45] Date of Patent: Oct. 16, 1990

[54] 2,4,4-TRISUBSTITUTED TETRAHYDRO PYRANYL ESTERS AND ORGANOLEPTIC USES THEREOF

[75] Inventors: Mark A. Sprecker, Sea Bright; Roger E. Greene, Oakhurst, both of N.J.

[73] Assignee: International Flavors & Fragrances Inc., New York, N.Y.

[21] Appl. No.: 308,182

[22] Filed: Feb. 9, 1989

[51] Int. Cl.$^5$ .................. C07D 69/068; C11D 3/50; C11D 3/395
[52] U.S. Cl. .................. 252/174.11; 252/89.1; 252/187.25; 252/187.26; 512/11; 549/356; 560/126
[58] Field of Search ............. 252/174.11, 89.1, 187.25, 252/187.26

[56] References Cited

U.S. PATENT DOCUMENTS 4,390,448  6/1983  Boden et al. .................. 252/187.26

FOREIGN PATENT DOCUMENTS 284969  10/1988  France .
4747389  12/1970  Japan .
0618374   8/1978  U.S.S.R. .
0620487   8/1978  U.S.S.R. .
0638597  12/1978  U.S.S.R. .

OTHER PUBLICATIONS

Arctander, *Perfume & Flavor Chemicals (Aroma Chemicals) II*, 1969, (Montclair, NJ), Monographs 1935 & 2926.

*Primary Examiner*—Paul Lieberman
*Assistant Examiner*—A. Beadles-Hay
*Attorney, Agent, or Firm*—Arthur L. Liberman

[57] ABSTRACT

Described are 2,4,4-trisubstituted tetrahydro pyranyl esters defined according to the structure:

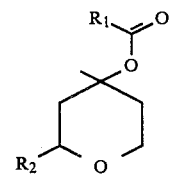

wherein $R_1$ represents methyl or ethyl and $R_2$ represents $C_2$-$C_4$ straight chain or branched chain alkyl or alkenyl and organoleptic used thereof in augmenting or enhancing the aroma of perfume compositions, colognes and perfumed articles including, but not limited to bleach compositions, solid or liquid anionic, cationic, nonionic or zwitterionic detergents, perfumed polymers, fabric softener compositions, fabric softener articles, cosmetic powders and hair preparations.

32 Claims, 26 Drawing Sheets

GLC PROFILE FOR EXAMPLE I.

FIG. 2 NMR SPECTRUM FOR EXAMPLE I.

GLC PROFILE FOR EXAMPLE II.

NMR SPECTRUM FOR EXAMPLE II.

GLC PROFILE FOR EXAMPLE III.

FIG. 6 NMR SPECTRUM FOR EXAMPLE III.

GLC PROFILE FOR EXAMPLE IV

FIG. 8 NMR SPECTRUM FOR EXAMPLE IV.

GLC PROFILE FOR EXAMPLE V.

NMR SPECTRUM FOR EXAMPLE V.

GLC PROFILE FOR EXAMPLE VI.

GLC PROFILE FOR EXAMPLE VII.

GLC PROFILE FOR EXAMPLE VIII.

FIG.15 NMR SPECTRUM FOR EXAMPLE VIII

GLC PROFILE FOR EXAMPLE IX.

FIG. 17 NMR SPECTRUM FOR EXAMPLE IX.

GLC PROFILE FOR EXAMPLE X.

FIG. 19 NMR SPECTRUM FOR EXAMPLE X.

GLC PROFILE FOR EXAMPLE XI.

FIG. 21 NMR SPECTRUM FOR EXAMPLE XI.

GLC PROFILE FOR EXAMPLE XII.

NMR SPECTRUM FOR EXAMPLE XII

GLC PROFILE FOR EXAMPLE XIII.

FIG. 25 NMR SPECTRUM FOR EXAMPLE XIII.

2,4,4-TRISUBSTITUTED TETRAHYDRO PYRANYL ESTERS AND ORGANOLEPTIC USES THEREOF

BACKGROUND OF THE INVENTION

The present invention relates to 2,4,4-trisubstituted tetrahydro pyranyl esters defined according to the structure:

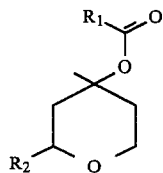

wherein $R_1$ represents methyl or ethyl and $R_2$ represents $C_2$-$C_4$ straight chain or branched chain alkyl or alkenyl and uses thereof in order to alter, modify or enhance the aroma of consumable materials.

There has been considerable work performed relating to substances which can be used to impart (modify, augment or enhance) fragrances to (or in) various consumable materials. These substances are used to diminish the use of natural materials, some of which may be in short supply and to provide more uniform properties in the finished product.

A fruity, citrusy, grapefruit, green, herbaceous, chamomile, floral, lily, rose, muguet, live flower petal-like, sauge sclaree, tobacco, mentha citrata, lavender, witch hazel, woody, orris, earthy, early morning forest path, oolong tea, ozoney, natural waxey, piney, guiacwood-like, sweet, jasmine and geranium aromas with chamomile, woody, soft woody, cabreuva, sauge sclaree, lavender, winey, floral, rose, copaiba oil-like, geranium, earthy, early morning forest path, fatty, oatmeal, herbaceous, spicy and black pepper undertones are highly desirable in several types of perfume compositions, perfumed articles and colognes.

The perfume use of 2,4,4-trisubstituted tetrahydro pyranols having the structures:

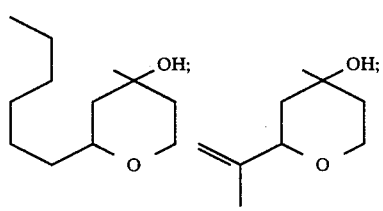

and

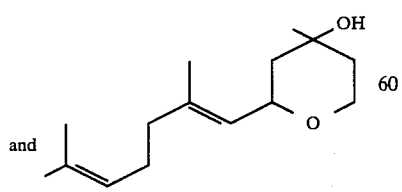

is disclosed in the literature as follows:

(a) the perfume use of the compound having the structure:

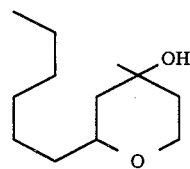

USSR Pat. No. 620487 of July 17, 1978 (Chemical Abstracts 89:185929p);

(b) the compound having the structure:

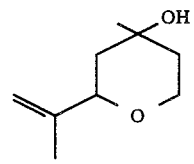

USSR Pat. No. 638597 of Dec. 28, 1978 (Chemical Abstracts, Volume 90:109812a);

(c) the compound having the structure:

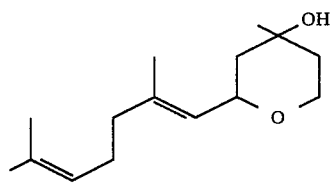

USSR Pat. No. 618374 of Aug. 5, 1978 (Chemical Abstracts 89:179861u);
tetrahydro pyranyl esters are also known for their use in perfumery, specifically:

(a) the compound having the structure:

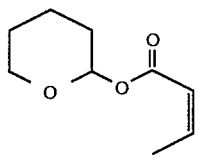

disclosed by Arctander "Perfume And Flavor Chemicals (Aroma Chemicals)", Volumes I and II, at Monograph 2926 as follows:

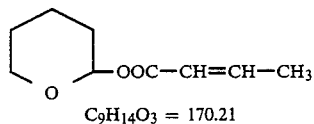

$C_9H_{14}O_3 = 170.21$ (b) the compound having the structure:

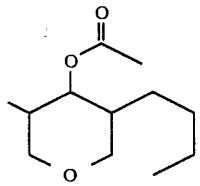

disclosed by Arctander, at Monograph 1935, to wit:

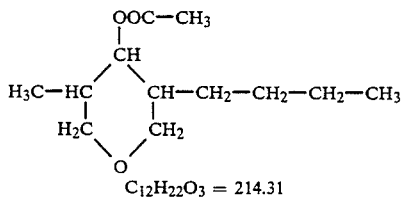

$C_{12}H_{22}O_3 = 214.31$

The 2,4,4-trisubstituted tetrahydro pyranyl esters of our invention are novel compounds and have unexpected, unobvious and advantageous organoleptic properties with respect to the organoleptic properties of the compounds of the prior art.

Furthermore, considerable difficulties have heretofore been encountered in using compounded hypochlorite bleach orsterilizigsolutions with perfumed oils so that a stable long-lasting, single phase commercially feasible bleach or sterilizing solution has been difficult to obtain, particularly wherein the desired aroma of the article bleached or sterilized (e.g., clothing) has a pleasant and stable and consistent aroma on drying (and not the usual "hypochlorite-bleached-article" aroma). The problem has been defined in United Kingdom Patent Specification No. 886,084 published on Jan. 3, 1962 wherein it is stated that a stable "dispersion" of hypochorite-resistent perfume in aqueous solutions of hypochlorites was formulated. United Kingdom Patent Specification No. 886,084 discloses the preparation of an aqueous "solution" of a hypochlorite containing a hypochlorite resistant perfume and a surface active quaternary ammonium compound of the betaine type soluble in the hypochlorite solution. Such ammonium compounds have the generic structure:

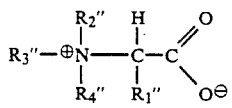

wherein each of $R_1''$, $R_2''$, $R_3''$ and $R_4''$ are alkyl. One of the features of the perfumed solutions produced in accordance with said United Kingdom Patent Specification No. 886,084 is indicated to be that the solution exhibits foaming properties. Another feature of United Kingdom Patent Specification No. 886,084 is stated to be that the perfumed solutions covered by the patent are found to be clear and homogeneous after eight weeks of storage at room temperature. Nevertheless, betaines such as "Ambiteric D" as are discussed therein are not so broadly useful when used in concentrations of from 0.15% up to 4.0% (based on total weight of bleach or sterilizing solution) as to have the ability to be used in conjunction with perfume oils which should be incorporated into thickened, high viscous hypochlorite bleaches or sterilizers having excellent surface tension properties so that long lasting stable soluble single phase thickened perfumed aqueous alkali metal hypochlorite bleach or sterilizing solutions having long lasting pleasing stable aromas are obtained, particularly where the quantity of perfume oil in the bleach or sterilizing substance is at levels of between 0.02% and 0.8% by weight of the total bleach or sterilizing solution. The need for such aromas (e.g., "citrusy") to be present in such bleach or sterilizing solutions exists so that the disagreeable characteristic "hypochorite" aroma is substantially eliminated from aromas of the product to which the bleach or sterilizing solution is applied; particularly on dry-out, as well as from the aroma of the hands of the user when they are in direct contact with such bleach or sterilizing solutions.

U.S. Pat. Nos. 3,560,389 also discloses the feasibility of using perfume oils in hypochlorite bleaches or sterilizers at column 3, lines 37–40 but the disclosure is limited to inclusion of various detergents in addition to amine oxides, such as lithium lauryl sulfate and sodium lauryl ether sulfate and/or is further limited to include hydrotropes such as sodium xylene sulfonate in addition to the amine oxide. Exclusion of such hydrotropes and detergents additional to the 2,4,4-trisubstituted tetrahydropyranol esters of our invention is desirable not only to cause 2,4,4-trisubstituted tetra-hydro pyranyl esters of our invention to function properly, but also from an ecological standpoint.

European Chemical News, Volume 13, Jan. 18, 1968, sets forth a stbiosus of South African Pat. No. 67/4667 which corresponds to U.S. Pat. No. 3,560,389, but the reference also states at page 42:

"Alternatively, a detergent with bleaching or bacteriocidal properties can be formulated. Perfuming bleaching solutions is now possible."

Neither the South African nor the U.S. patents, however, indicate the advantages and usefulness of limiting the detergents either to (a) compounds having the generic structure:

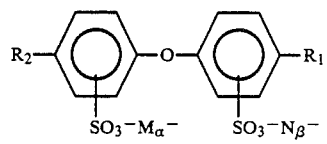

wherein at least one of $R_1$ and $R_2$ represents $C_{10}$–$C_{12}$ straight chain or branched chain alkyl and when one of $R_1$ or $R_2$ is $C_{10}$–$C_{12}$ branched or straight chain alkyl, the other or $R_1$ or $R_{12}$ is pH-adjusted hydrogen and wherein $M_\alpha$ and $M_\beta$ are the same or different and each represents alkali metal which may be sodium, lithium or potassium, or (b) to mixtures of compounds having the structure:

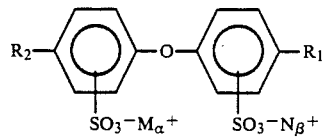

with at least 2,4,4-trisubstituted tetrahydro pyranyl esters defined according to the structure:

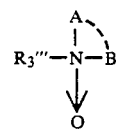

of excluding from the formulation a hydrotrope or of specifying the nature of the perfume oil useful in the perfumed bleach or sterilizing solution (wherein A and B are each separately methyl or taken together, complete a morpholino ring and wherein $R_3''$ is straight chain alkyl having from 11 up to 13 carbon atoms).

U.S. Pat. No. 3,876,551 in attempting to solve the foregoing problem discloses a stable single phase aqueous alkali metal hypochlorite liquid perfume bleach or sterilizing composition comprising an aqueous mixture of (1) an amino oxide composition consisting essentially of at least one morpholino and/or dimethyl ($C_{11}$–$C_{13}$ straight chain alkyl) amine oxide in an amount greater than 55% of said amine oxide composition, (2) at least one alkali metal hydroxide, (3) at least one alkali metal hypochlorite, and (4) a perfume oil compatible with the mixture capable of imparting a "woody" or a "floral" or a "clean fresh" or a "citrusy" note to the bleach or sterilizing composition; the mixture having a pH in the range of from 12 to 13.5 and the mixture excluding hydrotropes as well as all surfactants except the amine oxide. U.S. Pat. No. 3,876,551 also attempts to solve the foregoing problem by disclosing a process for producing the above-named mixture comprising the steps of combining an amine oxide composition consisting essentially of one or more morpholio and/or dimethyl $C_{11}$–$C_{13}$ straight chain alkyl amine oxide(s) with the perfumed oil to form an amine oxide-perfume oil premix; admixing the amine oxide-perfume oil premix with an aqueous alkali metal hypochlorite solution, and combining an alkali metal hydroxide with the solution whereby the final pH of the mixture is from 12 up to 13.5. In a further effort to solve the foregoing problem U.S. Pat. No. 3,876,551 also discloses adjustment of the pH of the aqueous metal hypochlorite solution initially to the range of 12–13.5 and then combining the resulting aqueous hypochlorite solution with the aforementioned premix. The resulting composition is indicated to cause products to which said composition is applied to have eliminated there from the disagreeable characteristics "hypochlorite" aroma and instead to have a "clean fresh" or "floral" or "woody" or "citrusy" aroma to be imparted to the treated products. In addition, it is stated that the hands of the individual user after using and being in direct contact with the hypochlorite composition will not have the disagreeable characteristics "hypochlorite" aroma but instead will have a pleasant "clean fresh" or "floral" or "woody" or "citrusy" aroma.

The disadvantage of the system of U.S. Pat. No. 3,876,551 however, concerns (a) the inability to use a thickener in the system whereby the resulting liquid has a viscosity of 5–25 centipoises at 20°–40° C. and (b) the relatively low degree of chemical stability and substantive stability of the perfume oil and of the single liquid phase system. Nothing in U.S. Pat. No. 3,876,551 indicates such a high degree of stabilities of the perfume-hypochlorite system as exists in the system of the present invention; wherein there is also included a thickener. Indeed, the stabilities using the system of the instant invention are far greater even at levels as low as 3% hypochlorite and are also relatively stable (from a standpoint of chemical stability of perfume oil, substantive stability of perfume oil and phase separation stability taken in combination with one another) at levels of as high as 10% hypochlorite in aqueous solution. Thus, the instant system gives rise to unexpected, unobvious and advantageous properties over the systems taught in the prior art.

Furthermore, nothing in the prior art including the teaching of U.S. Pat. No. 3,876,551 states either explicitly or implicitly the compatability of a thickener in the instant system, such as sodium palmitate, sodium stearate, potassium palmitate, potassium stearate, lithium palmitate, lithium stearate, lithium laurate, potassium laurate or sodium laurate whereby a stable gel (as opposed to a liquid) phase perfumed hypochlorite system or perfumed oil stabilizer emulsifier system "premix" may be produced.

The combination of the compound group having the structure:

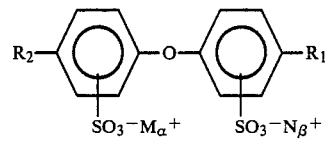

(wherein $R_1$, $R_2$, $M_\alpha$ and $M_\beta$ are defined, supra) with perfume and hypochlorite bleach in general, is set forth in the Kao Soap Company, Japanese Pat. No. 25515/79 filed on Nov. 2, 1973 and opened for public inspection on June 19, 1975. Thus, on page 2, at column 4, line 15, the compound:

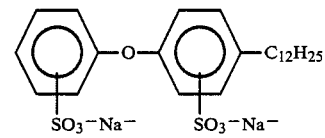

is disclosed for use in conjunction with the perfumed hypochlorite bleaches. The claim of the Kao Soap Patent is as follows:

"Claim: An aromatic liquid bleaching composition containing, as active ingredient, sodium hypochlorite, which comprises one or more of simple perfumes or compounded perfumes selected from the group consisting of anisole, benzophenone, benzylphenyl ether, bromelia, cedrenyl acetate, p-tertiary butylcyclohexanol, dimethylbenzylcarbinyl acetate, dihydroterpinyl acetate, diphenyl oxide, dimethylbenzylcarbinol, dimethylphenylcarbinol, dihydroterpineol, fenchyl acetate, fenchyl alcohol, p-methyldimethylbenzylcarbinol, methylphenylcarlbinyl acetate, methyl-n-valerate, muskmoskene, muscarone, methyl amyl ketone, phenylethyldimethylcarbinyl acetate, rose phenone, styrallyl propionate, tetra hydromuguol, tetra hydromuguyl acetate, tetrahydreolinalool acetate, verool, velveton, verdox, conifieran and yarayara, and a surface active agent which can be stably be dissolved in an aqueous solution of sodium hypochlorite."

Furthermore, the use of such compounds as those having the structure:

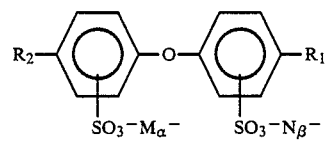

(wherein $R_1$, $R_2$, $M_\alpha$ and $M_\beta$ have been previously defined) with hypochlorite bleaches is documented in the brochure of Dow Chemical entitled "DOWFAX Surfactants" and is covered in the Dow Chemical Company U.S. Pat. No. 3,172,861 issued on Mar. 9, 1965.

Nothing in the prior art discloses, however, the utility of the thickeners of the instant application taken together with a perfume oil (e.g., at least one of the 2,4,4-trisubstituted tetrahydro pyranyl esters of our invention) and one of the compounds defined according to the generic structure:

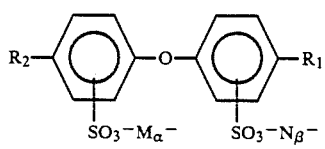

(wherein $R_1$, $R_2$, $M_\alpha$ and $M_\beta$ have been defined, supra) in hypochlorite bleaches, particularly where the hypochlorite concentration is greater than 7%. More particularly, nothing in the prior art discloses the use of such systems in conjunction with a thickener such as sodium palmitate, potassium palmitate, sodium stearate, potassium stearate, sodium laurate, potassium laurate, lithium laurate, lithium stearate orlithium palmitate, whereby a stable gelled perfumed hypochlorite mixture is formed or whereby a "premix" gel-hase perfume oil-stabilizing-/emulsifying agent is formed.

The 2,4,4-trisubstituted tetrahydro pyranyl esters of our invention are unique insofar as the aforementioned systems are concerned for use in hypochlorite bleaches. Nothing in the prior art discloses any organic compounds even remotely similar to the 2,4,4-trisubstituted tetrahydro pyranyl esters of our invention for use as a stable aroma augmenting or enhancing agent in hypochlorite bleaches.

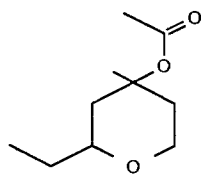

(Conditions: SE-30 column programmed at 180° C. isothermal).

Figure 2:
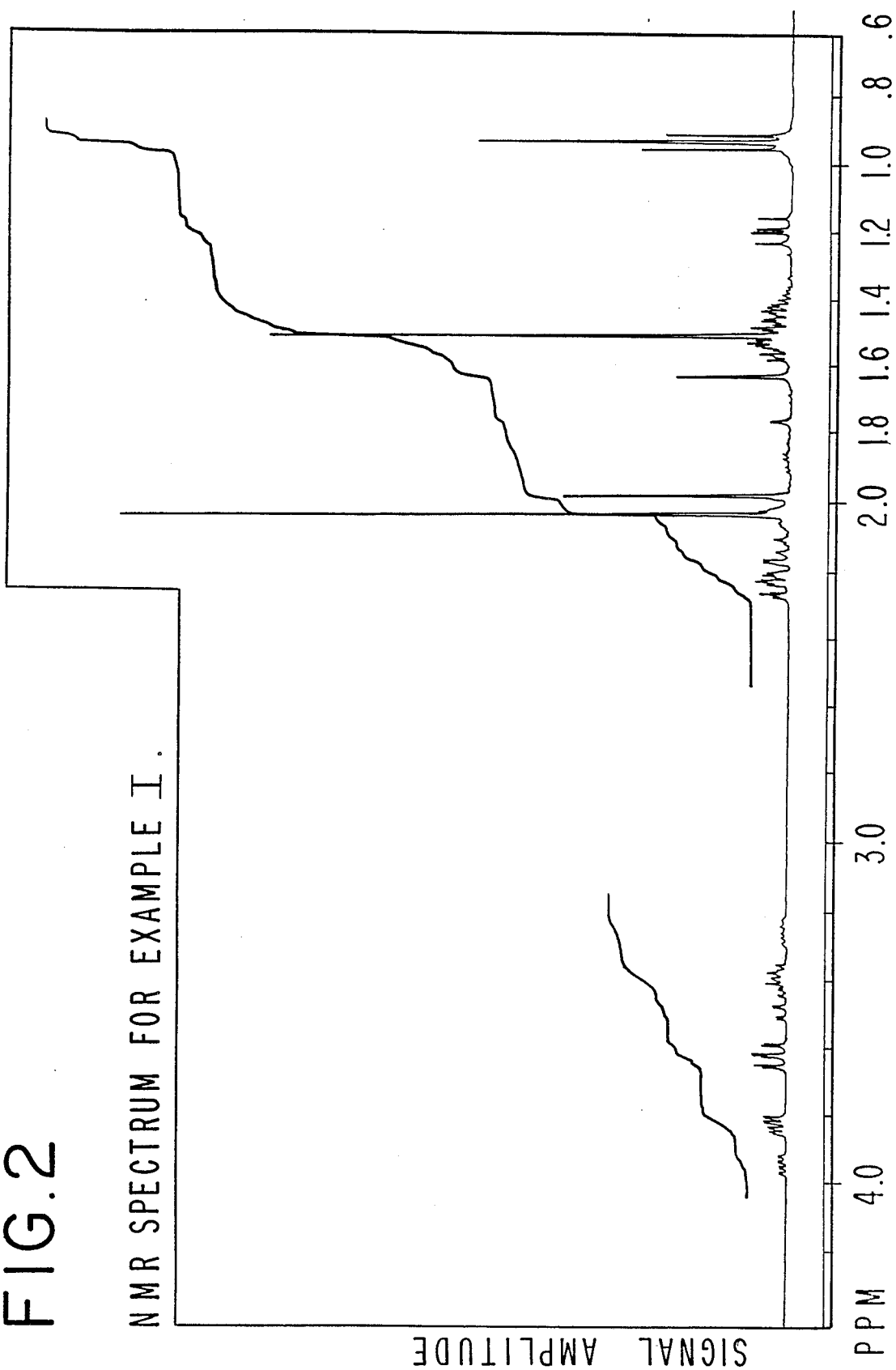

FIG. 2 is the NMR spectrum for the compound having the structure:

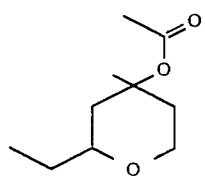

produced according to Example I.

Figure 3:
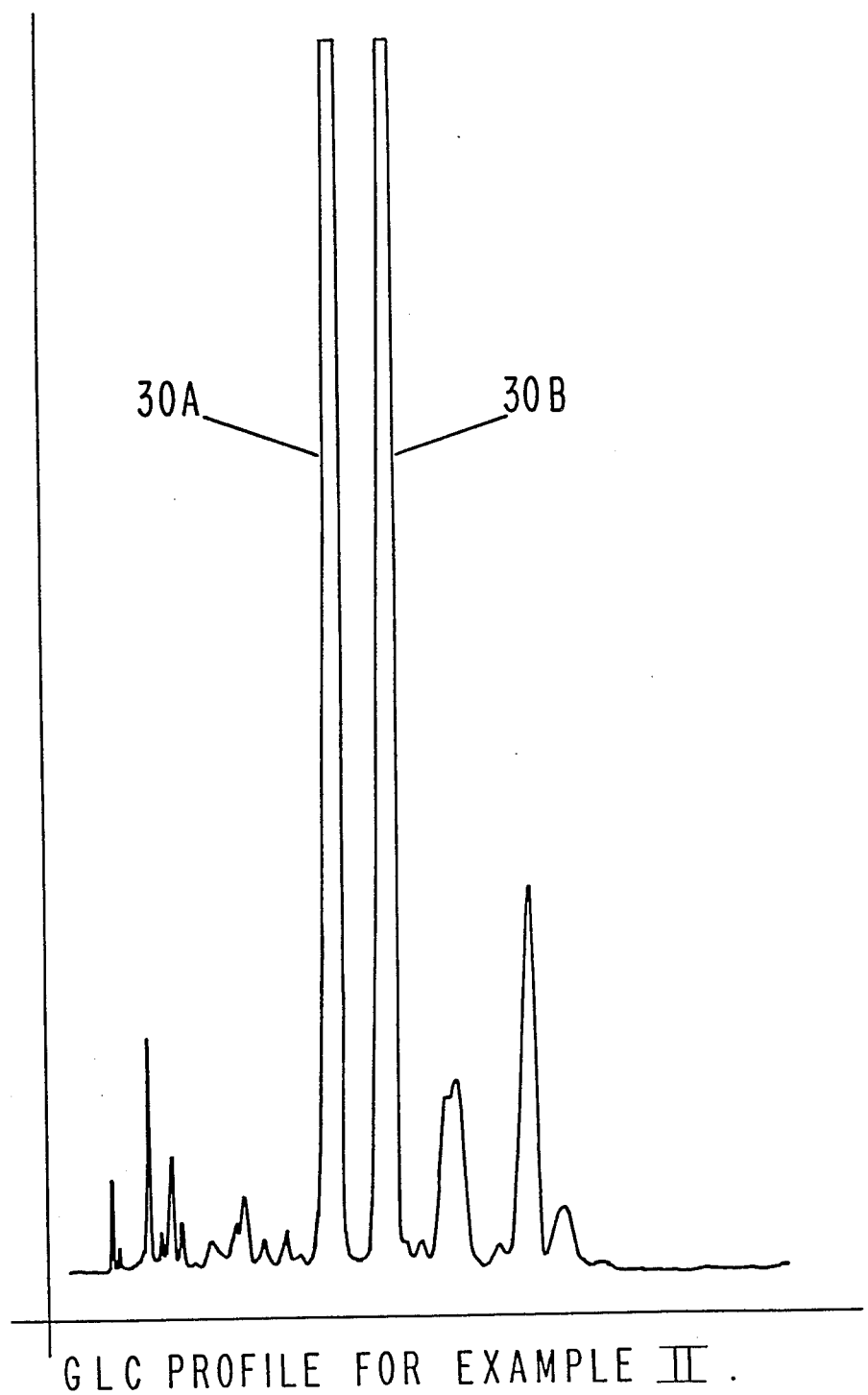

FIG. 3 is the GLC profile for the reaction product of Example II containing the compound having the structure:

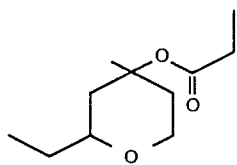

(Conditions: SE-30 column programmed at 180° C. isothermal).

Figure 4:
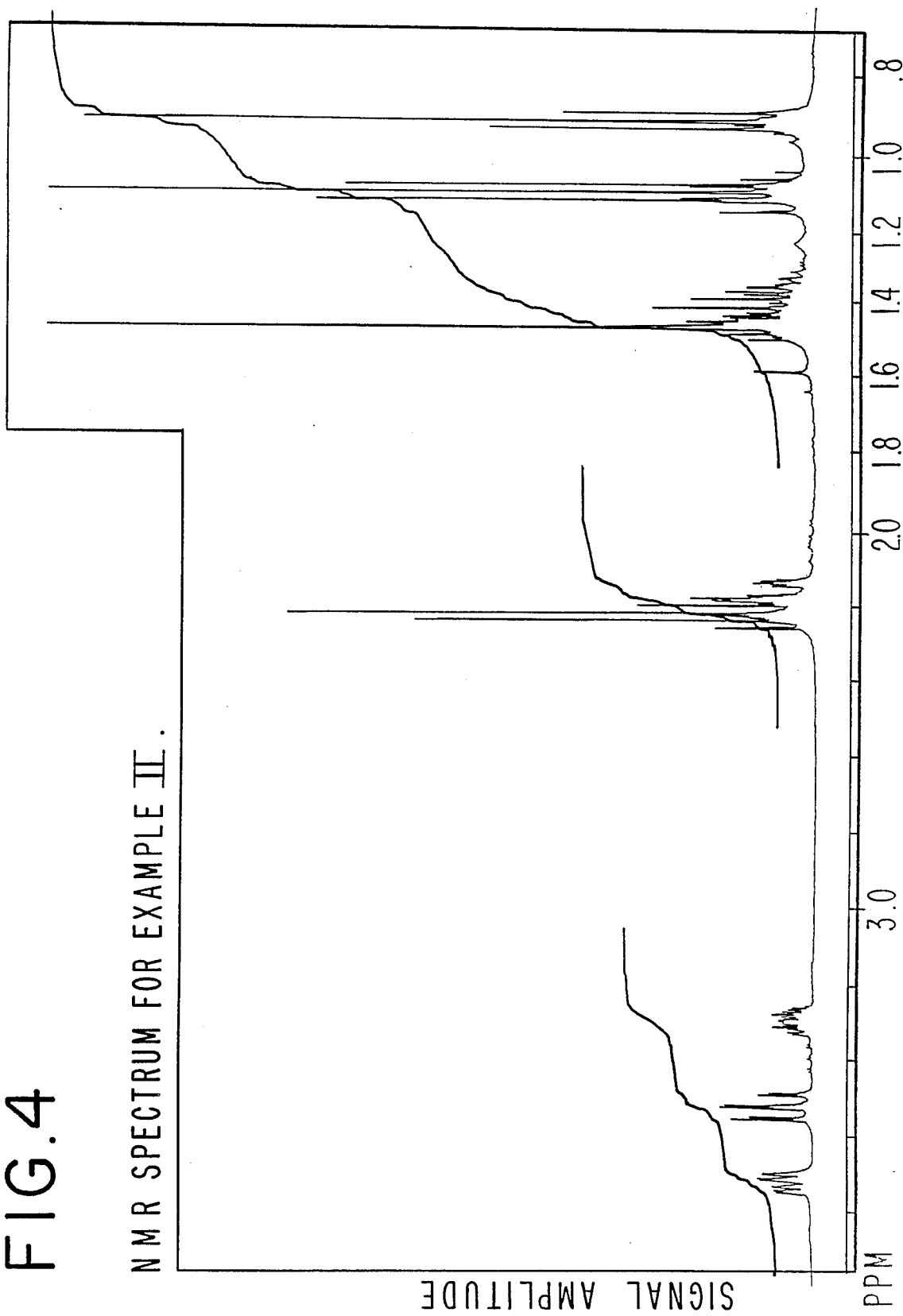

FIG. 4 is the NMR spectrum for the compound having the structure:

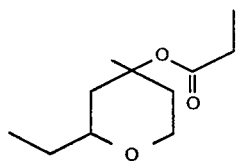

produced according to Example II.

Figure 5:
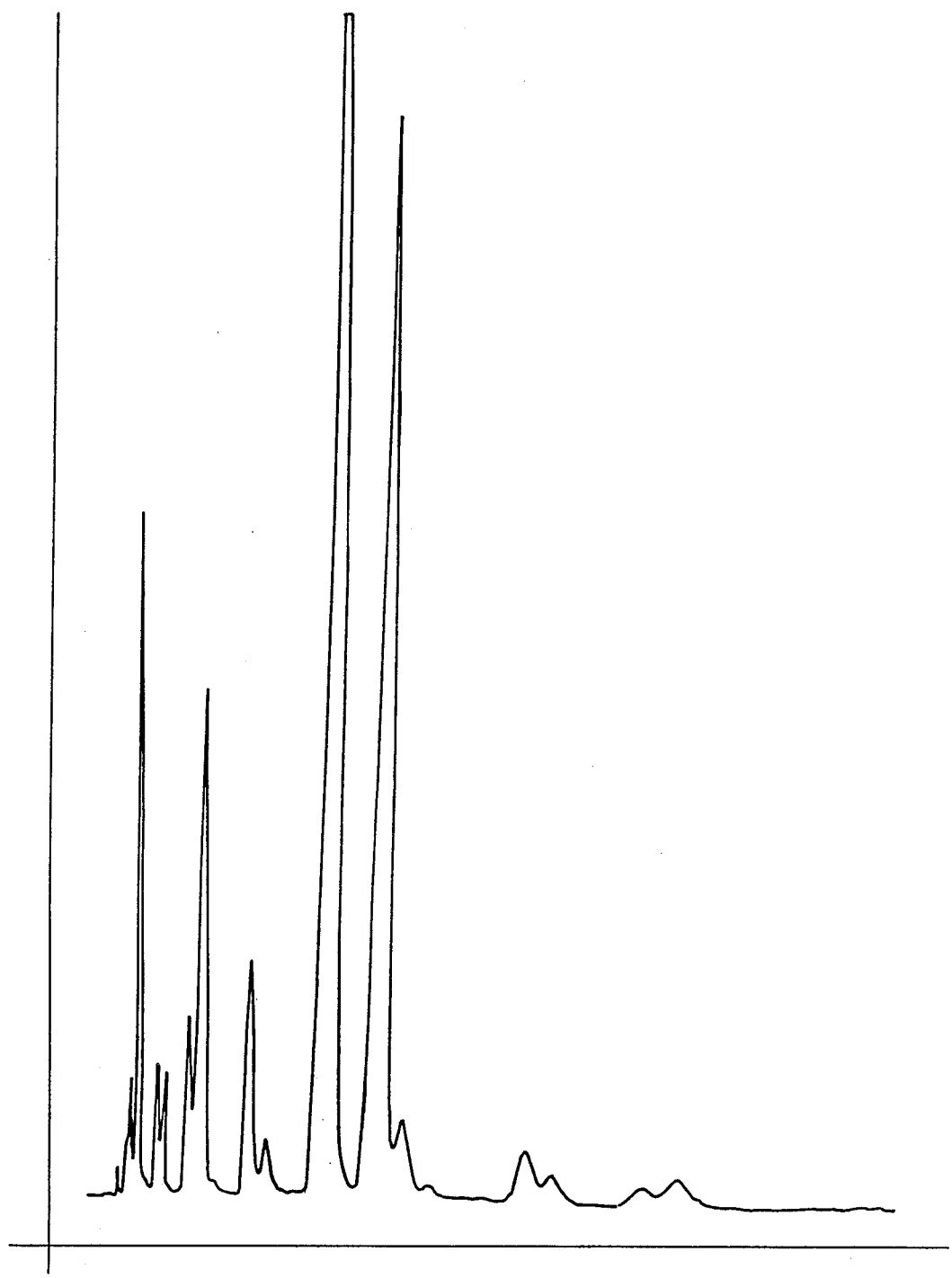

FIG. 5 is the GLC profile for the reaction product of Example III containing the compound having the structure:

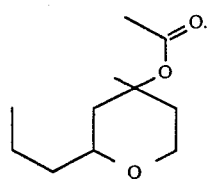

Figure 6:
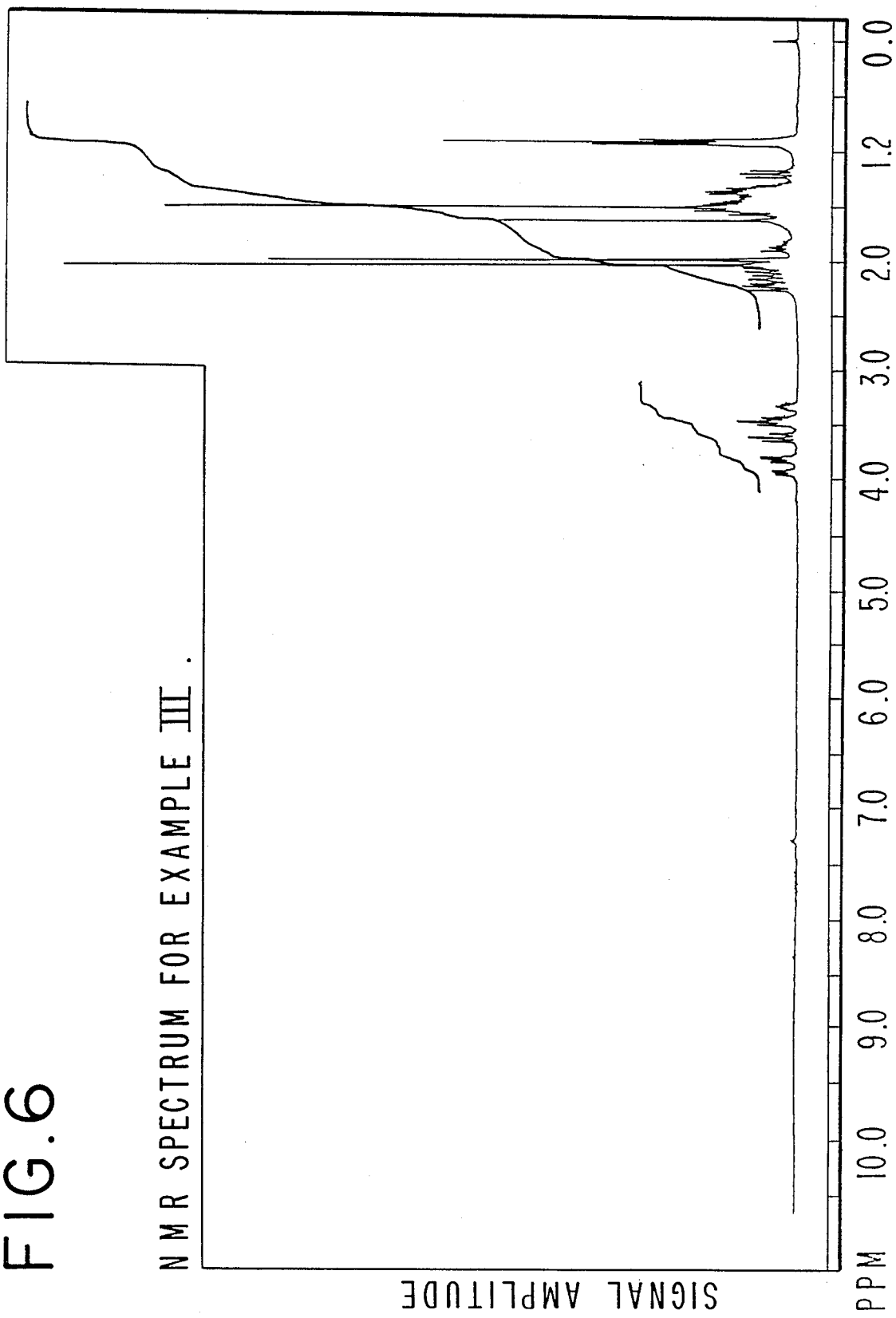

FIG. 6 is the NMR spectrum for the compound having the structure:

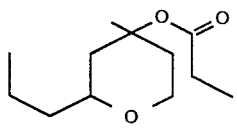

prepared according to Example III.

Figure 7:
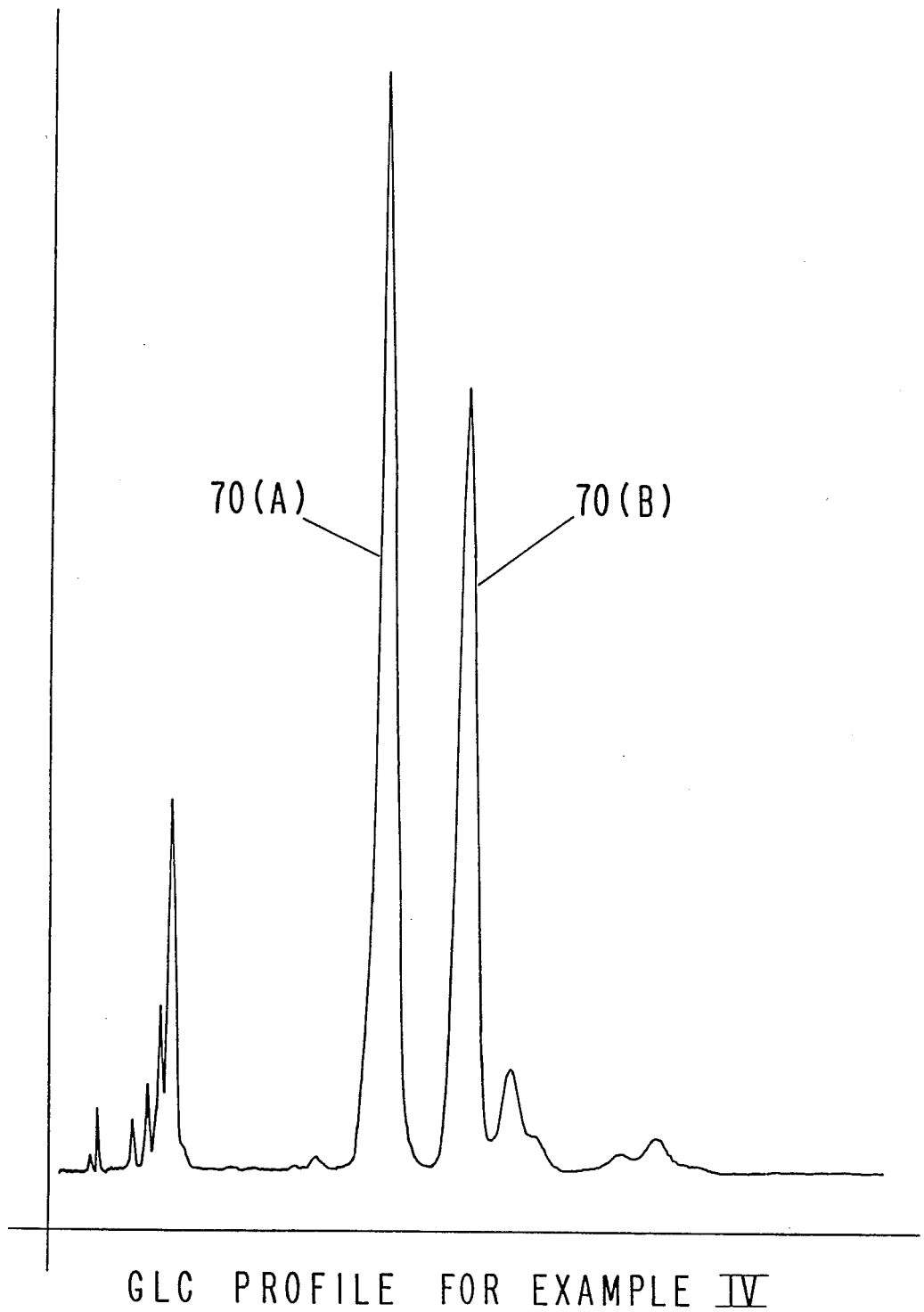

FIG. 7 is the GLC profile for the reaction product of Example IV containing the compound having the structure:

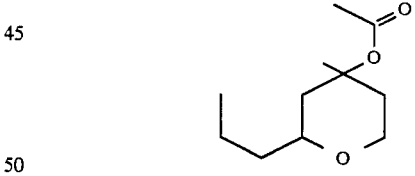

(Conditions: SE-30 column programmed at 180° C. isothermal).

Figure 8:
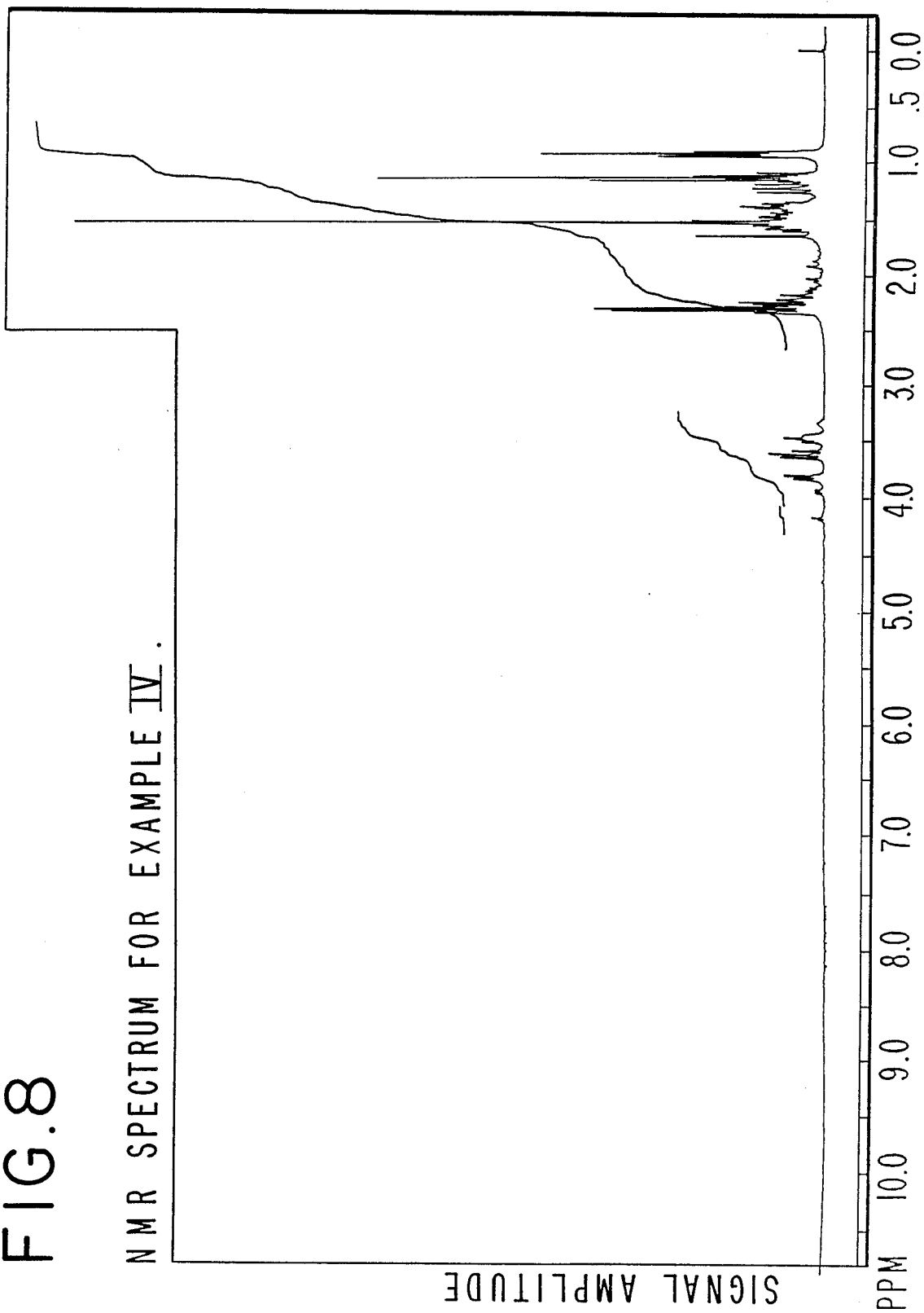

FIG. 8 is the NMR spectrum for the compound having the structure:

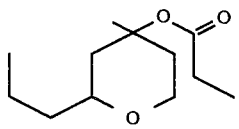

prepared according to Example IV.

Figure 9:
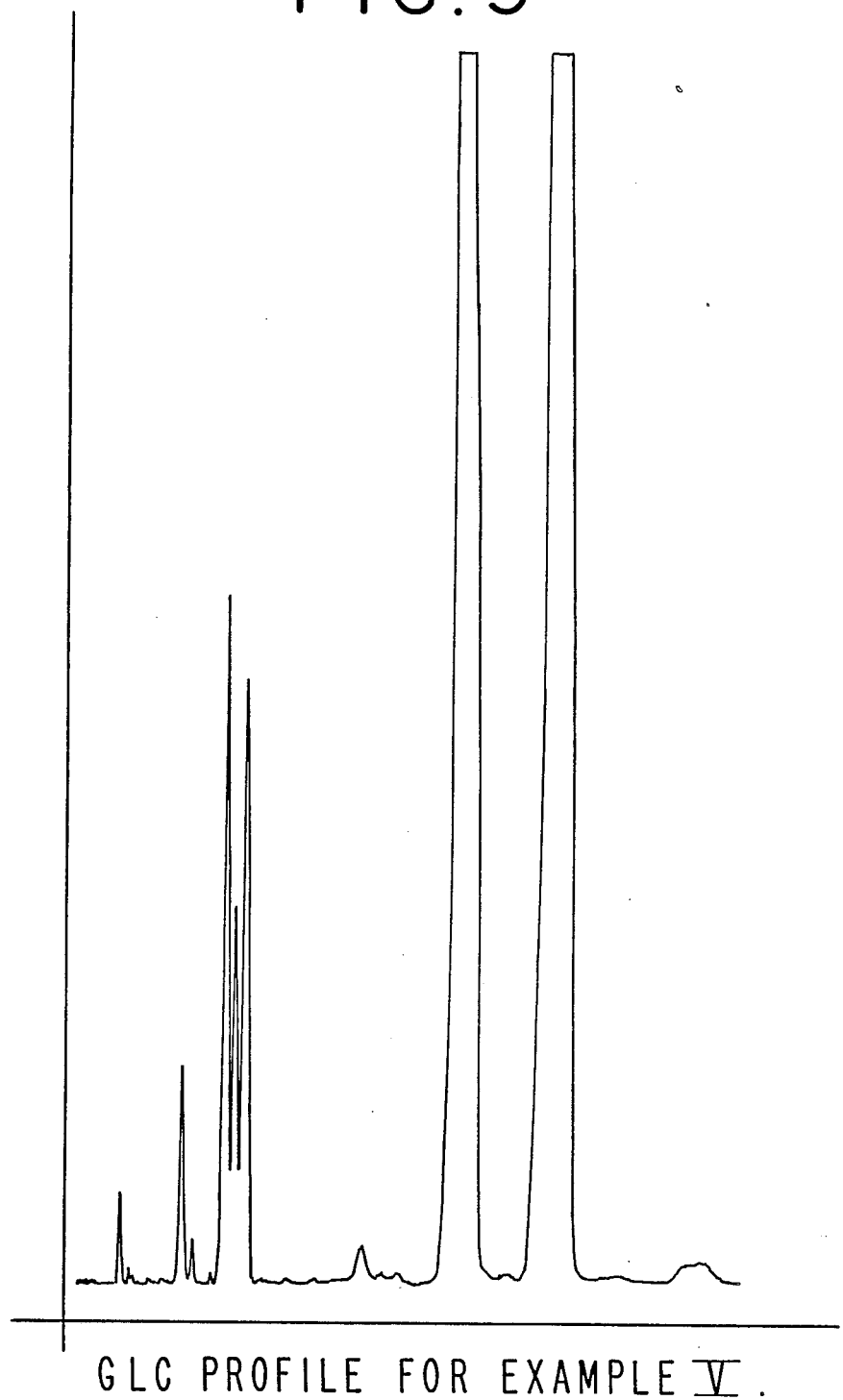

FIG. 9 is the GLC profile for the reaction product of Example V containing the compound having the structure:

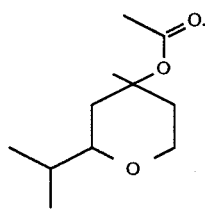

Figure 10:
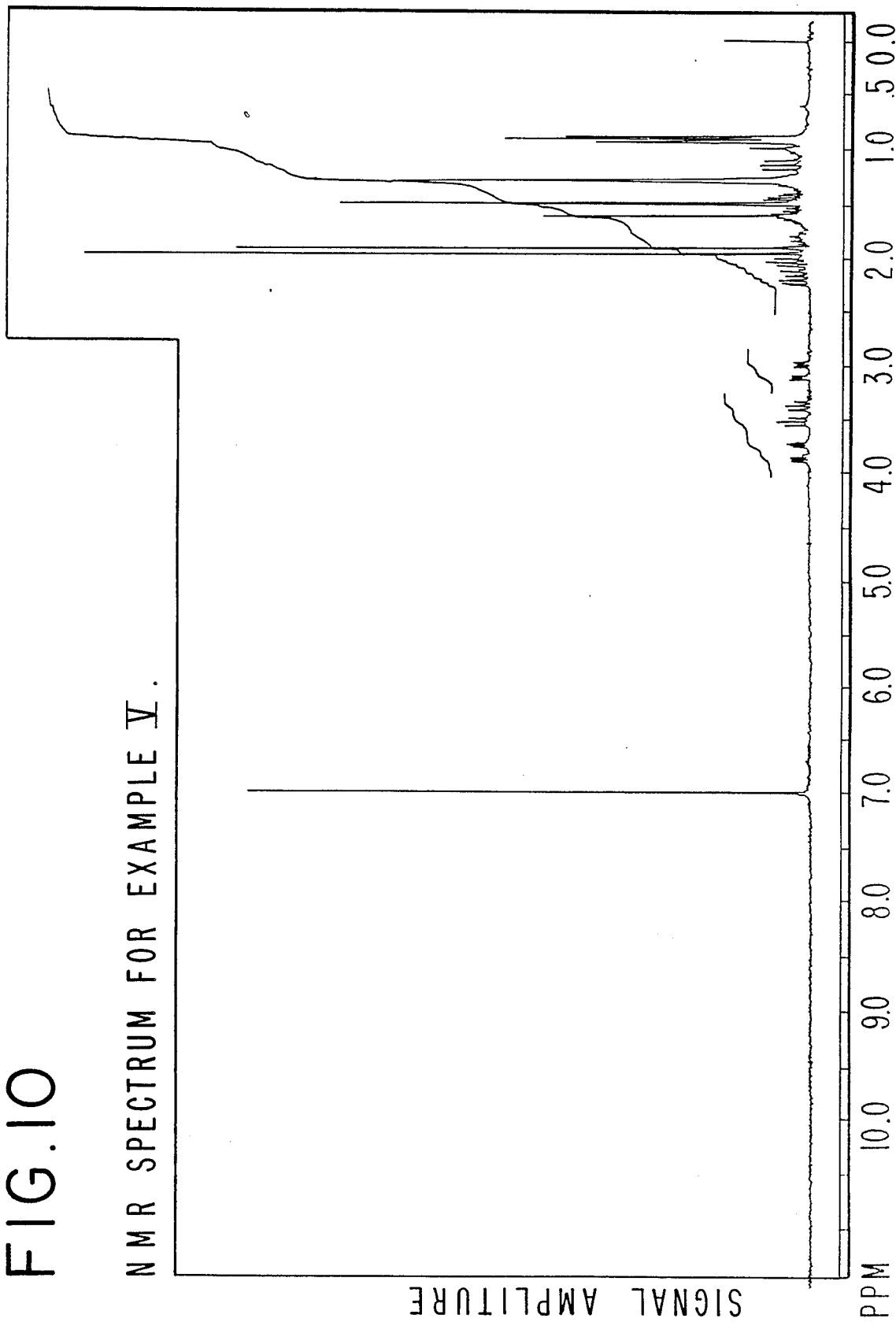

FIG. 10 is the NMR spectrum for the compound having the structure:

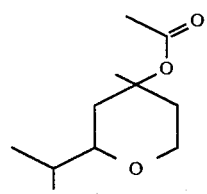

produced according to Example V.

Figure 11:
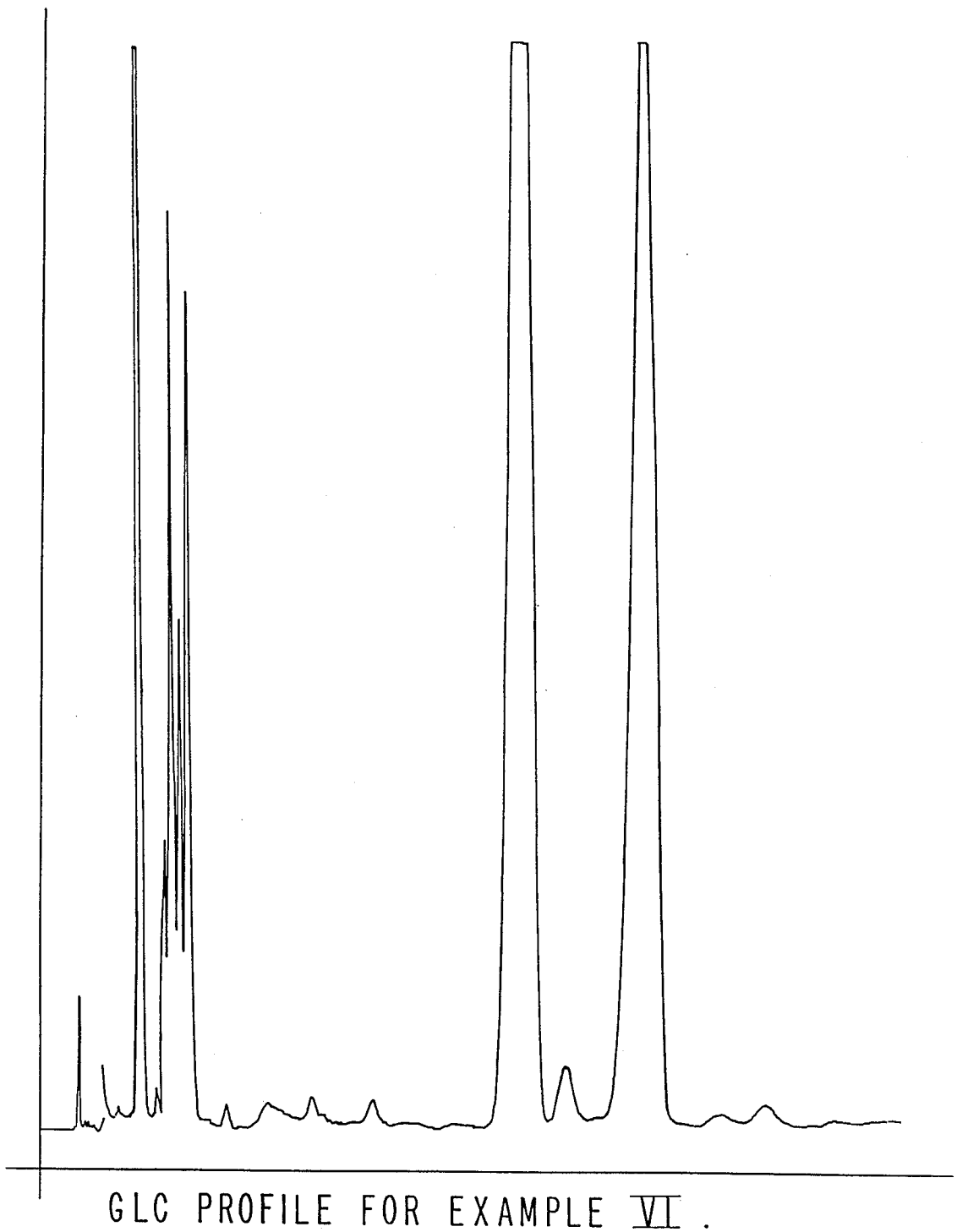

FIG. 11 is the GLC profile for the reaction product of Example VI containing the compound having the structure:

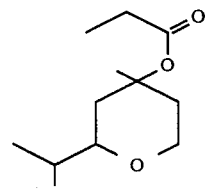

(Conditions: SE-30 column programmed at 160° C. isothermal).

Figure 12:
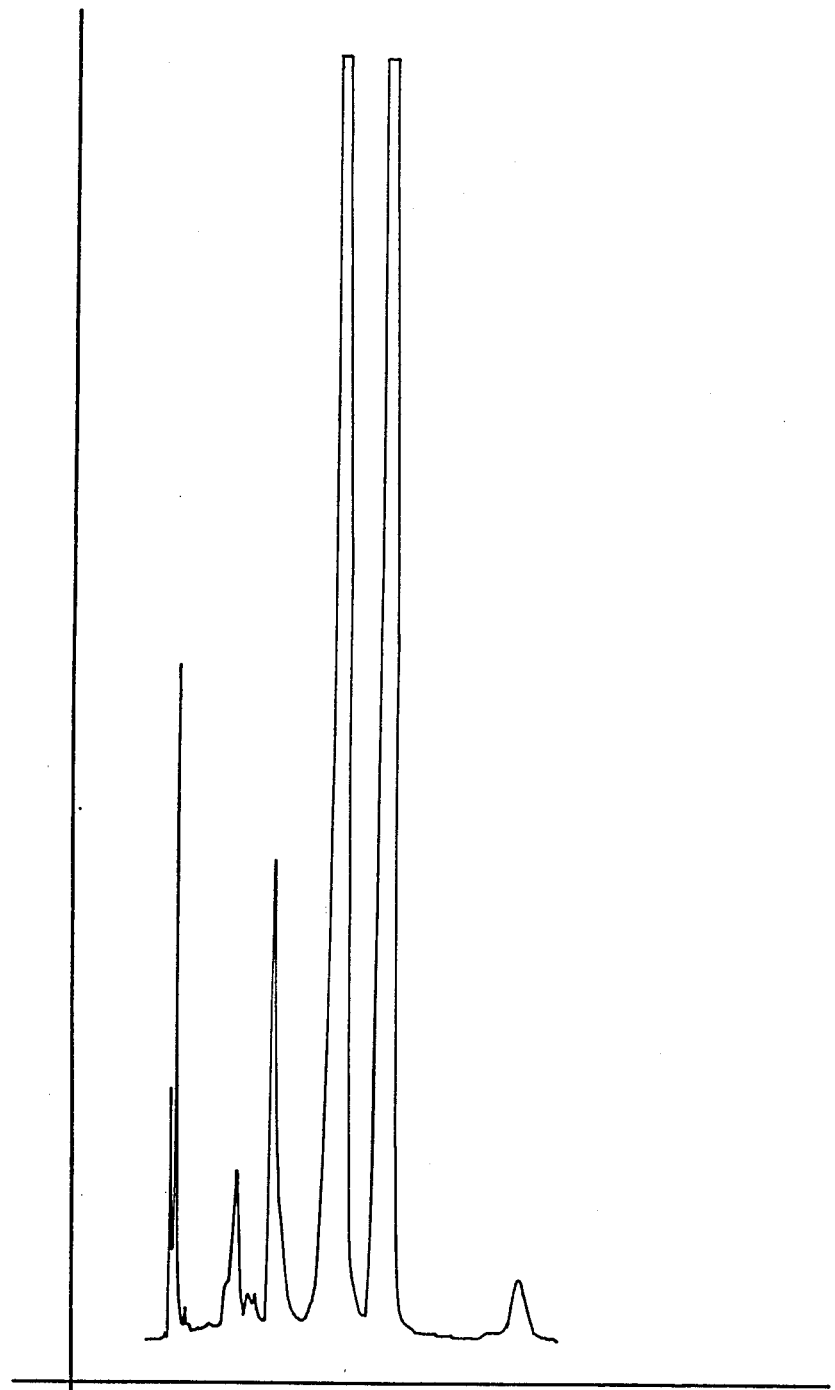

FIG. 12 is the GLC profile for the reaction product of Example VII containing the compound having the structure:

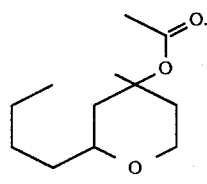

Figure 13:
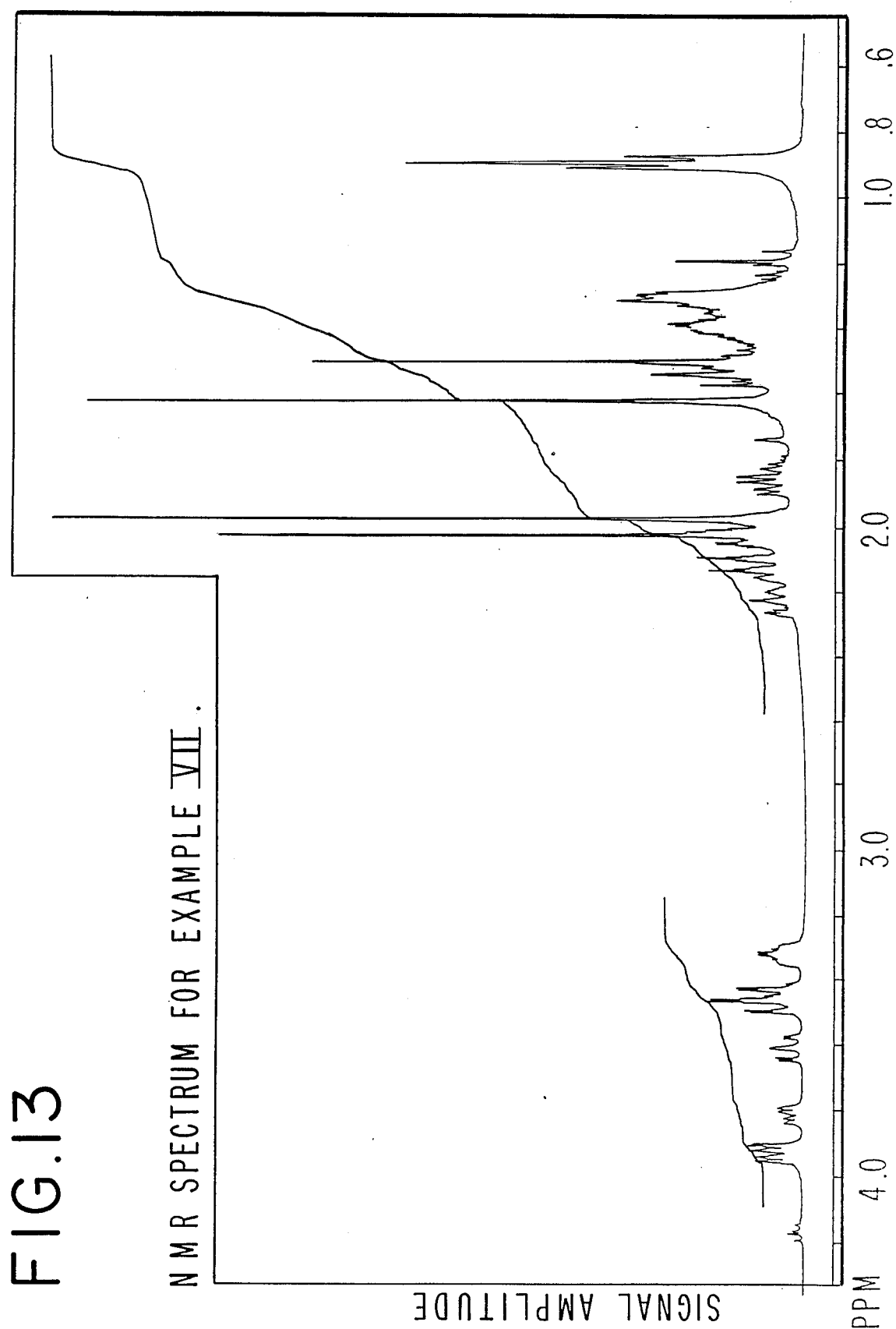

FIG. 13 is the NMR spectrum for the compound having the structure:

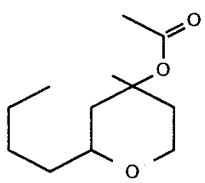

prepared according to Example VII.

Figure 14:
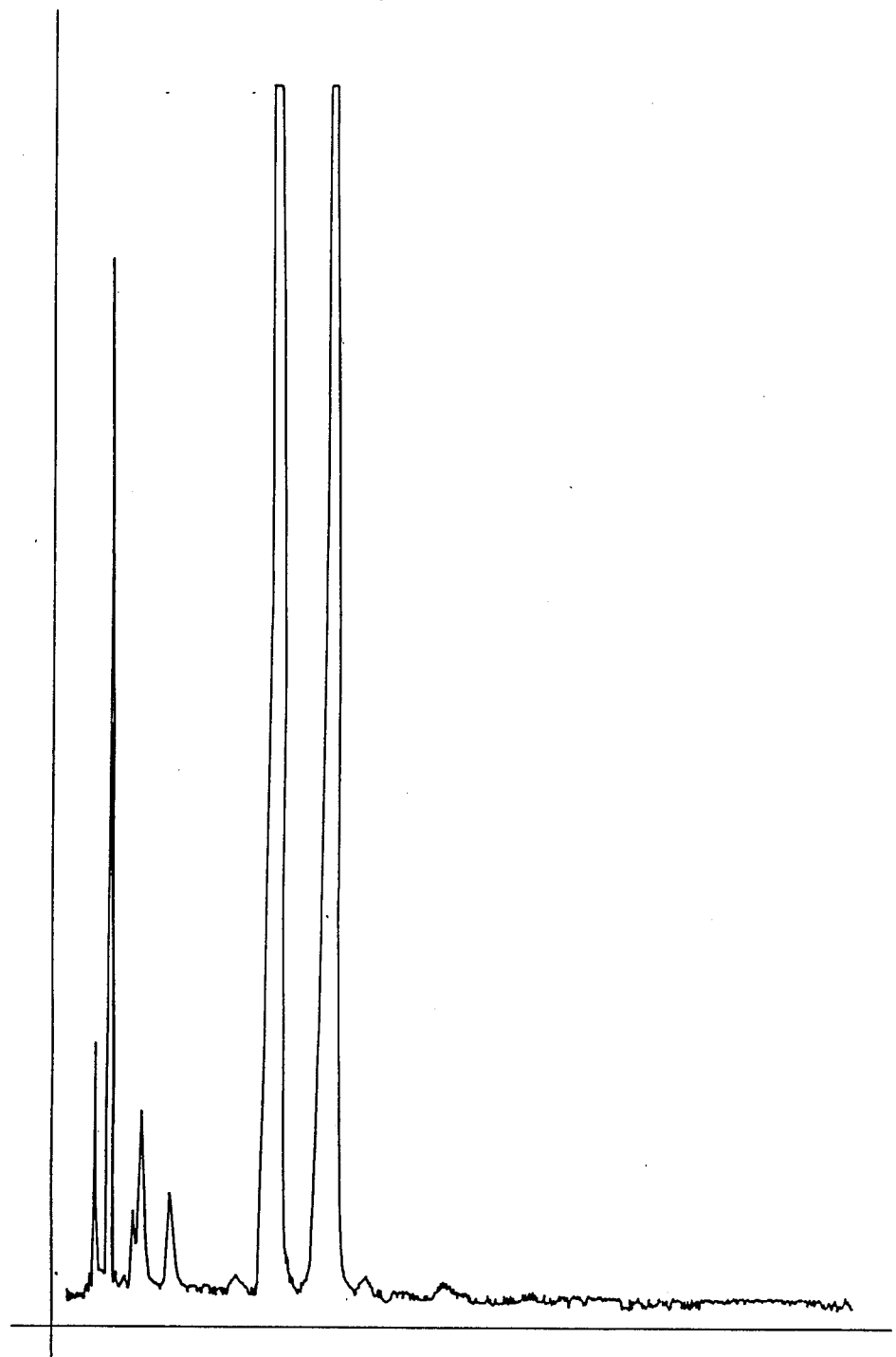

FIG. 14 is the GLC profile for the reaction product of Example VIII containing the compound having the structure:

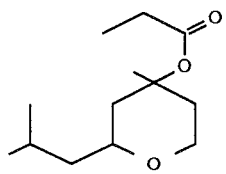

(Conditions: SE-30 column programmed at 180° C. isothermal).

Figure 15:
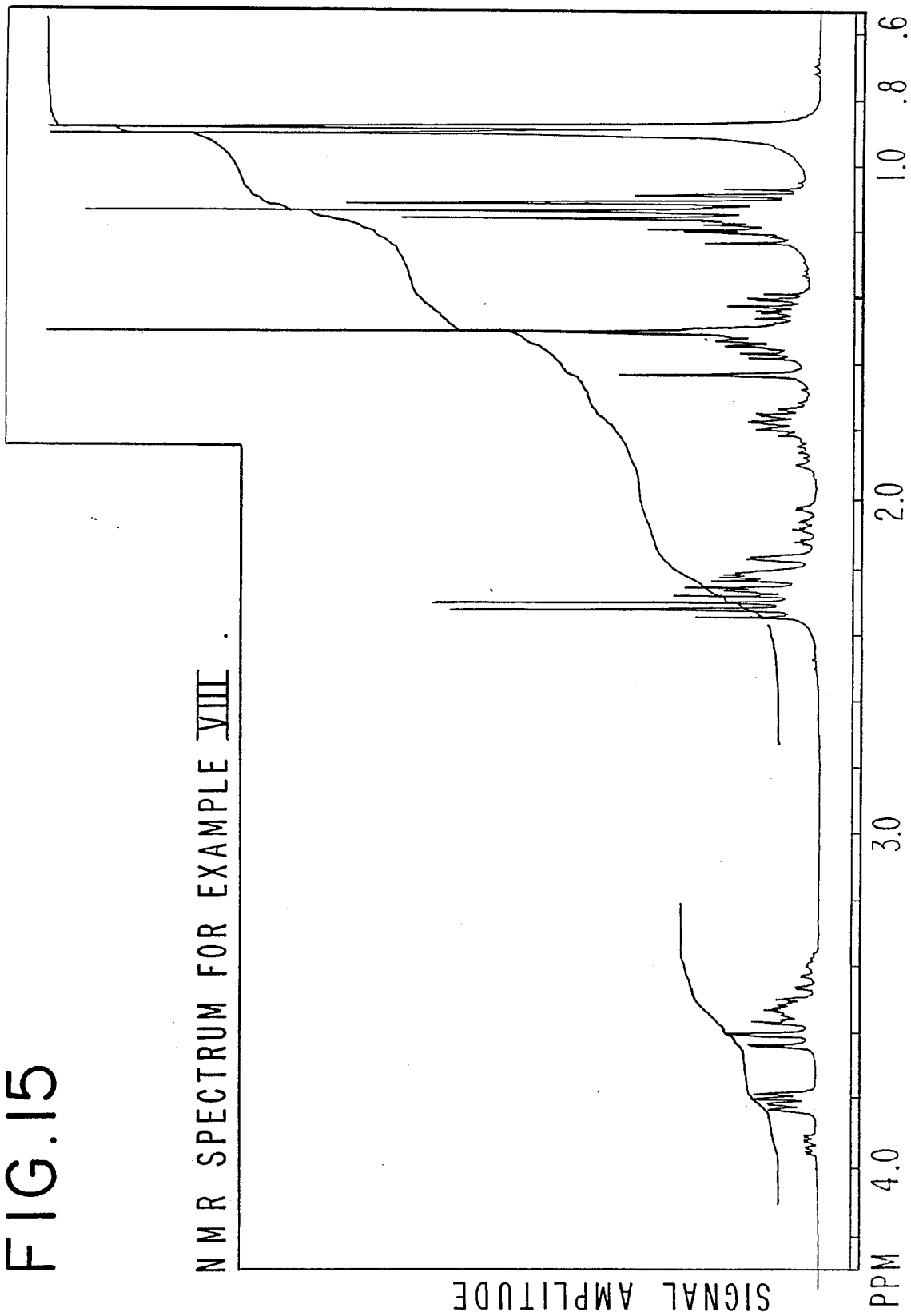

FIG. 15 is the NMR spectrum for the compound having the structure:

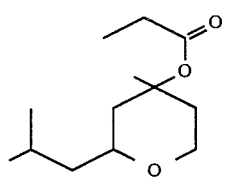

prepared according to Example VIII.

Figure 16:
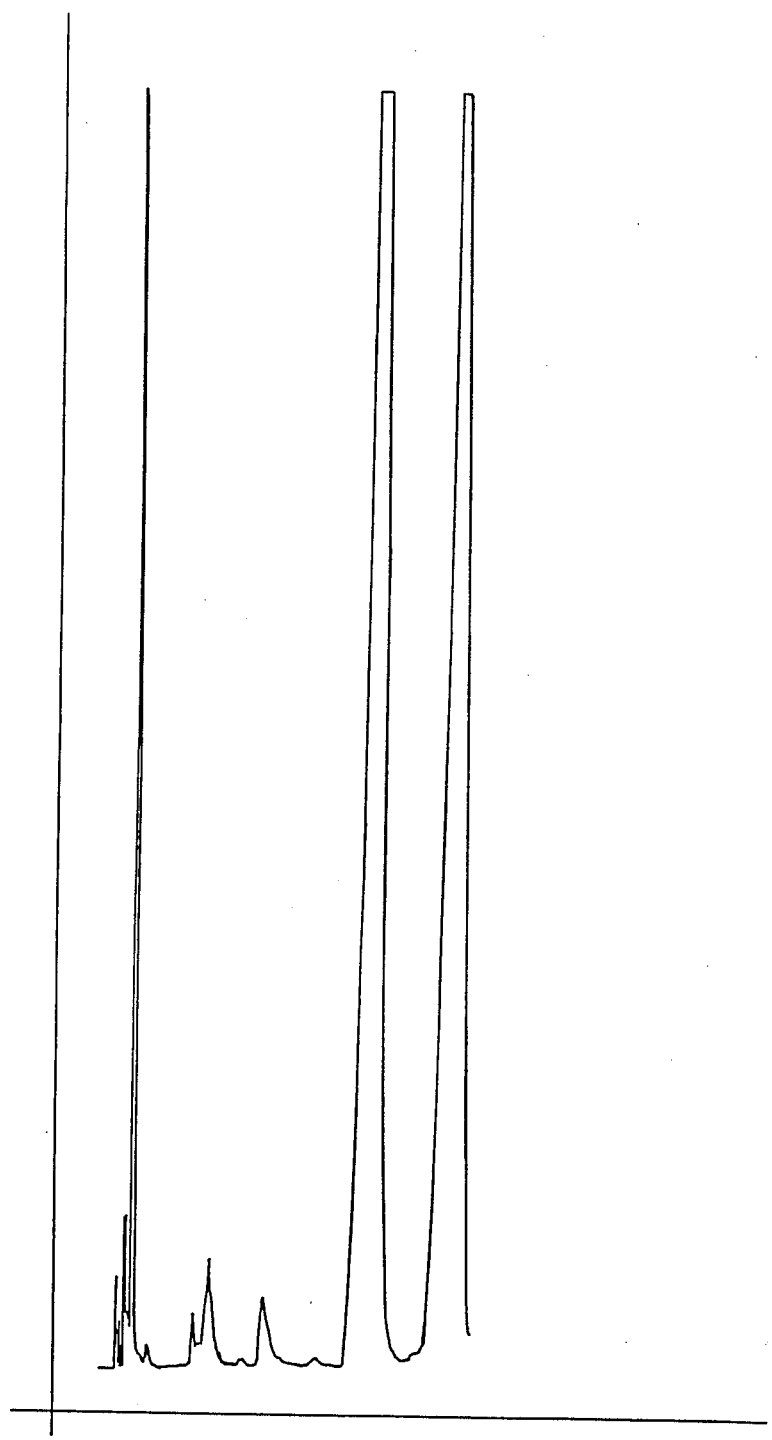

FIG. 16 is the GLC profile for the reaction product of Example IX containing the compound having the structure:

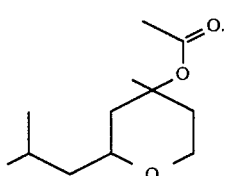

Figure 17:
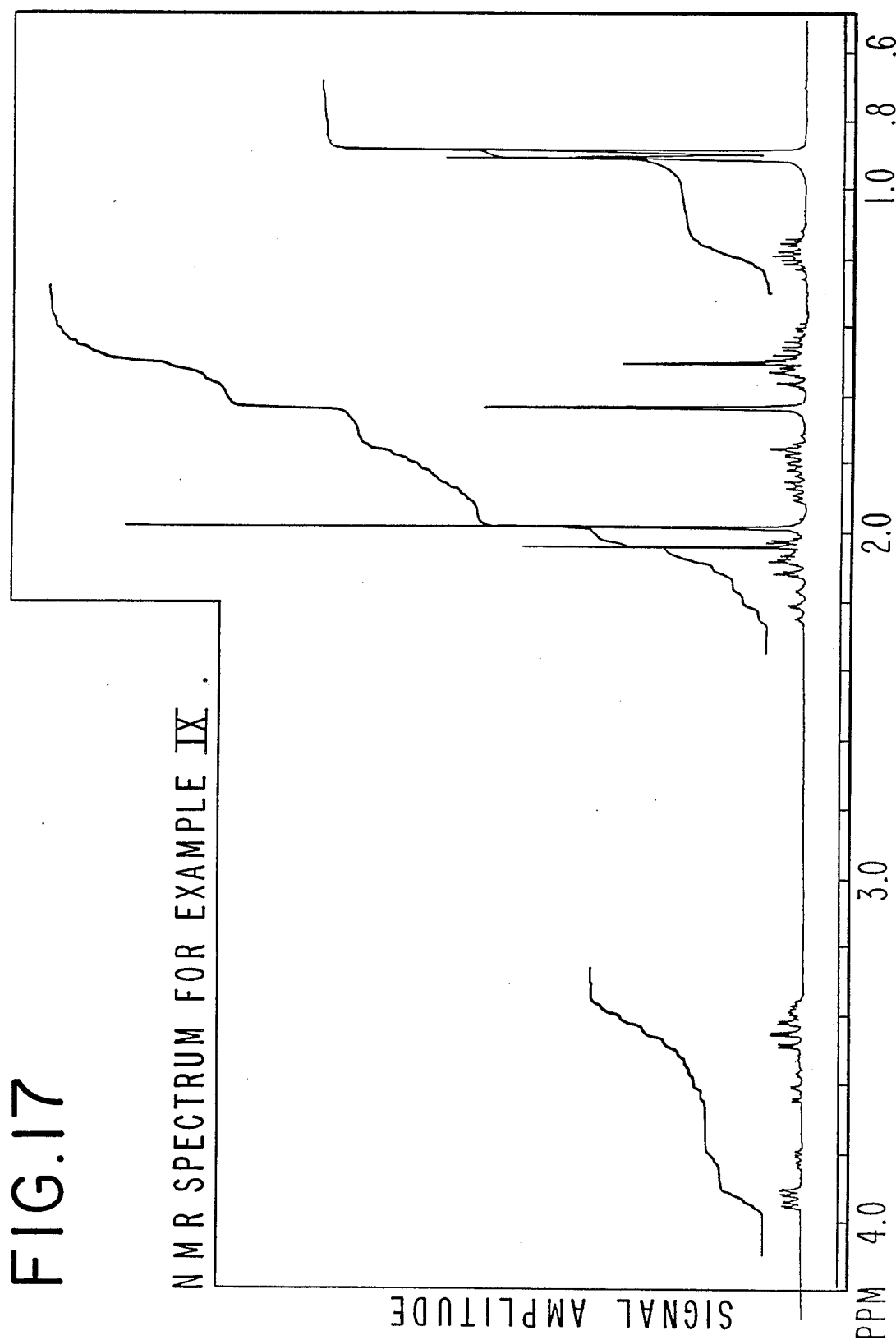

FIG. 17 is the NMR spectrum for the compound having the structure:

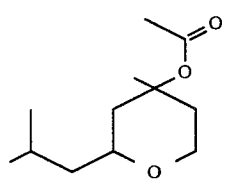

prepared according to Example IX.

Figure 18:
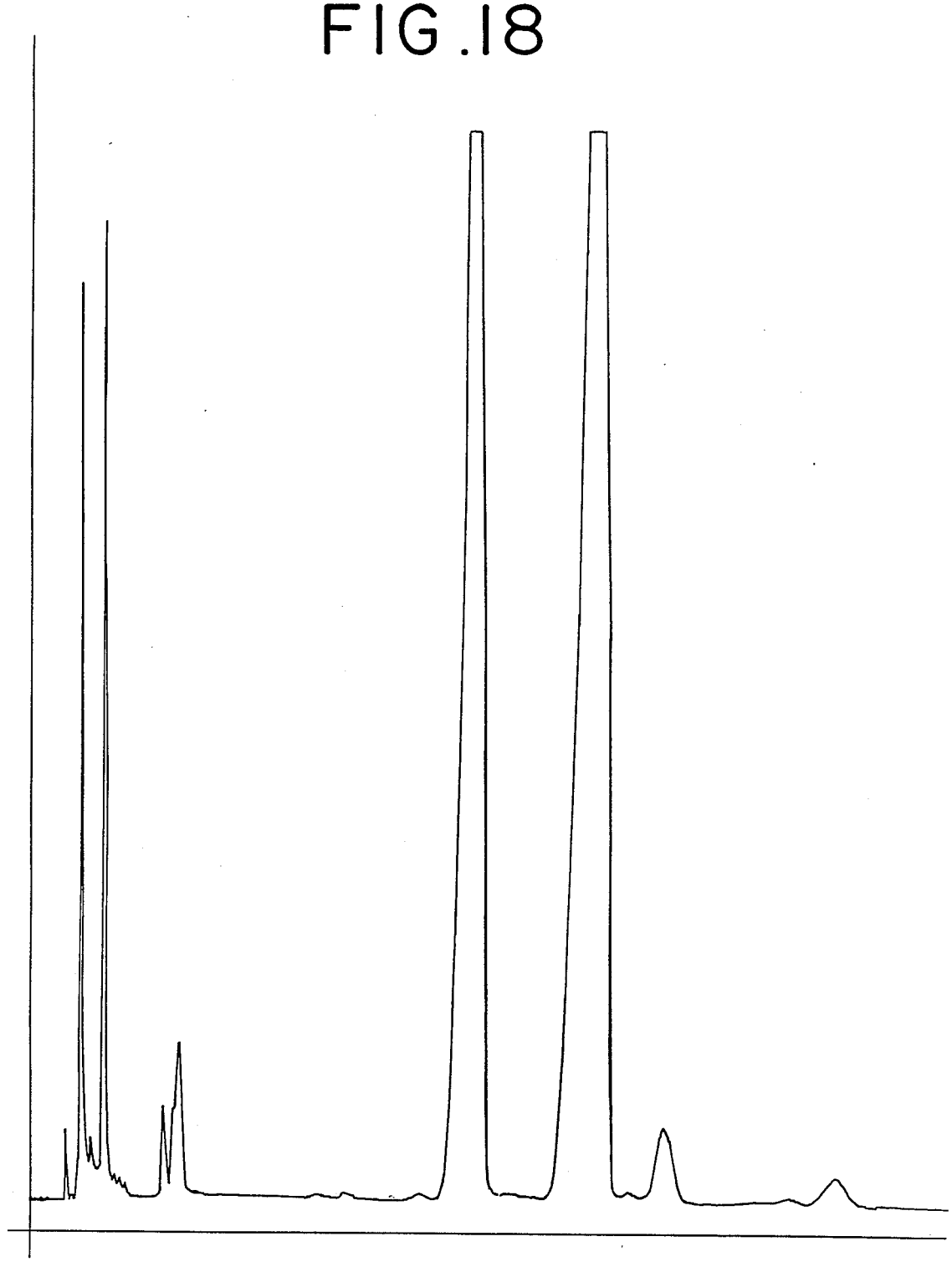

FIG. 18 is the GLC profile for the reaction product of Example X containing the compound having the structure:

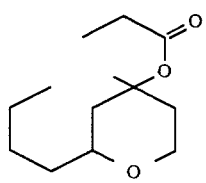

(Conditions: SE-30 column programmed at 180° C. isothermal).

Figure 19:
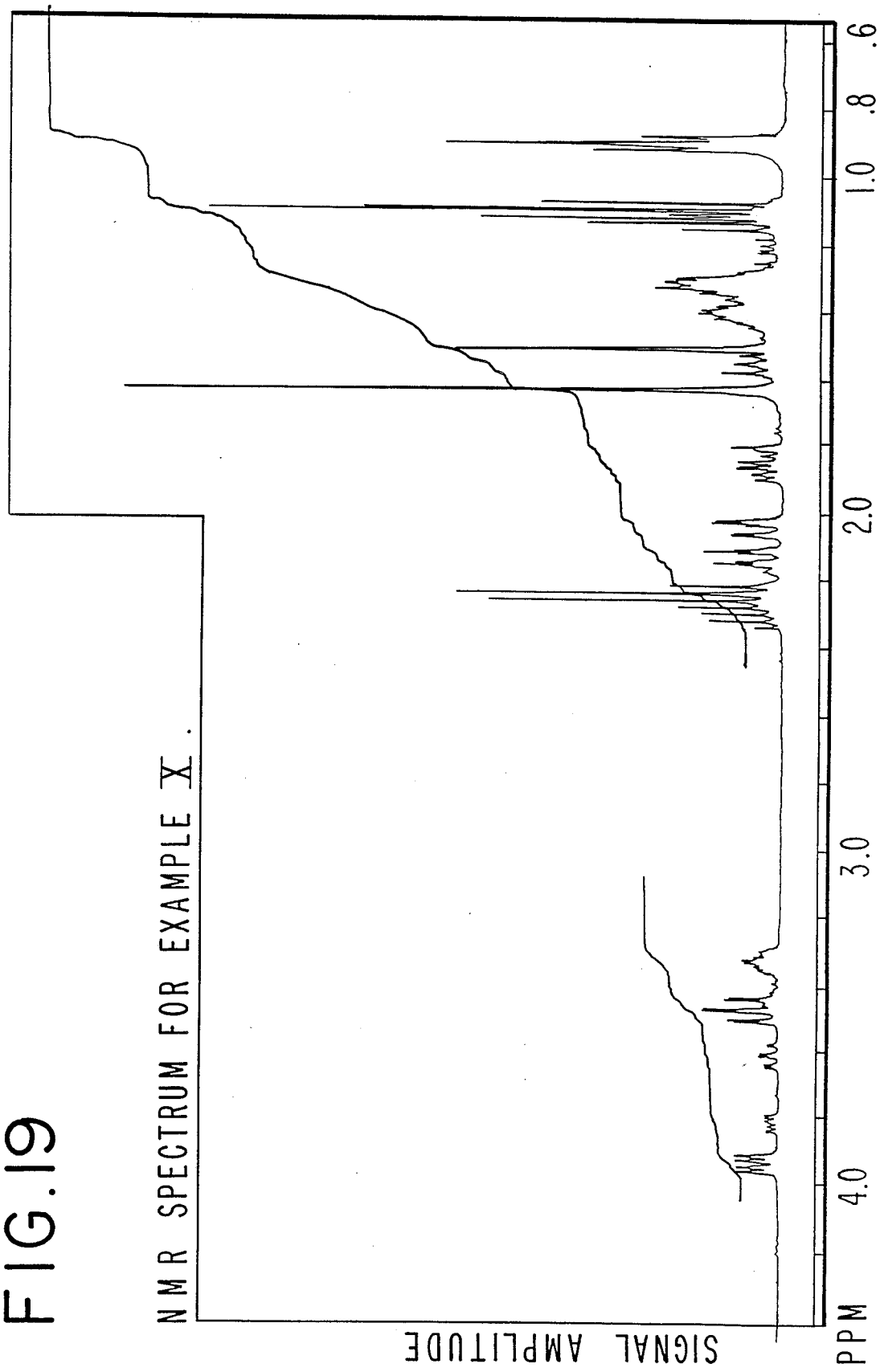

FIG. 19 is the NMR spectrum for the compound having the structure:

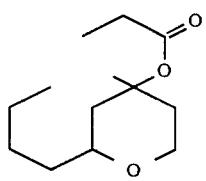

prepared according to Example X.

Figure 20:
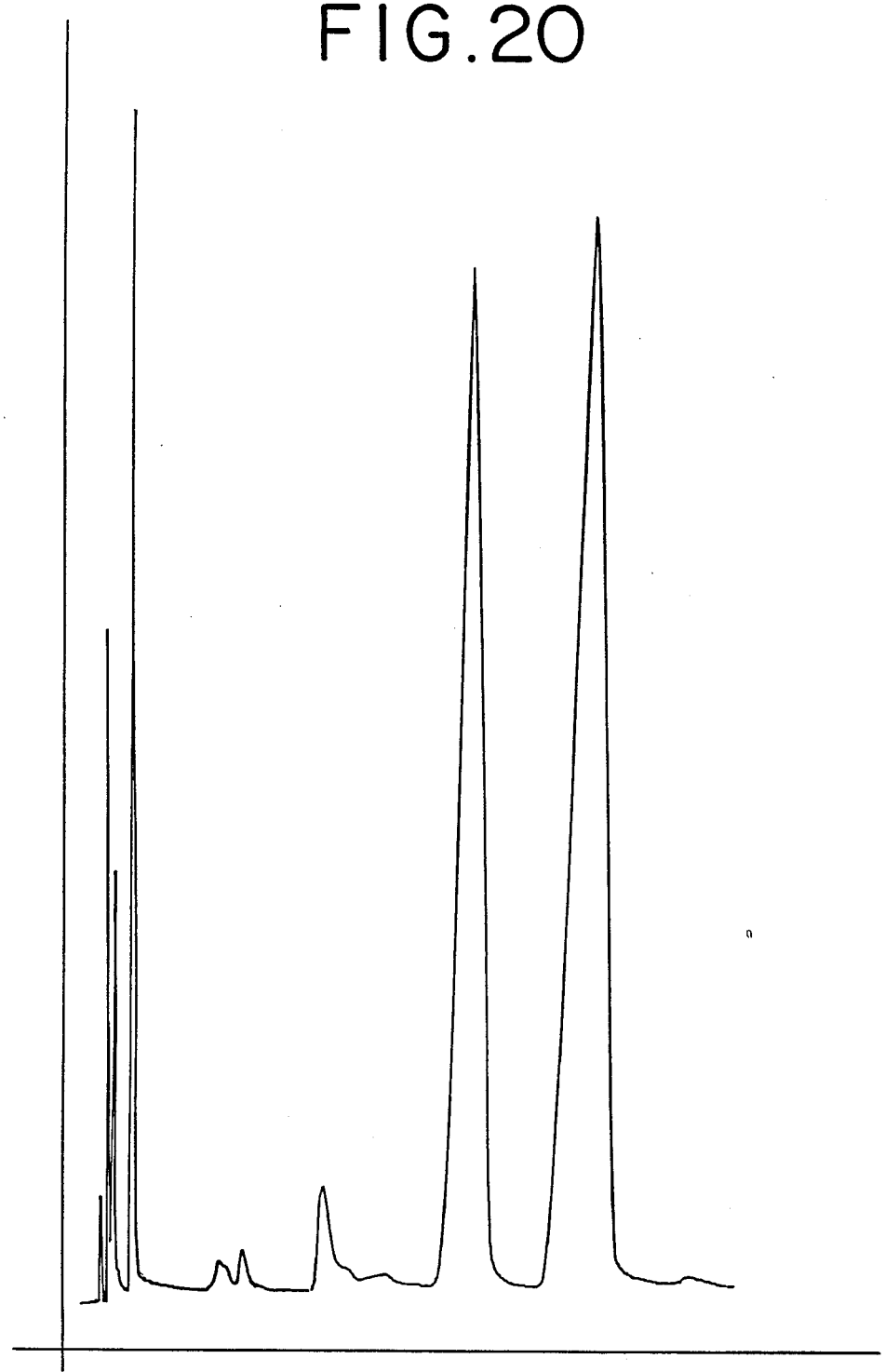

FIG. 20 is the GLC profile for the reaction product of Example XI containing the compound having the structure:

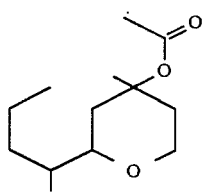

(Conditions: SE-30 column programmed at 180° C. isothermal).

Figure 21:
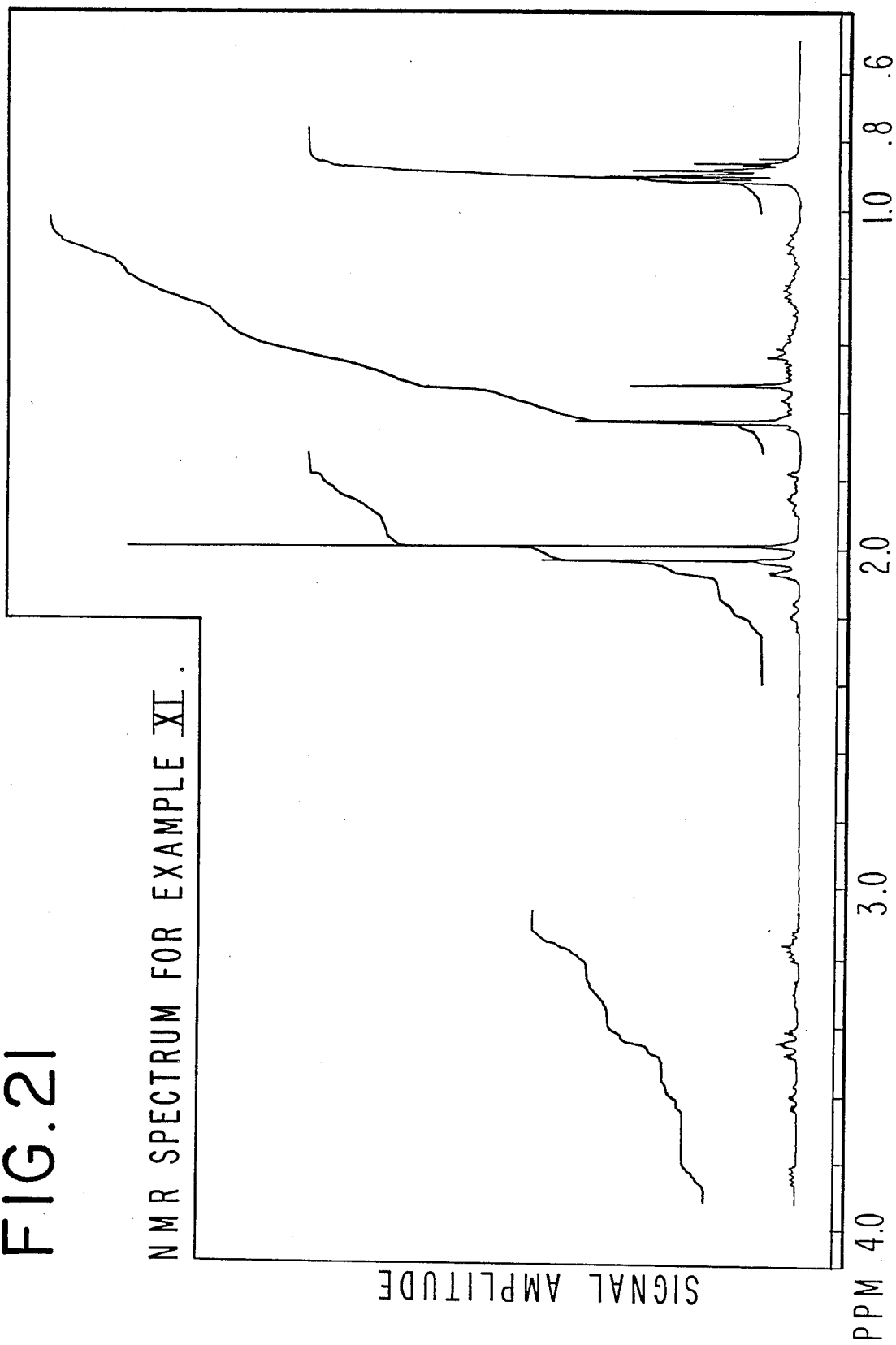

FIG. 21 is the NMR spectrum for the compound having the structure:

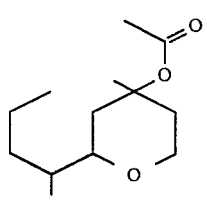

prepared according to Example XI.

Figure 22:
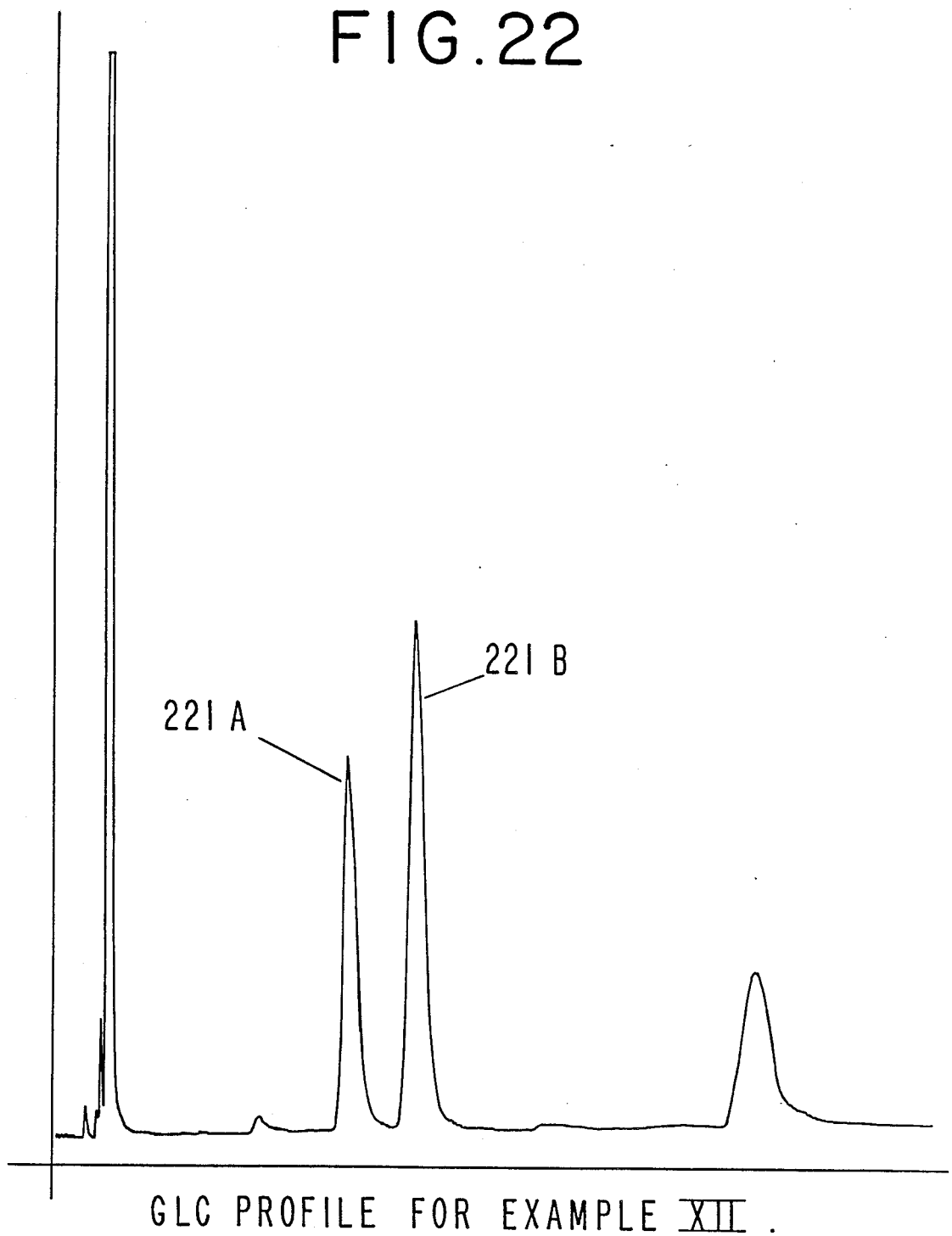

FIG. 22 is the GLC profile for the reaction product of Example XII containing the compound having the structure:

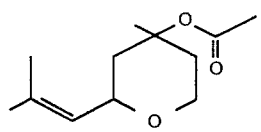

(Conditions: SE-30 column programmed at 180° C. isothermal).

Figure 23:
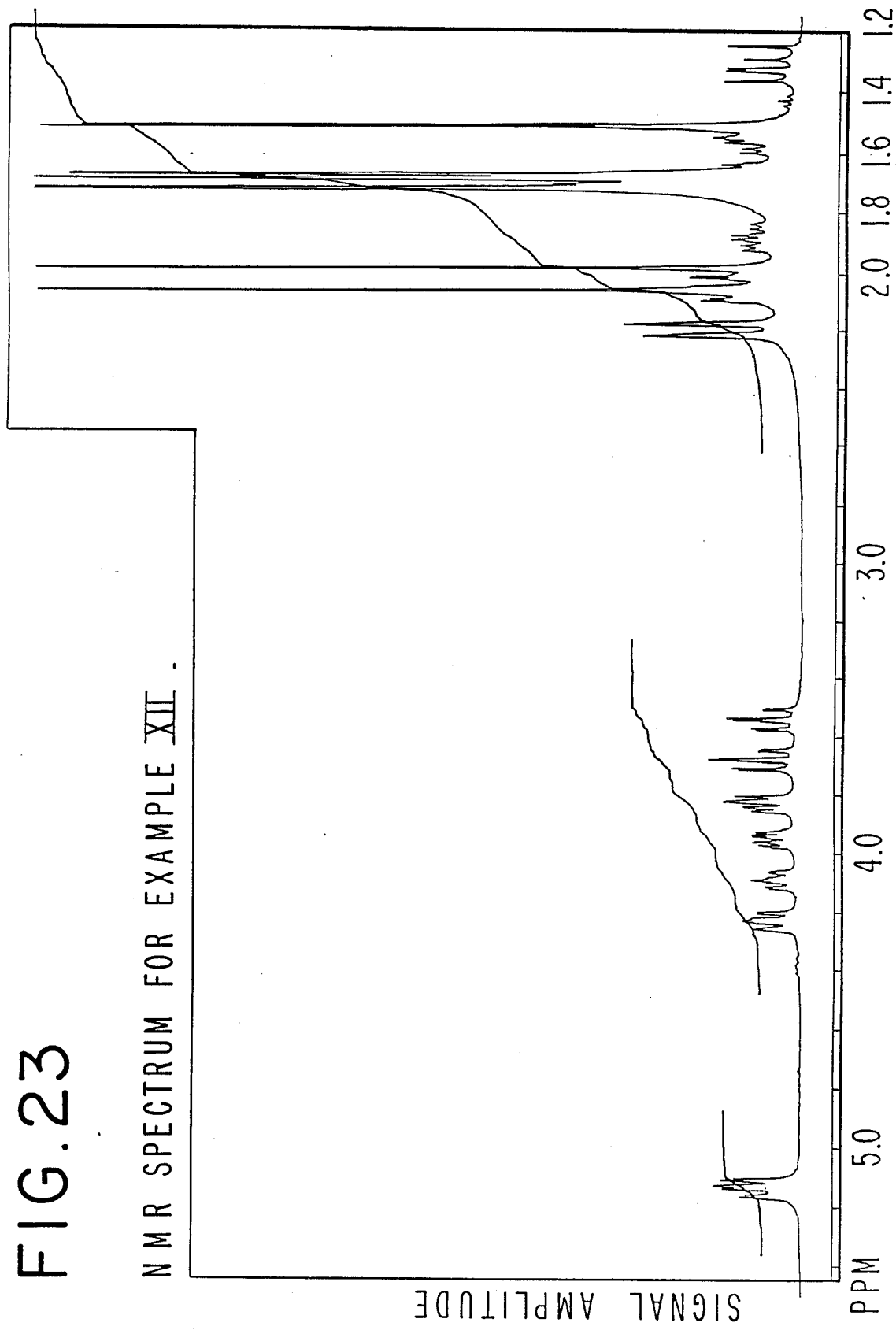

FIG. 23 is the NMR spectrum for the compound having the structure:

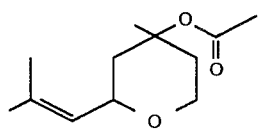

prepared according to Example XII.

Figure 24:
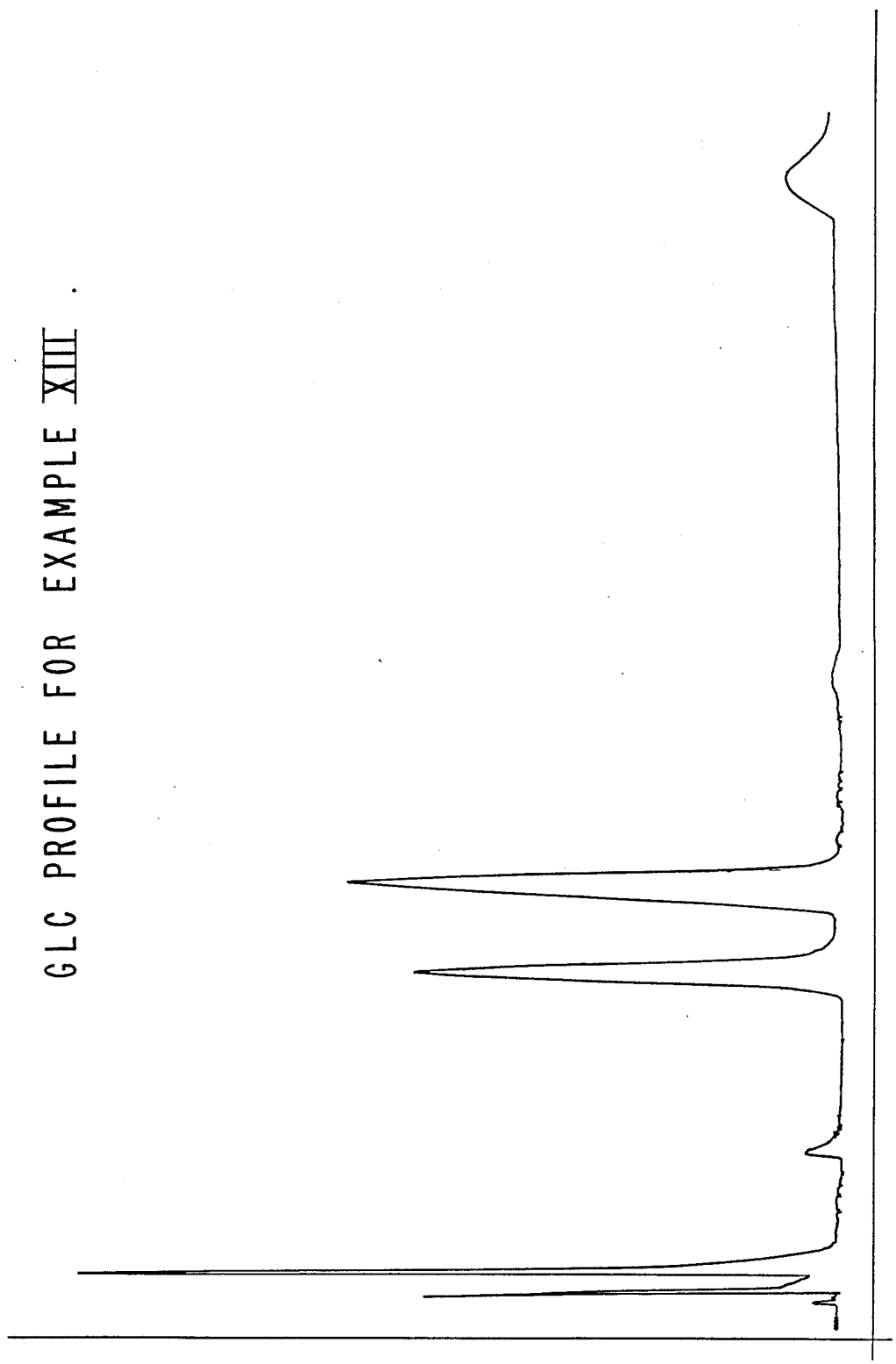

FIG. 24 is the GLC profile for the reaction product of Example XIII containing the compound having the structure:

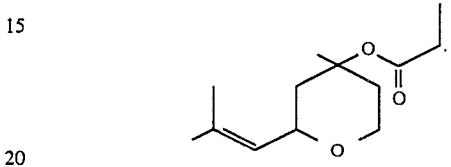

Figure 25:
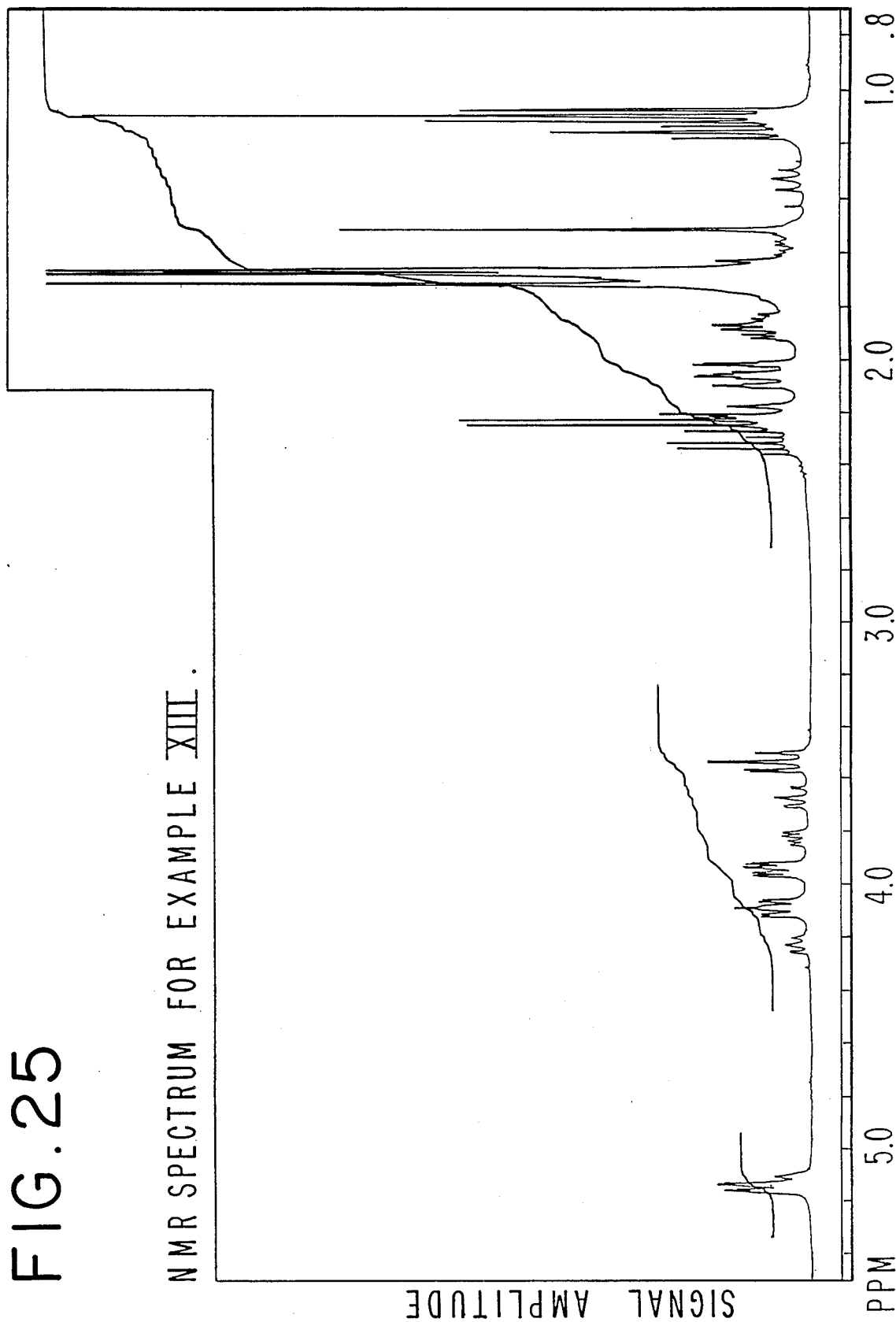

FIG. 25 is the NMR spectrum for the compound having the structure:

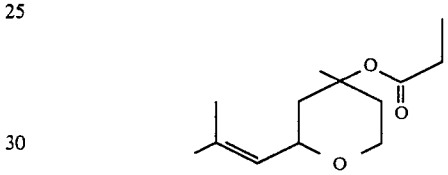

prepared according to Example XIII.

Figure 26:
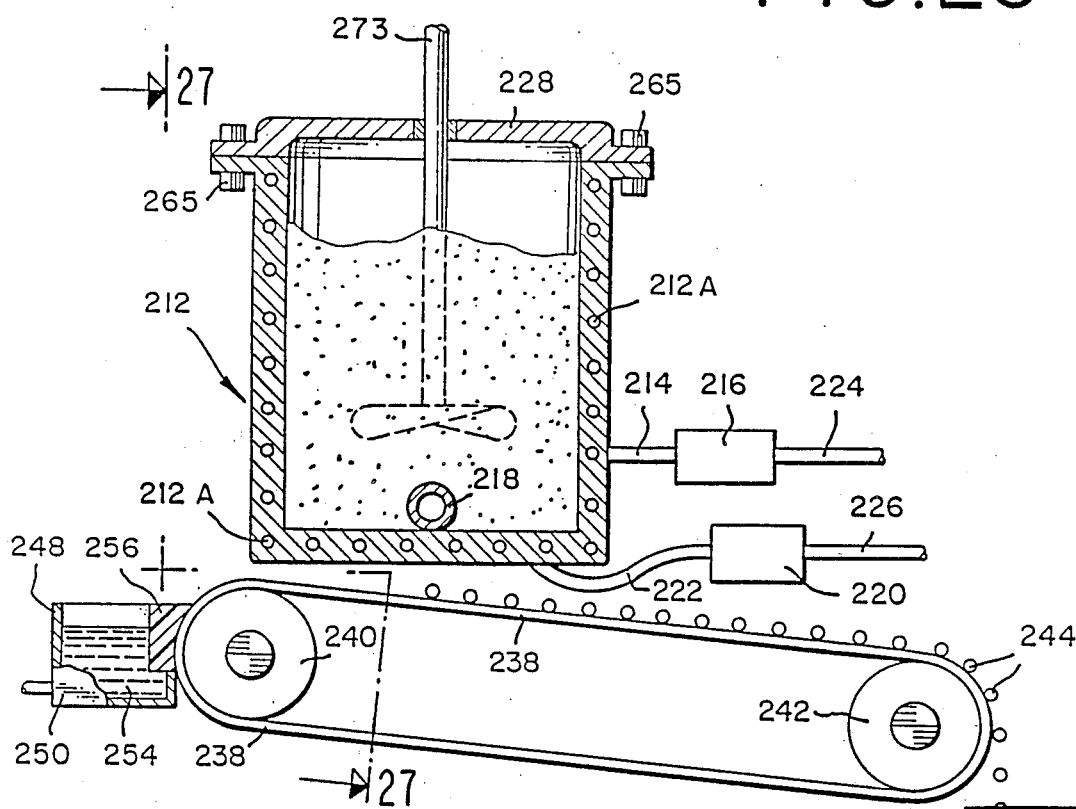

FIG. 26 represents a cut-away side elevation view of apparatus used in forming perfume polymers which contain imbedded therein at least one of the 2,4,4-trisubstituted tetrahydropyranol esters of our invention.

Figure 27:
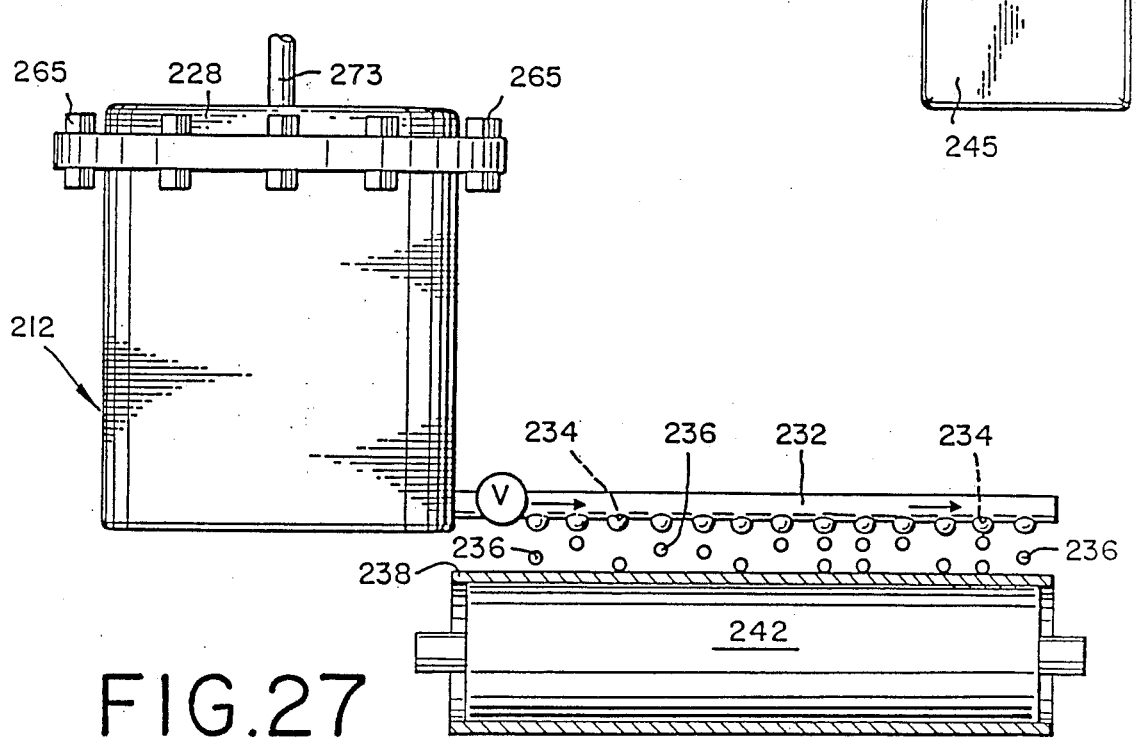

FIG. 27 is a front view of the apparatus of FIG. 26 looking in the direction of the arrows.

DETAILED DESCRIPTION OF THE DRAWINGS

Figure 1:
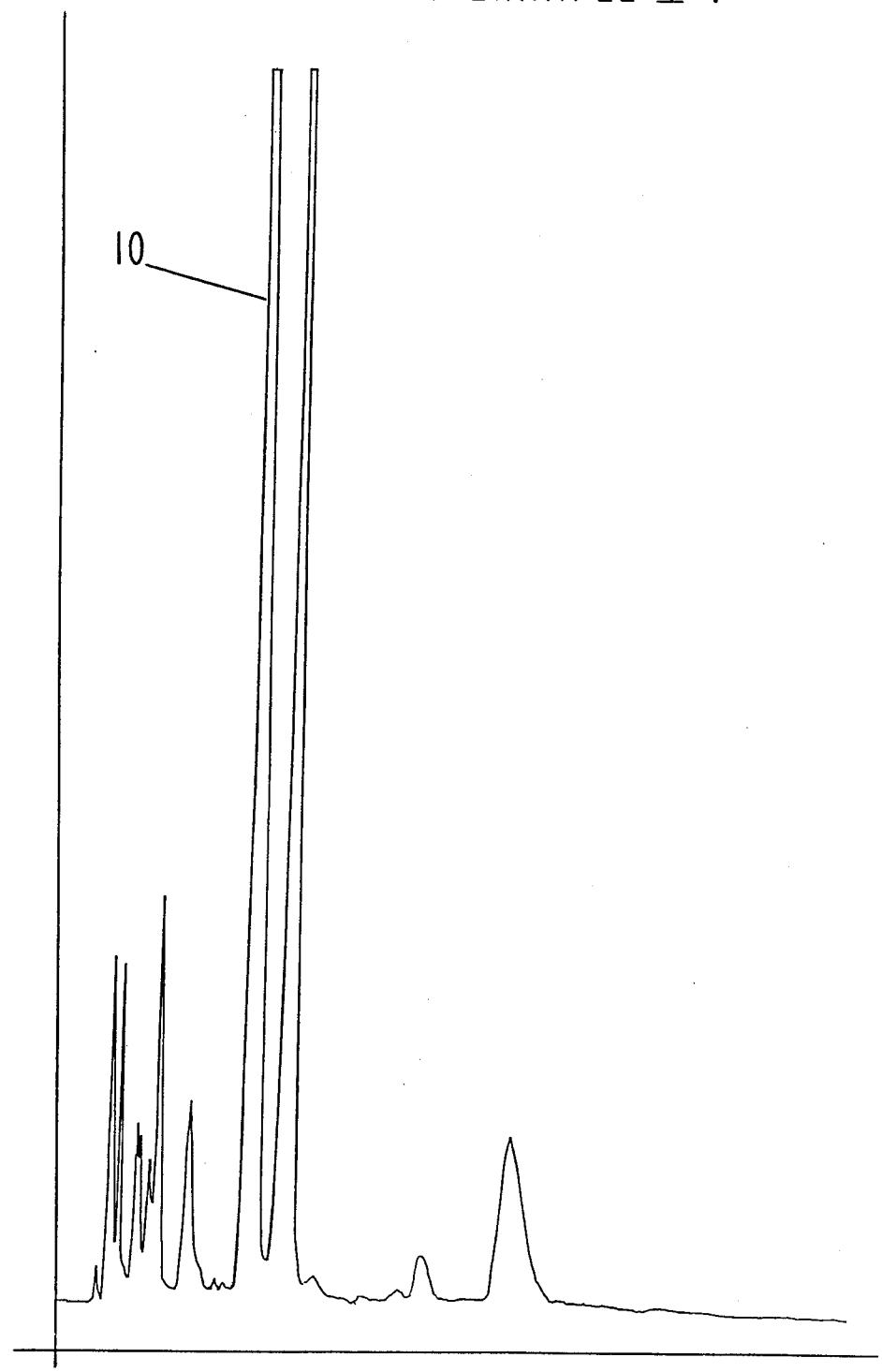
FIG. 1 is the GLC profile for the reaction product of Example I containing the compound having the structure.

FIG. 1 is the GLC profile for the reaction product of Example I containing the compound having the structure:

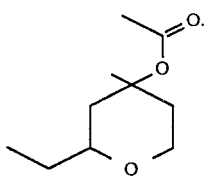

The peak indicated by reference numeral 10 is the peak for the compound having the structure:

(Conditions: SE-30 column programmed at 180° C. isothermal).

FIG. 3 is the GLC profile for the reaction product of Example II containing the compound having the structure:

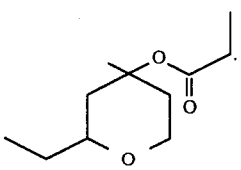

Peaks 30A and 30B are peaks for isomers of the compound having the structure:

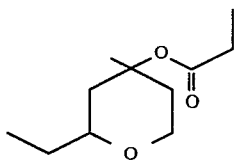

(Conditions: SE-30 column programmed at 180° C. isothermal).

FIG. 7 is the GLC profile for the reaction product of Example IV containing the compound having the structure:

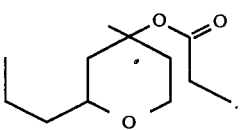

The peaks indicated by reference numerals 70A and 70B are peaks for isomers of the compound having the structure:

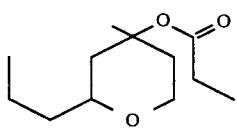

(Conditions: SE-30 column programmed at 180° C. isothermal).

FIG. 22 is the GLC profile for the reaction product of Example XII containing the compound having the structure:

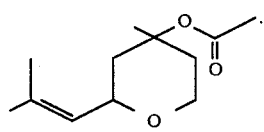

The peaks represented by the numbers 22A and 22B are peaks for isomers of the compound having the structure:

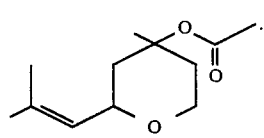

Referring to FIGS. 26 and 27, there is provided a process for forming scented polymer elements (wherein the polymer may be a thermoplastic polymer such as low density polyethylene or polypropylene or copolymers of ethylene and vinyl acetate or mixtures of polymers and copolymers such as copolymers of ethylene and vinyl acetate and polyethylene) such as pellets useful in the formation of plastic particles useful in fabricating certain articles which may be perfumed (and, further, which may be exposed to chlorine bleaches). This process comprises heating the polymer or mixture of polymers to the melting point of said polymer or mixture of polymers, e.g., 250° C. in the case of low density polyethylene. The lower most portion of the container is maintained at a slightly lower temperature and the material in the container is taken off at such location for delivery through the conduit. Thus, referring to FIGS. 26 and 27, in particular, the apparatus used in producing such elements comprises a device for forming the polymer containing the perfume, e.g., polyethylene or polyethylene-polyvinyl acetate or mixtures of same or polyproylene, which comprises a vat or container 212 into which the polymer taken alone or in admixture with other copolymers and the perfuming substance which is at least one of the 2,4,4-trisubstituted tetrahydro pyranyl esters of our invention and other compatible perfumes is placed. The container is closed by means of an air-tight lid 228 and clamped to the container by bolts 265. A stirrer 273 traverses the lid or cover 228 in an air-tight manner and is rotatable in a suitable manner. A surrounding cylinder 212A having heating coils which are supplied with electric current through cable 214 from a rheostat or control 216 is operated to maintain the temperature inside the container 212 such that the polymer in the container will be maintained in the molten or liquid state. In has been found advantageous to employ polymers at such a temperature that the viscosity will be in the range of 90-100 sayboldt seconds. The heater 218 is operated to maintain the upper portion of the container 212 within a temperature range of, for example 220°-270° C. in the case of low density polyethylene.

The bottom portion of the container 212 is heated by means of heating coils 212A regulated through the control 220 connected thereto through a connecting wire 222 to maintain the lower portion of the container 212 within a temperature range of 220°-270° C.

Thus, the polymeror mixture of polymers added to the container 212 is heated from 10-12 hours, whereafter the perfume composition or perfume material which contains one or more of the 2,4,4-trisubstituted tetrahydro pyranyl esters of our invention is quickly added to the melt. Generally, about 10-45 percent by weight of the resulting mixture of the perfumery substance is added to the polymer.

After the perfume material is added to the container 212, the mixture is stirred for a few minutes, for example, 5-15 minutes and maintained within the temperature ranges indicated previously by the heating coil 212A. The controls 216 and 220 are connected through cables 224 and 226 to a suitable supply of electric current for supplying the power for heating purposes.

Thereafter, the valve "V" is opened permitting the mass to flow outwardly through conduit 232 having a multiplicity of orifices 234 adjacent to the lower side thereof. The outer end of the conduit 232 is closed so that the liquid polymer in intimate admixture with one or more of the 2,4,4-trisubstituted tetrahydro pyranyl esters of our invention and one or more other substances, will continuously drop through the orifices 234 downwardly from the conduit 232. During this time, the temperature of the polymer intimately admixed with the perfumery substance in the container 212 is accurately controlled so that a temperature in the range of from about 240°-250° C., for example, (in the case of low density polyethylene) will exist in the conduit 232. The regulation of the temperature through the controls 216 and 220 is essential in order to insure temperature balance to provide for the continuous dripping or dropping of molten polymer intimately admixed with the perfume substance which is all of or which contains one or more of the 2,4,4-trisubstituted tetrahydro pyranyl esters of our invention, through the orifices 234 at a rate of which will insure the formation of droplets 236 which will fall downwardly onto a moving conveyor belt 238 caused to run between conveyor wheels 240 and 242 beneath the conduit 232.

When the droplets 236 fall onto the conveyor 238, they form pellets 244 which harden almost instantaneously and fall off the end of the conveyor 238 into a container 250 which is advantageously filled with water or some other suitable cooling liquid to insure the rapid cooling of each of the pellets 244. The pellets 244 are then collected from the container 250 and utilized for the formation of functional products, e.g., garbage bags and the like.

THE INVENTION

The present invention provides 2,4,4-trisubstituted tetrahydro pyranyl esters defined according to the generic structure:

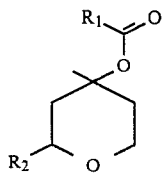

wherein $R_1$ represents methyl or ethyl and $R_2$ represents $C_2$-$C_4$ straight or branched chain alkyl or alkenyl.

The 2,4,4-trisubstituted tetrahydro pyranyl esters of our invention produced according to the process steps, to wit:

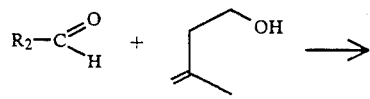

and

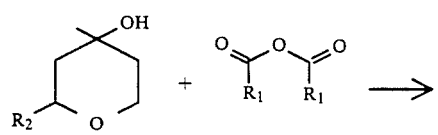

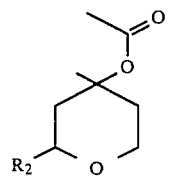

wherein $R_1$ and $R_2$ are defined, supra are capable of augmenting or enhancing fruity, citrusy, grapefruit, green, herbaceous, chamomile, floral, lily, rose, muguet, live flower petal-like, sauge sclaree, tobacco, mentha citrata, lavender, witch hazel, woody, orris, earthy, early morning forest path, oolong tea, ozoney, natural waxey, piney, guiacwood-like, sweet, jasmine and geranium aromas with chamomile, woody, soft woody, cabreuva, sauge sclaree, lavender, winey, floral, rose, copaiba oil-like, geranium, earthy, early morning forest path, fatty, oatmeal, herbaceous, spicy and black pepper undertones in perfume compositions, colognes and perfumed articles including soaps, bleaches, anionic, cationic, nonionic or zwitterionic detergents, fabric softener articles and perfumed articles.

The 2,4,4-trisubstituted tetrahydro pyranyl esters of our invention are produced by first forming compounds defined according to the structure:

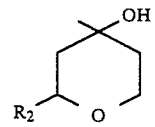

by reacting an aldehyde defined according to the structure:

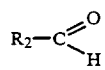

with an alcohol defined according to the structure:

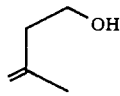

according to the reaction:

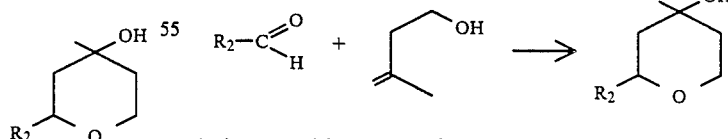

(using conditions as set forth in the prior art, for example, conditions set forth in U.S.S.R. Pat. No. 620,487; and in the presence of an acid catalyst such as an inorganic acid or an acid anion exchange catalyst or phosphoric acid or sulfuric acid at a temperature in the range of from about 50° up to about 60° C. Examples of such reactions in the prior art to form compounds useful in perfumery are as follows:

(a) the reaction:

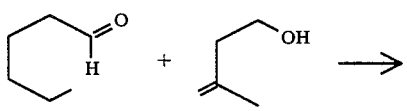

set forth in U.S.S.R. Pat. No. 620,487;
(b) the reaction:

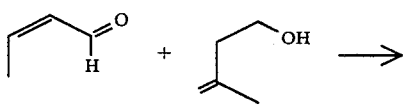

set forth in U.S.S.R. Pat. No. 638,597.

The resulting compound defined according to the structure:

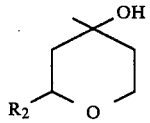

is then reacted with an acyl anhydride according to the reaction:

using a mineral acid catalyst (e.g., phosphoric acid or sulphuric acid), a Lewis acid catalyst such as aluminum trichloride, diethyl aluminum chloride, dialuminum ethyl chloride, stannis chloride and the like or an alkane sulphonic acid such as para toluene sulphonic acid or methane sulphonic acid at a temperature in the range of from about 0° C. up to about 120° C. In place of acyl anhydrides, acyl halides such as acetyl chloride and acetyl bromide may be used as the acylation agent.

At the end of the reaction, the reaction product is cooled and the reaction mass is then "worked up" as by washing and the organoic phase is distilled by means of, for example, fractional distillations.

Specific examples of the 2,4,4-trisubstituted tetrahydro pyranyl esters produced according to the foregoing process and useful in the practice of our invention and one 2,4,4-trisubstituted tetrahydro pyranyl esters not so useful are set forth in Table I below:

TABLE I

| Structure of Compound | Perfumery Evaluation |
|---|---|
| The compound having the structure: | A fruity, green, chamomile and rose aroma profile. |

TABLE I-continued

| Structure of Compound | Perfumery Evaluation |
|---|---|
| prepared according to Example I, bulked distillation fractions 5-9. The compound having the structure: | A fruity and chamomile aroma profile. |
| prepared according to Example II, bulked fractions 7-12. The compound having the structure: | A sauge sclaree, tobacco-like, mentha citrata, lavender, and witch hazel aroma profile with chamomile, rose, woody, sauge sclaree, lavender and winey undertones. |
| prepared according to Example III, bulked fractions 7-11. The compound having the structure: | A woody, live flower petal-like and green aroma with floral (rose) and woody copabia oil-like undertones. |
| produced according to Example IV, bulked fractions 7-11. The compound having the structure: | An orris, earthy (early morning forest path), oolong tea-like aroma with earthy (early morning forest path) undertones. |
| prepared according to Example V, bulked fractions 7-15. The compound having the structure: | A floral (rose), fruity, green, piney and woody aroma profile. |
| prepared according | |

TABLE I-continued

| Structure of Compound | Perfumery Evaluation |
|---|---|
| to Example VI, bulked distillation fractions 7-18. The compound having the structure: (structure) prepared according to Example VII, bulked fractions 4-11. | A ozoney and woody aroma profile. |
| The compound having the structure: (structure) produced according to Example VIII, bulked fractions 6-11. | A natural waxey aroma with fatty undertones. |
| The compound having the structure: (structure) prepared according to Example IX, bulked fractions 11-17. | A guiacwood-like and floral (rose) aroma profile. |
| The compound having the structure: profile with soft woody (structure) produced according to Example X, bulked fractions 6-14. | A sweet and jasmine aroma (cabreuva) undertones. |
| The compound having the structure: (structure) produced according to Example XI, bulked fractions 3-11 (outside of the scope of our invention). The compound having the structure: | A non-descript aroma.<br><br>A fruity, citrusy, green, rose (geranium) and piney aroma |

TABLE I-continued

| Structure of Compound | Perfumery Evaluation |
|---|---|
| (structure) produced according to Example XII, bulked fractions 5-10. | profile with floral (geranium) oatmeal and herbaceous undertones. |
| The compound having the structure: (structure) produced according to Example XIII. | A green, floral (rose/muguet), lily, herbaceous and citrusy (grapefruit) aroma profile with floral, rose, spicy and black pepper undertones. |

The 2,4,4-trisubstituted tetrahydro pyranyl esters of our invention and one or more auxiliary perfume ingredients including, for example, hydrocarbons, alcohols, ketones, aldehydes, nitriles, esters other than the 2,4,4-trisubstituted tetrahydro pyranyl esters of our invention, lactones, ethers, hydrocarbons, synthetic essential oils and natural essential oils may be admixed so that the combined odors of the individual components produce a pleasant and desired fragrance, particularly and preferably in the citrusy and/or green and/or woody and/or piney and/or earthy fragrances.

Such perfume compositions usually contain (a) the main note or the "bouquet" or foundation stone of the composition; (b) modifiers which round off and accompany the main note; (c) fixatives which include odorous substances which lead a particular note to the perfume throughout all stages of evaporation and substances which retard evaporation; and (d) topnotes which are usually low boiling fresh smelling materials.

In perfume compositions, it is the individual components which contribute to their particular olfactory characteristics; however the overall sensory effect of the perfume composition will be at least the sum total of the effects of each of the ingredients. Thus, one or more of the 2,4,4-trisubstituted tetrahydro pyranyl esters of our invention can be used to alter, modify or enhance the aroma characteristics of a perfume composition, for example, by utilizing or moderating the olfactory reaction contributed by another ingredient in the composition.

The amount of the 2,4,4-trisubstituted tetrahydro pyranyl ester of our invention which will be effective in perfume compositions as well as in perfumed articles and colognes depends upon many factors, including the other ingredients, their amounts and the effects which are desired. It has been found that perfume compositions containing as little as 0.005% of the 2,4,4-trisubstituted tetrahydro pyranyl ester of our invention or even less (e.g., 0.002%) can be used to impart, augment or enhance fruity, citrusy, grapefruit, green, herbaceous, chamomile, floral, lily, rose, muguet, live flower petal-like, sauge sclaree, tobacco, mentha citrata, lavender, witch hazel, woody, orris, earthy, early morning forest path, oolong tea, ozoney, natural waxey, piney, guiacwood-like, sweet, jasmine and geranium aroma nuances with chamomile, woody, soft woody, cabreuva, sauge sclaree, lavender, winey, floral, rose, copaiba oil-like, earthy, early morning forest path, fatty, oatmeal, herbaceous, spicy and black pepper undertones to soaps, cosmetics, detergents (including anionic, cationic, nonionic or zwitterionic solid or liquid detergents) or other products. The amount employed can range up to 70% of the fragrance components and will depend upon considerations of cost, nature of the end product, the effect desired on the finished product and the particular fragrance sought.

The 2,4,4-trisubstituted tetrahydro pyranyl esters of our invention are useful (taken alone or together with other ingredients in perfume compositions) in detergents and soaps, space odorants, perfumes, colognes, toilet water, bath preparations such as lacquers, brilliantines, pomades and shampoos; cosmetic preparations, such as creams, deodorants, hand lotions and sun screens; powders such as talcs, dusting powders, face powders and the like. As little as 0.25% of the 2,4,4-trisubstituted tetrahydro pyranyl esters of our invention will suffice to impart an intense fruity, citrusy, grapefruit, green, herbaceous, chamomile, floral, lily, rose, muguet, live flower petal-like, sauge sclaree, tobacco, mentha citrata, lavender, witch hazel, woody, orris, earthy, early morning forest path, oolong tea, ozoney, natural waxey, piney, guiacwood-like, sweet, jasmine and geranium aroma notes with chamomile, woody, soft woody, cabreuva, sauge sclaree, lavender, winey, floral, rose, copaiba oil-like, geranium, earthy, earthy morning forest path, fatty, oatmeal, herbaceous, spicy and black pepper undertones to citrusy, woody, floral, herbaceous and earthy perfume formulations. Generally, no more than 5% of the 2,4,4-trisubstituted tetrahydro pyranyl esters of our invention based on the ultimate end product is required to be used as is or in perfume compositions.

Furthermore, as little as 0.25% of the 2,4,4-trisubstituted tetrahydro pyranyl esters of our invention will suffice to impart such aroma to perfumed articles per se, whether in the presence of other perfume materials or whether used by itself. Thus, the range of use of the 2,4,4-trisubstituted tetrahydro pyranyl esters of our invention in perfumed articles may vary from about 0.25% up to about 5% by weight based on the total weight of the perfumed article.

In addition, the perfume composition or fragrance composition of our invention can contain a vehicle or carrier for the 2,4,4-trisubstituted tetrahydro pyranyl esters of our invention. The vehicle can be a liquid such as a non-toxic alcohol, e.g., ethanol, a non-toxic glycol, e.g., propylene glycol or the like. The carrier can also be an absorbent solid, such as a gum (e.g., gum arabic), or components for encapsulating the composition by means of coacervation (such as gelatin).

It will thus be apparent that the 2,4,4-trisubstituted tetrahydro pyranyl esters of our invention can be utilized to alter, modify or enhance aroma of perfume compositions, colognes or perfumed articles.

Furthermore, several processes may be used in order to produce a thickened, highly viscous hypochlorite bleaching or sterilizing solution whereby the desired aroma profiles are imparted to the articles treated with said hypochlorite solutions.

Thus, for example, the 2,4,4-trisubstituted tetrahydro pyranyl esters of our invention may be premixed with the diphenyl oxide derivative or diphenyl oxide derivative-amine oxide solubilizer-stabilizer (having the structures, respectively:

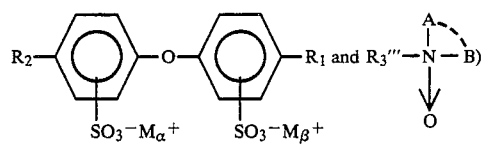

and the resulting 2,4,4-trisubstituted tetrahydro pyranyl esters/diphenyl oxide derivative or 2,4,4-trisubstituted tetrahydro pyranyl esters-diphenyl oxide derivative-amine oxide premix is then mixed with the hypochlorite bleaching or sterilizing solution with stirring. Immediately after such addition, an aqueous alkali metal hydroxide solution is added to the mixture to bring the pH to the range of 11–14.0. A pH of less than 11 is not desired since it is difficult to achieve a single phase stable system at low pH's. A pH higher than 14.0 will also create a system which (1) is unnecessarily corrosive; (2) will narrow the range of perfume oils useable (in conjunction with the 2,4,4-trisubstituted tetrahydro pyranyl esters) of the system and (3) will limit the particular ingredients useable in such perfume oils in conjunction with the 2,4,4-trisubstituted tetrahydro pyranyl esters. On the other hand, if for example, the 2,4,4-trisubstituted tetrahydro pyranyl esters is used alone or further in combination with (i) diisoamylene epoxides; (ii) diisoamylenes as described in application for U.S. Pat. Ser. No. 188,576 filed on Oct. 9, 1980; or (iii) acyl diisoamylene derivatives described in application for U.S. Pat. Ser. No. 184,132 filed on Sept. 4, 1980 and/or (iv) ketal derivatives of acyl diisoamylene derivatives described in application for U.S. Pat. Ser. No. 212,993 filed on Dec. 4, 1980, a pH of about 14.0 and even slightly higher (e.g., 14.1) is acceptable.

The aqueous alkali metal hydroxide can be added to the aqueous alkali metal hypochlorite solution before adding the diphenyl oxide derivatives (taken alone or in conjunction with the amine oxide) or the 2,4,4-trisubstituted tetrahydro pyranyl esters or mixtures of 2,4,4-trisubstituted tetrahydro pyranyl esters with other materials such as diisoamylene epoxides. Indeed, the ingredients: the 2,4,4-trisubstituted tetrahydro pyranyl esters; the alkali metal hydroxide ad the diphenyl oxide derivative or diphenyl oxide derivative-amine oxide composition (having the structures, respectively:

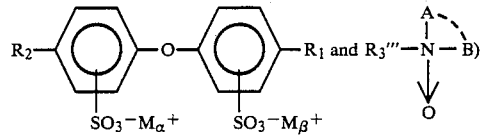

may be added or admixed in any order which is convenient to the formulator. One desirable process involves first forming the diphenyl oxide derivative or diphenyl oxide derivative-amine oxide composition-2,4,4-trisubstituted tetrahydro pyranyl esters "premix", mixing the premix with the alkali metal hypochlorite solution and finally adjusting the pH of the solution with alkali metal hydroxide to bring the pH to within the range of 11–14.0. A second, more preferable process, involves first adjusting the pH of the aqueous alkali metal hypochlorite solution to 11–14.0 and then admixing the solution with the aforedescribed "premix".

The alkali metal hypochlorites preferred in the practice of our invention are: sodium hypochlorite, potassium hypochlorite and lithium hypochlorite or mixtures of same. The alkali metal hypochlorites preferred in the practice of this invention are: lithium hydroxide, potassium hydroxide and sodium hydroxide, or, if desired, mixtures of such hydroxides.

The temperature at which the composition of our invention remains both substantially stable and commercially useful for the purpose set forth herein (that is, remains as a clear single aqueous or gel phase) and retains (1) the desired properties inherent in the known bleaching and sterilizing uses of aqueous alkali metal hypochlorite liquid or gel solutions, and (2) the properties imparted thereto as a result of the use of the 2,4,4-trisubstituted tetrahydro pyranyl esters which impart to articles previously subjected to the aqueous alkali metal hypochlorite gel or liquid solutions a desired aroma profile, varies from approximately 20° F. up to approximately 120° F. At temperatures below 20° F. the bleaching or sterilizing efficiency of the compositions of our inventions is diminished at an excessive rate.

When it is desired to (1) initially form the $C_{10}$–$C_{12}$ straight chain or branched chain diphenyl oxide alkali metal sulfonate or diphenyl oxide derivative-amine oxide-2,4,4-trisubstituted tetrahydro pyranyl ester premix; (2) then combine the resulting premix with an alkali metal hypochorite solution; (3) then add the thickening agent and then (4) adjust the pH of the resulting solution to the range of 11–14.0, then the temperature of mixing ranges are considered to be within the scope of this invention as follows:

| | | |
|---|---|---|
| (a) | Formation of the diphenyl oxide derivative or diphenyl oxide-amine oxide-2,4,4-trisubstituted tetrahydro pyranyl esters premix | 20° F.–150° F. |
| (b) | Mixing the premix with aqueous metal alkali hypochlorite solution followed by thickening agent | 20° F.–120° F. |
| (c) | Adjustment of pH of the solution to the range of 11–14.0 using aqueous alkali metal hydroxide solution. | 20° F.–120° F. |

In any event, wherever a mixing unit operation involves the aqueous alkali metal hypochlorite solution, the temperature of mixing is limited to the range of 20° F.–120° F. Where the mixing unit operation involves the mixing of 2,4,4-trisubstituted tetrahydro pyranyl esters, the upper bound of the temperature range is limited by the stability of the 2,4,4-trisubstituted tetrahydro pyranyl esters or other perfume ingredient mixed with the 2,4,4- trisubstituted tetrahydro pyranyl esters useable in the practice of our invention; and the lower bound of said temperature range is limited by the least temperature where a single liquid phase or gel phase including the 2,4,4-trisubstituted tetrahydro pyranyl esters or other ingredient admixed therewith will exist. Where a unit mixing operation of the process of our invention involves the mixing of one or more diphenyl derivatives having the generic structure:

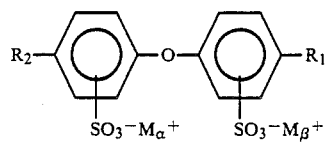

taken alone or taken together with one or more amine oxides having the generic structure:

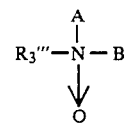

with other materials, the upper bound of the temperature range is the decomposition point of any one of the diphenyl oxide derivatives of amine oxide components and the lower bound is the least temperature where a single liquid phase or gel phase, including the diphenyl oxide derivatives or diphenyl oxide-amine mixture will exist.

Preferred diphenyl oxide derivative compositions from a practical standpoint useful in the practice of our invention are compounds having the structure:

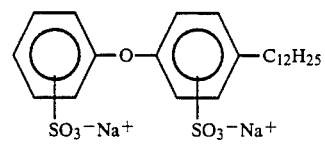

where the $C_{12}H_{25}$ moiety represents one or a series of different branched chains; compounds defined according to the structure:

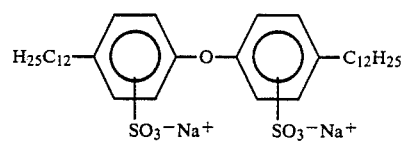

where the $C_{12}H_{25}$ moiety represents one or a series of different branched chains; compounds defined according to the structure:

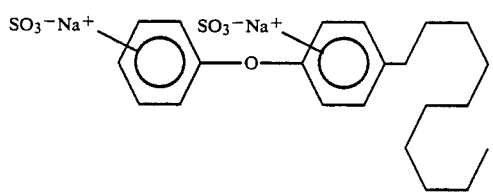

and compounds defined according to the structure:

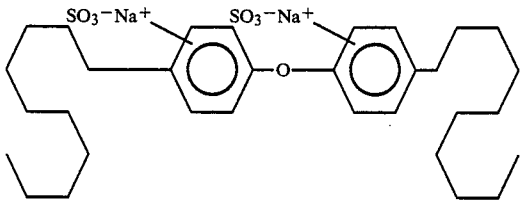

otherwise known as DOWFAX®2A1 in the case where one or $R_1$ or $R_2$ represents branched $C_{12}H_{25}$ alkyl chains and the other of $R_1$ or $R_2$ represents hydrogen, or DOWFAX®3B2 in the case where one of $R_1$ or $R_2$ represents straight $C_{10}$ alkyl chain and the other of $R_1$ or $R_2$ represents hydrogen (DOWFAX® being a registered trademark of the Dow Chemical Company of Midland, Mich.

When used in conjunction with the diphenyl oxide derivatives preferred amine oxide compositions, from a practical standpoint, useful in the practice of our invention are the commercially available (1) dimethyl "cocoamine" oxide (a mixture which is dominated by dimethyl-$C_{12}$–$C_{16}$ straight chain alkyl amine oxides: more particularly a mixture containing approximately 70% $C_{12}$ straight chain alkyl amines oxides, approximately 25% of straight chain $C_{14}$ alkyl amine oxides and approximately 4% straight chain $C_{16}$ alkyl amine oxides) and (2) N-cocomorpholine oxide, a mixture dominated by straight chain $C_{12}$–$C_{16}$ alkyl morpholine oxides (specifically containing approximately 70% straight chain $C_{12}$ alkyl morpholine oxide, approximately 25% straight chain $C_{14}$ alkyl morpholine oxide, and approximately 4% straight chain $C_{16}$ alkyl morpholine oxide). Commercial examples of such amine oxide compositions are: AROMOX® DMC-W and AROMOX® DMMC-W which are 30% aqueous dimethyl cocoamine oxide solutions and AROMOX® NCMDW which is a 40% aqueous N-cocomorpholine oxide solution each of which is produced by the Armac Division of AKZO of Chicago, Ill. These materials are described in Brochure 68011, published by Armous Industrial Chemicals, P.O. Box s1805, Chicago, Ill. 60690. Other preferred amine oxides are n-undecyl dimethyl amine oxide and n-tridecyl dimethyl amine oxide.

The percentage of hypochlorite ion in the compositions of our invention may vary from about 1% up to about 20% for the desired effects to be produced using the diphenyl oxide derivative or diphenyl oxide derivative-amine-oxide 2,4,4-trisubstituted tetrahydro pyranyl esters compositions covered by our invention. The usual percent of alkali metal hypochlorite in solution is about 5%, the percentage of sodium hypochlorite in such mixtures as CLOROX® the registered trademark of the Clorox Corporation.

The perfume oil used in conjunction with the 2,4,4-trisubstituted tetrahydro pyranyl esters which, in turn, is used in conjunction with the aqueous alkali metal hypochlorite solution must have such properties as to be able (1) to be compatible with the 2,4,4-trisubstituted tetrahydro pyranyl esters of our invention; (2) to impart to the resulting or "aqueous alkali metal hypochlorite" liquid or gel solution a pleasing aroma which harmonizes with the aroma of the 2,4,4-trisubstituted tetrahydro pyranyl esters (3) to effect a substantial diminution or elimination of the disagreeable "hypochlorite" aroma which is imparted to surfaces (e.g., bleached laundry or the hands of the user which are in direct contact with the hypochlorite solution) on which known aqueous alkali metal hypochlorite solutions have been used; and (4) to impart to the surfaces with which such aqueous alkali metal hypochlorite solutions are in contact, a pleasant long lasting stable aroma. Examples of ingredients compatible with 2,4,4-trisubstituted tetrahydro pyranyl esters and suitable for the aforementioned purposes, that is, useable in conjunction with the hypochorites, amine oxide derivatives and diphenyl oxide derivatives of our invention are as follows:

1. Cedryl alkyl ethers covered by U.S. Pat. No. 3,373,208 such as cedryl methyl ether;
2. Isochroman musks covered by U.S. Pat. Nos. 3,360,530 and 3,591,528 such as 6-oxa-1,1,3,3,8-pentamethyl-2,3,5,6,7,8-hexahydro-1H-benz(1)indene;
3. Polycyclic ethers covered by U.S. Pat. No. 3,281,432, such as octahydro-1,3a-6-trimethyl-1H-1,6a, ethanopentaleno-(1,2-C)furan;
4. Polycyclic ketones such as hexahydro-1,1,5,5-tetramethyl-2H-2H-2,4a-methanonaphthalen-8-(5H)one;
5. Diisoamylenes described according to application for U.S. Letters Patent, Ser. No. 188.576 filed on Sept. 18, 1980;
6. Acyldiisoamylene derivatives described according to application for U.S. Letters Patent Ser. No. 184,132 filed on Sept. 4, 1980 and ketal derivatives thereof described according to application for U.S. Letters Patent, Ser. No. 212,993 filed on Dec. 4, 1980; and
7. Diisoamylene epoxide derivatives according to application for U.S. Letters Patent, Ser. No. 231,773 filed on Feb. 27, 1981.

It will be understood that a number of materials which impart to the citrusy or floral aromas of certain of the 2,4,4-trisubstituted tetrahydro pyranyl esters of our invention additional eucalyptol-like, or minty or woody nuances will not be useful for the practice of that aspect of our invention concerning perfumed hypochlorite bleaches because they are, intralia, easily oxidized by the alkali metal hypochlorite in the system. Examples are 1,5,9-trimethyl-12-acetyl-cyclododecatriene-1,5,8 and 1,5,9-trimethyl-12-cyclodeadiene-1.8 covered by British Pat. No. 1,204,409.

A basic feature of our invention concerns the fact that the only detergent group needed or desirable in the composition of our invention is the class of diphenyl oxide derivatives defined according to the structure:

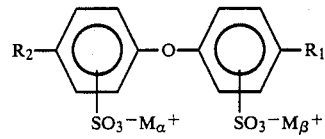

wherein $R_1$, $R_2$, M and M are defined, supra, taken alone or in conjunction with the class of morpholino and/or dimethyl $C_{11}$–$C_{13}$ straight chain alkyl amine oxides defined according to the structure:

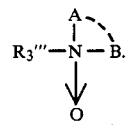

More specifically, such detergents as sodium decyl ether sulfate, sodium myristyl ether sulfate, sodium lauryl ether sulfate and lithium lauryl ether sulfate are neither desired nor are they required. Furthermore, the well known hydrotropes employed in prior art compositions such as the well known familys of clarifying agents comprising the alkali metal or alkali earth metal salts of mono- and polyalkylated benzene or naphthalene sulfonates such as sodium xylene or magnesium toluene sulfonate are again neither desired nor are they required in the composition intended to be encompassed by the instant invention.

Another basic feature of our invention concerns the fact that when it is desired to have a gel phase composition, thickener agents may be employed in conjunction with the system; hydpochlorite bleach-2,4,4-trisubstituted tetrahydro pyranyl esters-diphenyl oxide derivative or plain oxide-derivative-amine oxide derivative (having the general structure)

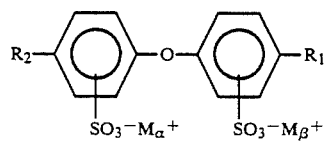

and having the structure:

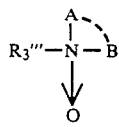

of our invention.

Still another basic feature of our invention concerns the fact that the gel phase compositions including thickener agents are employed with the "premix" system; 2,4,4-trisubstituted tetrahydro pyranyl esters-diphenyl oxide derivative or diphenyl oxide derivative-amine oxide of our invention.

Thus, sodium palmitate, sodium stearate, sodium laurate, potassium palmitate, potassium stearate, potassium laurate, lithium palmitate, lithium stearate and/or lithium laurate or combinations of the foregoing may be added to the compositions of matter of our invention to provide a thickened gel-type hypochlorite bleach which is, in addition to being a semi-solid state, is unobviously, advantageously and unexpectedly stable over long period of time. Percentages of thickening agents such as sodium palmitate, sodium stearate, sodium laurate, potassium palmitate, potassium stearate, potassium laurate, lithium palmitate, lithium stearate or lithium laurate or combinations of these which may be used in the thickened compositions of our invention are from 1% by weight up to 12% by weight of the thickener based on the overall weight of hypochlorite bleach-diphenyl oxide-derivative (or diphenyl oxide derivative-amine oxide)2,4,4-trisubstituted tetrahydro pyranyl esters composition of our invention. When it is merely desired to have a thickened "premix" the percentage of thickening agent may vary from about 5% up to about 40% by weight of thickener based on overall weight of "premix".

The following Examples I-XII and XIII serve to illustrate processes for producing the 2,4,4-trisubstituted tetrahydro pyranyl esters of our invention. Example XI serves to illustrate a process for producing the compound having the structure:

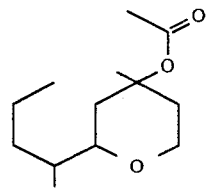

which has a non-descript aroma profile and which is not within the scope of our invention, accordingly. Examples XIV and examples following, in general, serve to illustrate organoleptic utilities of the 2,4,4-trisubstituted tetrahydro pyranyl esters of our invention.

In general, the following examples serve to illustrate specific embodiments of our invention (except for Example XI). It will be understood that these examples are illustrative and that the invention is to be connected restricted thereto only as indicated in the appended claims. All parts and percentages given herewith are by weight unless otherwise specified.

The following table illustrates the organoleptic properties of the precursor alcohols of the prior art compounds used in producing the 2,4,4-trisubstituted tetrahydro pyranyl esters of our invention.

TABLE II

| Prior Art Compound Structure | Organoliptic Utilities |
|---|---|
| The compound having the structure: ![structure] produced according to U.S.S.R. Patent No. 620,487 of July 17, 1987 the specification for which is incorporated by reference herein (abstracted at Chem. Abstracts, Volume 89, No. 185929p). | A nasturtium aroma profile. |
| The compound having the structure: ![structure] produced according to Example I. | A nerol, caramel, methacrylate chamomile aroma with a non descript undertone. |
| The compound having the structure: ![structure] produced according to Example VII. | A floral (muguet), spicy (nutmeg) aroma profile with a weak muguet topnote. |
| The compound having the structure: | A terpenic, flat, floral (muguet) aroma profile with |

TABLE II-continued

| Prior Art Compound Structure | Organoliptic Utilities |
|---|---|
| 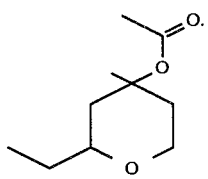 | with floral (muguet/freesia) undertones. |
| The compound having the structure:<br>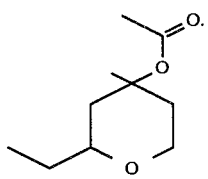  purchased under the name "FLORAL ®" from the Firmenich, et c S.A. of Geneva, Switzerland. | A sweet, muguet, green aroma with floral (muguet) topnotes. |

EXAMPLE I

PREPARATION OF 2-ETHYL-4-METHYL TETRAHYDRO PYRANYL ACETATE

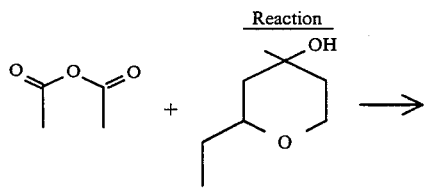

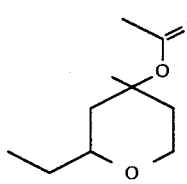

Into a 1 liter reaction flask equipped with stirrer, thermometer, reflux condenser, addition funnel and cooling bath are placed 204 grams of acetic anhydride and 4 grams of 75% methane sulfonic acid. With stirring, over a period of 45 minutes, 250 grams of 2-ethyl-4-methyl tetrahyro pyranyl is added. The reaction mass is heated with stirring to a temperature of 60° C. and maintained at 60° C. for a period of one hour. At the end of the one hour period, the reaction mass is quenched with water. An equal volume of 10% aqueous sodium carbonate is added to the reaction mass. The reaction mass is then distilled on a 12" Goodloe column yielding the following fractions:

| Fraction No. | Vapor Temp. (°C.) | Liquid Temp. (°C.) | Vacuum mm/Hg. Pressure | Reflux Ratio | Weight of Fraction |
|---|---|---|---|---|---|
| 1 | 47/14 | 85/89 | 7.0/8.0 | 9:1/9:1 | 10.8 |
| 2 | 75 | 87 | 7.09 | 9:1 | 15.4 |
| 3 | 70 | 83 | 6.0 | 9:1 | 15.1 |
| 4 | 67 | 83 | 4.0 | 9:1 | 23.5 |
| 5 | 58 | 80 | 3.5 | 9:1 | 19.3 |
| 6 | 58 | 80 | 3.5 | 9:1 | 19.7 |
| 7 | 60 | 85 | 3.5 | 4:1 | 23.2 |
| 8 | 61 | 85 | 3.5 | 4:1 | 24.9 |
| 9 | 63 | 95 | 3.4 | 1:1 | 23.8 |
| 10 | 63 | 95 | 3.4 | 1:1 | 22.9 |
| 11 | 63 | 102 | 3.4 | 1:1 | 20.4 |
| 12 | 58 | 114 | 0.8 | 1:1 | 24.3 |
| 13 | 67 | 155 | 0.8 | 4:1 | 19.1. |

FIG. 1 is the GLC profile for the reaction product prior to distillation (Conditions: SE-30 column programmed at 180° C. isothermal). The peak indicated by reference numeral 10 is the peak for the compound having the structure:

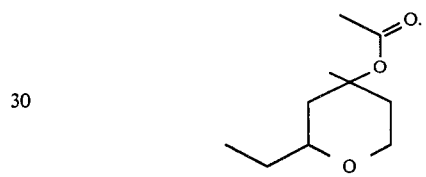

FIG. 2 is the NMR spectrum for the compound having the structure:

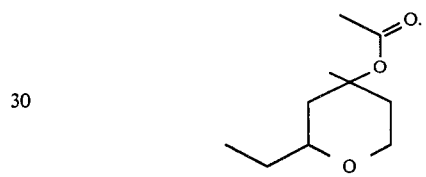

Distillation fraction (the foregoing distillation) 5–9 are bulked. The bulked distillation fractions have a fruity, green, chamomile and rose aroma profile.

EXAMPLE II

PREPARATION OF 2-ETHYL-4-METHYL-TETRAHYDRO PYRANYL PROPIONATE

Reaction:

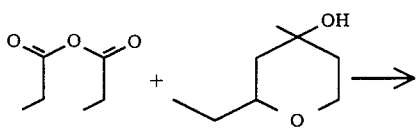

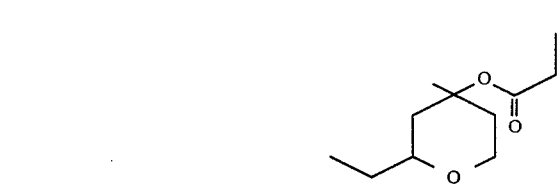

Into a 500 ml reaction flask equipped with stirrer, therometer, reflux condenser, addition funnel and cooling bath is placed 260 grams of propionic anhydride and 5 grams of methane sulfonic acid. Over a period of one hour while maintaining the temperature of the reaction mass at 30° C., 250 grams of 2-ethyl-4-methyl-tetrahydro pyranyl is added to the reaction mass. The reaction mass is stirred at a temperature in the range of 23°–30° C. for a period of one hour. At the end of the one hour period, the reaction mass is quenched with 500 ml water followed by 500 ml 10% aqueous sodium carbonate followed by 500 ml water.

The reaction mass is then distilled on a 12" Goodloe column yielding the following fractions:

| Fraction No. | Vapor Temp. (°C.) | Liquid Temp. (°C.) | Vacuum mm/Hg. Pressure | Reflux Ratio | Weight of Fraction |
|---|---|---|---|---|---|
| 1 | 59/77 | 85/97 | 7.0–6.0 | 9:1/9:1 | 9.0 |
| 2 | 79 | 94 | 6.0 | 9:1 | 10.0 |
| 3 | 78 | 94 | 6.0 | 9:1 | 14.0 |
| 4 | 78 | 94 | 6.0 | 9:1 | 13.0 |
| 5 | 79 | 94 | 6.0 | 9:1 | 22.0 |
| 6 | 79 | 94 | 6.0 | 9:1 | 17.0 |
| 7 | 79 | 94 | 6.0 | 9:1 | 15.0 |
| 8 | 79 | 95 | 6.0 | 4:1 | 20.0 |
| 9 | 81 | 96 | 6.0 | 4:1 | 22.0 |
| 10 | 82 | 97 | 6.0 | 4:1 | 24.0 |
| 11 | 83 | 97 | 6.0 | 4:1 | 25.0 |
| 12 | 83 | 105 | 6.0 | 4:1 | 21.0 |
| 13 | 63 | 109 | 1.0 | 4:1 | 20.0 |
| 14 | 61 | 122 | 0.8 | 4:1 | 17.0 |
| 15 | 66 | 145 | 0.8 | 4:1 | 14.0 |
| 16 | 71 | 173 | 0.8 | 4:1 | 12.0 |
| 17 | 78 | 210 | 0.8 | 4:1 | 11.0. |

FIG. 3 is the GLC profile for the crude reaction product prior to distillation. The peaks indicated by reference numerals 30A and 30B are the peaks for isomers of the compound having the structure:

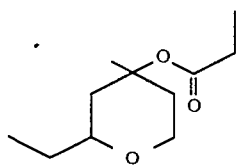

(GLC Conditions: SE-30 column programmed at 180° C. isothermal).

FIG. 4 is the NMR spectrum for the compound having the structure:

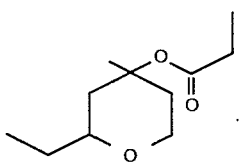

Distillation fractions 7–12 are bulked and the bulked distillation fractions have a fruity and chamomile aroma profile.

EXAMPLE III

| Fraction No. | Vapor Temp. (°C.) | Liquid Temp. (°C.) | Vacuum mm/Hg. Pressure | Reflux Ratio | Weight of Fraction |
|---|---|---|---|---|---|
| 1 | 45/50 | 90/101 | 10.0/10.0 | 9:1/9:1 | 6.1 |
| 2 | 52 | 101 | 10.0 | 9:1 | 7.7 |
| 3 | 86 | 180 | 10.0 | 9:1 | 14.3 |
| 4 | 85 | 100 | 10.0 | 9:1 | 15.0 |
| 5 | 78 | 94 | 6.0 | 9:1 | 17.5 |
| 6 | 77 | 94 | 5.5 | 9:1 | 16.8 |
| 7 | 76 | 94 | 4.8 | 9:1 | 12.7 |
| 8 | 74 | 95 | 4.2 | 9:1 | 20.5 |
| 9 | 116 | 97 | 4.2 | 9:1 | 24.5 |
| 10 | 79 | 99 | 4.2 | 9:1 | 21.0 |
| 11 | 81 | 105 | 4.2 | 9:1 | 25.9 |
| 12 | 81 | 117 | 4.2 | 9:1 | 20.9 |
| 13 | 81.5 | 137 | 4.2 | 9:1 | 16.2 |
| 14 | 83.6 | 172 | 4.2 | 9:1 | 11.6 |
| 15 | 678.3 | 207 | 4.3 | 9:1 | 9.3. |

FIG. 5 is the GLC profile for the crude reaction product prior to distillation (Conditions: SE-30 column programmed at 180° C. isothermal).

FIG. 6 is the NMR spectrum for the compound having the structure:

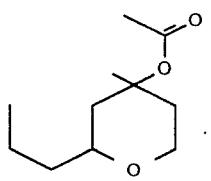

Distillation fractions 7–11 are bulked and the bulked distillation fractions have a sauge sclaree, tobacco-like, mentha citrata, lavender and witch hazel aroma profile with chamomile, rose, woody, sauge sclaree, lavender and winey undertones.

EXAMPLE IV

PREPARATION OF 2-n-PROPYL-4-METHYL-TETRAHYDRO PYRANYL PROPIONATE

Reaction:

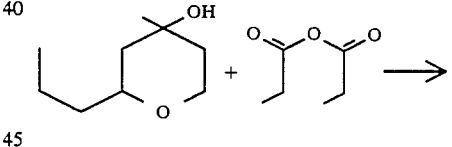

Into a 500 ml reaction flask equipped with stirrer, thermometer, reflux condenser, addition funnel and cooling both is placed 234 grams of propionic anhydride and 5 grams of methane sulfonic acid. Over a period of 30 minutes, 250 grams of 2-n-propyl-4-methyl-tetrahydro pyranyl is added to the reaction mass with stirring.

While maintaining the reaction mass at 30° C., the reaction mass is stirred for a period of one hour.

The reaction mass is then quenched with 500 ml water followed by 500 ml 10% aqueous sodium carbonate followed by 500 ml water.

The reaction mass is then distilled on a 12" Goodloe column yielding the following fractions:

| Fraction No. | Vapor Temp. (°C.) | Liquid Temp. (°C.) | Vacuum mm/Hg. Pressure | Reflux Ratio | Weight of Fraction |
|---|---|---|---|---|---|
| 1 | 33/46 | 96/100 | 10.0/10.2 | 9:1/9:1 | 9.6 |
| 2 | 71 | 91 | 3.0 | 9:1 | 12.3 |
| 3 | 68 | 92 | 1.0 | 9:1 | 23.4 |
| 4 | 69 | 93 | 1.0 | 9:1 | 17.9 |
| 5 | 60 | 95 | 1.0 | 4:1 | 20.3 |
| 6 | 60 | 95 | 1.0 | 4:1 | 21.9 |
| 7 | 60 | 97 | 1.0 | 4:1 | 25.8 |
| 8 | 60 | 97 | 1.0 | 4:1 | 25.0 |
| 9 | 63 | 100 | 0.65 | 4:1 | 30.5 |
| 10 | 62 | 103 | 0.65 | 4:1 | 28.0 |
| 11 | 63 | 108 | 0.65 | 4:1 | 26.2 |
| 12 | 74 | 118 | 0.65 | 4:1 | 16.5 |
| 13 | 65 | 135 | 0.65 | 4:1 | 12.0 |
| 14 | 67 | 180 | 0.65 | 4:1 | 9.8 |
| 15 | 67 | 200 | 0.65 | 4:1 | 6.0. |

FIG. 7 is the GLC profile of the crude reaction product prior to distillation. The peaks indicated by reference numerals 70A and 70B are the peaks for isomers of the compound having the structure:

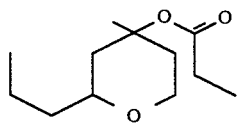

(Conditions: SE-30 column programmed at 180° C. isothermal).

FIG. 8 is the NMR spectrum for the compound having the structure:

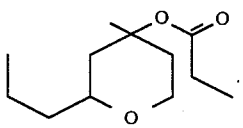

Distillation fractions 7–11 are bulked and the bulked distillation fractions have a woody, live flower petal-like and green aroma profile with floral (rose) and woody (copaiba oil) undertones.

EXAMPLE V

PREPARATION OF 2-ISOPROPYL-4-METHYL-TETRAHYDRO PYRANYL ACETATE

Reaction:

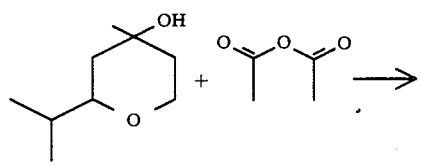

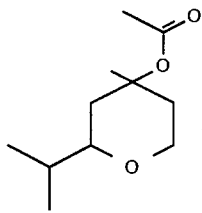

Into a 2 liter reaction flask equipped with stirrer, thermometer, reflux condenser, addition funnel and cooling bath are placed 296 grams of acetic anhydride and 3 grams of 98% methane sulfonic acid. While maintaining the reaction mass at 30° C. over a period of one hour 344 grams of 2-isopropyl-4-methyl-tetrahydro pyranyl is added to the reaction mass. The reaction mass is then stirred at 24°–28° C. for a period of one hour. At the end of the one hour period, the reaction mass is poured into 800 ml water and stirred for 30 minutes. The reaction mass is then washed with 500 ml 10% sodium carbonate and distilled on a 12" Goodloe column yielding the following fractions:

| Fraction No. | Vapor Temp. (°C.) | Liquid Temp. (°C.) | Vacuum mm/Hg. Pressure | Reflux Ratio | Weight of Fraction |
|---|---|---|---|---|---|
| 1 | 59/66 | 95/95 | 5.0/5.0 | 9:1/9:1 | 8.4 |
| 2 | 73 | 98 | 5.0 | 9:1 | 15.2 |
| 3 | 72 | 90 | 5.0 | 9:1 | 11.6 |
| 4 | 72 | 90 | 5.0 | 9:1 | 14.5 |
| 5 | 76 | 92 | 5.0 | 9:1 | 17.4 |
| 6 | 79 | 92 | 5.0 | 9:1 | 26.7 |
| 7 | 77 | 92 | 5.0 | 9:1 | 25.7 |
| 8 | 76 | 93 | 5.5 | 4:1 | 17.6 |
| 9 | 83 | 102 | 7.0 | 4:1 | 22.8 |
| 10 | 79 | 98 | 5.5 | 4:1 | 19.3 |
| 11 | 79 | 97 | 5.5 | 4:1 | 16.1 |
| 12 | 79 | 98 | 5.7 | 4:1 | 19.3 |
| 13 | 79 | 99 | 5.8 | 4:1 | 12.4 |
| 14 | 79 | 90 | 4.2 | 4:1 | 29.3 |
| 15 | 79 | 92 | 4.0 | 4:1 | 30.5 |
| 16 | 89 | 99 | 5.0 | 4:1 | 30.1 |
| 17 | 90 | 108 | 5.0 | 4:1 | 33.8 |
| 18 | 90 | 120 | 5.0 | 4:1 | 10.1 |
| 19 | 80 | 200 | 1.4 | 4:1 | 12.8. |

FIG. 9 is the GLC profile for the crude reaction product prior to the distillation (Conditions: SE-30 column programmed at 160° C. isothermal).

FIG. 10 is the NMR spectrum for the compound having the structure:

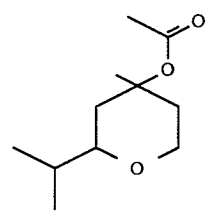

Distillation fractions 7–15 are bulked and the bulked distillation fractions have an orris, earthy (early morning forest path), oolong tea-like aroma profile with earthy (early morning forest path) undertones.

EXAMPLE VI

PREPARATION OF 2-ISOPROPYL-4-METHYL-TETRAHYDRO PYRANYL-4-PROPIONATE

Reaction:

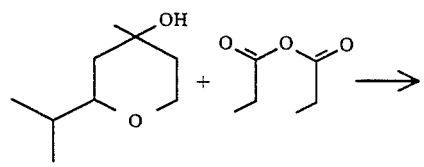

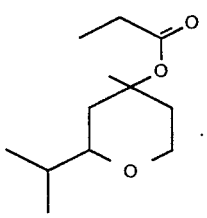

Into a 2 liter reaction flask equipped with stirrer, thermometer, reflux condenser, addition funnel and cooling bath is placed 260 grams of propionic anhydride and 3 grams of 98% methane sulfonic acid. Over a period of one hour while maintaining the reaction mass at 30° C. with stirring, 275 grams of 2-isopropyl-4-methyl tetrahydro pyranyl-4 is added to the reaction mass. The reaction mass is then stirred at 26°–30° C. for a period of two hours. At the end of the two hour period, the reaction mass is quenched with 500 ml water followed by one liter of 10% aqueous sodium carbonate. The resulting product is fractionally distilled on a 12" Goodloe column yielding the following fractions:

| Fraction No. | Vapor Temp. (°C.) | Liquid Temp. (°C.) | Vacuum mm/Hg. Pressure | Reflux Ratio | Weight of Fraction |
|---|---|---|---|---|---|
| 1 | 25/27 | 83/85 | 3.0/3.0 | 9:1/9:1 | 12.0 |
| 2 | 32 | 93 | 5.0 | 9:1 | 18.6 |
| 3 | 39 | 100 | 5.0 | 9:1 | 22.9 |
| 4 | 38 | 101 | 5.0 | 9:1 | 26.4 |
| 5 | 45 | 105 | 5.0 | 4:1 | 17.8 |
| 6 | 77 | 105 | 5.0 | 4:1 | 20.2 |
| 7 | 81 | 105 | 5.0 | 4:1 | 20.2 |
| 8 | 82 | 106 | 5.0 | 4:1 | 21.2 |
| 9 | 78 | 105 | 3.6 | 4:1 | 26.4 |
| 10 | 78 | 97 | 3.6 | 4:1 | 26.6 |
| 11 | 79 | 97 | 3.8 | 4:1 | 29.4 |
| 12 | 80 | 97 | 3.8 | 4:1 | 26.0 |
| 13 | 79 | 98 | 3.6 | 4:1 | 28.5 |
| 14 | 79 | 99 | 3.6 | 4:1 | 27.7 |
| 15 | 82 | 100 | 3.9 | 4:1 | 27.0 |
| 16 | 82 | 100 | 3.8 | 4:1 | 29.2 |
| 17 | 83 | 101 | 3.7 | 4:1 | 22.1 |
| 18 | 83 | 101 | 3.7 | 4:1 | 22.1 |
| 19 | 84 | 99 | 3.6 | 4:1 | 24.1 |
| 20 | 87 | 105 | 3.8 | 4:1 | 24.3 |
| 21 | 87 | 114 | 3.8 | 4:1 | 24.2 |
| 22 | 87 | 200 | 3.8 | 4:1 | 19.7. |

FIG. 11 is the GLC profile for the compound having the structure:

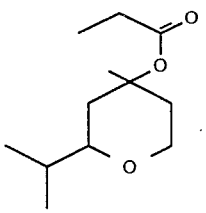

Distillation fractions 7–18 are bulked and the bulked distillation fractions have a floral (rose), fruity, green, piney and woody aroma profile.

EXAMPLE VII

PREPARATION OF 2-n-BUTYL-4-METHYL-TETRAHYDRO PYRANYL-4-ACETATE

Reaction:

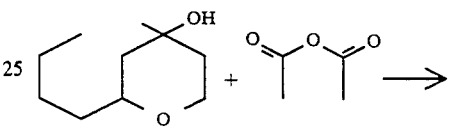

Into a 2 liter reaction flask equipped with stirrer, thermometer, reflux condenser, addition funnel and cooling bath are placed 184 grams of acetic anhydride and 2 grams of methane sulfonic acid. The reaction mass is cooled to 10° C. with stirring and over a period of 0.5 hours while maintaining the reaction mass at 10° C., 250 grams of 2-n-butyl-4-methyl-tetrahydro pyranyl-4 is added to the reaction mass with stirring. The reaction mass is continued to be stirred at 10° C. for a period of six hours.

At the end of the six hour period, the reaction mass is quenched with 500 ml water followed by 10 grams sodium acetate followed by 500 ml 5% aqueous sodium carbonate followed by 500 ml water.

The reaction is then distilled on a 12" Goodloe column yielding the following fractions:

| Fraction No. | Vapor Temp. (°C.) | Liquid Temp. (°C.) | Vacuum mm/Hg. Pressure | Reflux Ratio | Weight of Fraction |
|---|---|---|---|---|---|
| 1 | 68/88 | 105/105 | 3.8/3.8 | 9:1/9:1 | 9.9 |
| 2 | 88 | 108 | 3.8 | 9:1 | 16.5 |
| 3 | 88 | 109 | 3.8 | | 24.6 |
| 4 | 92 | 108 | 3.5 | 4:1 | 24.3 |
| 5 | 92 | 108 | 3.5 | 4:1 | 33.7 |
| 6 | 90 | 108 | 3.5 | 2:1 | 32.1 |
| 7 | 95 | 110 | 3.5 | 2:1 | 26.0 |
| 8 | 95 | 112 | 4.0 | 2:1 | 23.4 |
| 9 | 95 | 112 | 4.0 | 2:1 | 27.6 |
| 10 | 95 | 114 | 4.0 | 2:1 | 31.5 |
| 11 | 95 | 120 | 4.0 | 2:1 | 30.6 |
| 12 | 90 | 155 | 4.0 | 2:1 | 13.9. |

FIG. 12 is the GLC profile for the reaction mass prior to distillation containing the compound having the structure:

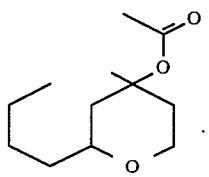

FIG. 13 is the NMR spectrum for the compound having the structure:

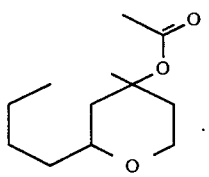

Distillation fractions 4–11 are bulked and the bulked distillation fractions have an ozoney and woody aroma profile.

EXAMPLE VIII

PREPARATION OF 2-ISOBUTYL-4-METHYL-TETRAHYDRO PYRANYL-4-PROPIONATE

Reaction:

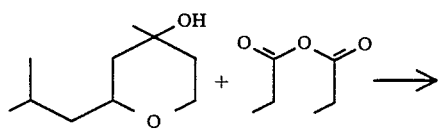

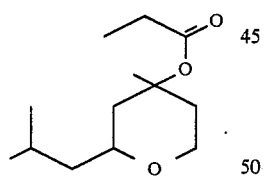

Into a 2 liter reaction flask equipped with stirrer, thermometer, reflux condenser, addition funnel and cooling bath is placed 247 grams of propionic anhydride and 2.5 grams of 98% methane sulfonic acid. The reaction mass is cooled to 15° C. and over a period of one hour while maintaining the reaction mass of 15° C., 220 grams of 2-isobutyl-4-tetrahydro pyranyl-4 is added to the reaction mass. The reaction mass is maintained with stirring at a temperature of 15° C. for a period of fifteen hours. At the end of the fifteen hour period, the reaction mass is quenched with 500 ml aqueous 10% sodium carbonate followed by another 500 ml aqueous 10% sodium carbonate. The reaction mass is then distilled on a 12" Goodloe column yielding the following fractions:

| Fraction No. | Vapor Temp. (°C.) | Liquid Temp. (°C.) | Vacuum mm/Hg. Pressure | Reflux Ratio | Weight of Fraction |
|---|---|---|---|---|---|
| 1 | 28/30 | 102/102 | 1.8/1.6 | 9:1/9:1 | 22.6 |
| 2 | 31 | 105 | 1.6 | 9:1 | 16.7 |
| 3 | 79 | 105 | 1.6 | 9:1 | 13.0 |
| 4 | 78 | 102 | 1.3 | 9:1 | 28.0 |
| 5 | 79 | 103 | 1.1 | 9:1 | 27.2 |
| 6 | 85 | 104 | 1.7 | 9:1 | 25.9 |
| 7 | 82 | 103 | 1.4 | 9:1 | 22.0 |
| 8 | 83 | 105 | 1.4 | 9:1 | 24.5 |
| 9 | 85 | 106 | 1.4 | 9:1 | 23.5 |
| 10 | 85 | 107 | 1.3 | 9:1 | 25.2 |
| 11 | 88 | 108 | 1.4 | 9:1 | 22.2 |
| 12 | 88 | 109 | 1.4 | 9:1 | 20.0 |
| 13 | 78 | 135 | 1.2 |  | 31.1 |
| 14 | 65 | 210 | 1.0 | 4.1 | 6.5. |

FIG. 14 is the GLC profile for the reaction mass prior to distillation containing the compound having the structure:

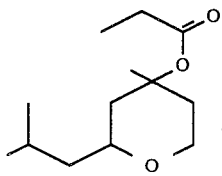

FIG. 15 is the NMR spectrum for the compound having the structure:

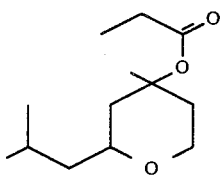

Distillation fractions 6–11 are bulked and the bulked distillation fractions have a natural, waxy aroma with fatty undertones.

EXAMPLE IX

PREPARATION OF 2-ISOBUTYL-4-METHYL-TETRAHYDRO PYRANYL-4-ACETATE

Reaction:

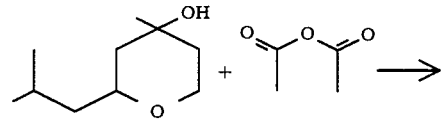

Into a 2 liter reaction flask equipped with stirrer, thermometer, reflux condenser and cooling bath are placed 204 grams of acetic anhydride and 2 grams of 98% methane sulfonic acid. The reaction mass is cooled to 10° C. and over a period of one hour 220 grams of 2-isobutyl-4-methyl-tetrahydro pyranyl-4 is added to the reaction mass with stirring.

The reaction mass is then maintained at 10° C. with stirring for a period of seven hours.

At the end of the seven hour period, the reaction mass is quenched by adding thereto 500 ml water followed by 500 ml 5% aqueous sodium carbonate solution.

The reaction mass is then fractionally distilled on a 12" Goodloe column yielding the following fractions:

| Fraction No. | Vapor Temp. (°C.) | Liquid Temp. (°C.) | Vacuum mm/Hg. Pressure | Reflux Ratio | Weight of Fraction |
|---|---|---|---|---|---|
| 1 | 56/57 | 90/90 | 1.0/1.0 | 9:1/9:1 | 5.7 |
| 2 | 82 | 110 | 3.0 | 9:1 | 12.6 |
| 3 | 82 | 100 | 3.0 | 9:1 | 14.3 |
| 4 | 72 | 100 | 3.0 | 9:1 | 13.0 |
| 5 | 72 | 100 | 3.0 | 9:1 | 13.4 |
| 6 | 77 | 91 | 3.0 | 9:1 | 13.4 |
| 7 | 78 | 100 | 3.0 | 9:1 | 11.2 |
| 8 | 78 | 100 | 3.0 | 9:1 | 14.5 |
| 9 | 78 | 105 | 3.0 | 4:1 | 13.5 |
| 10 | 78 | 107 | 3.0 | 4:1 | 13.4 |
| 11 | 85 | 107 | 3.0 | 4:1 | 17.6 |
| 12 | 90 | 107 | 3.0 | 4:1 | 14.7 |
| 13 | 95 | 105 | 3.0 | 4:1 | 13.6 |
| 14 | 85 | 110 | 3.0 | 4:1 | 16.9 |
| 15 | 85 | 110 | 3.0 | 4:1 | 16.8 |
| 16 | 85 | 110 | 3.0 | 4:1 | 21.1 |
| 17 | 85 | 110 | 3.0 | 4:1 | 14.1 |
| 18 | 85 | 115 | | | 10.8 |
| 19 | 78 | 155 | 3.0 | | 9.9 |
| 20 | 75 | 200 | 0.8 | | 3.9. |

FIG. 16 is the GLC profile for the reaction product prior to distillation (Conditions: SE-30 column programmed at 180° C. isothermal).

FIG. 17 is the NMR spectrum for the compound having the structure:

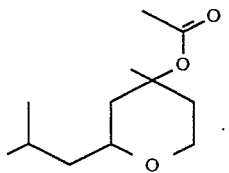

Distillation fractions 11–17 are bulked and the bulked distillation fractions have a guiacwood-like, floral (rose) aroma profile.

EXAMPLE X

PREPARATION OF 2-N-BUTYL-4-METHYL-TETRAHYDRO PYRANYL-4-PROPIONATE

Reaction:

Reaction:

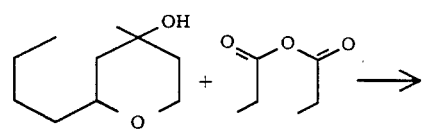

Into a 1 liter reaction vessel equipped with stirrer, thermometer, reflux condenser, addition funnel and cooling bath is placed 176 grams of propionic anhydride and 2 grams of methane sulfonic acid (98%).

While maintaining the reaction mass at 10° C., over a period of one hour 200 grams of 2-n-butyl-4-methyl-tetrahydro pyranyl-4 is added to the reaction mass.

The reaction mass is then maintained at 10° C. with stirring for a period of five hours.

At the end of the five hour period, the reaction mass is quenched with 500 ml 5% aqueous sodium acetate followed by 500 ml 10% aqueous sodium carbonate. The reaction mass is then distilled on a 12" Goodloe column yielding the following fractions:

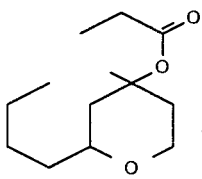

| Fraction No. | Vapor Temp. (°C.) | Liquid Temp. (°C.) | Vacuum mm/Hg. Pressure | Reflux Ratio | Weight of Fraction |
|---|---|---|---|---|---|
| 1 | 46/86 | 109/112 | 2.0/2.0 | 9:1/9:1 | 17.6 |
| 2 | 82 | 112 | 1.6 | 9:1 | 10.9 |
| 3 | 86 | 112 | 1.6 | 4:1 | 9.9 |
| 4 | 78 | 110 | 1.2 | 4:1 | 11.8 |
| 5 | 79 | 112 | 1.2 | 4:1 | 11.2 |
| 6 | 82 | 115 | 1.2 | 4:1 | 11.2 |
| 7 | 81 | 115 | 1.2 | 4:1 | 15.4 |
| 8 | 82 | 115 | 1.2 | 4:1 | 11.9 |
| 9 | 82 | 115 | 1.2 | 4:1 | 15.8 |
| 10 | 83 | 110 | 1.2 | 4:1 | 13.5 |
| 11 | 85 | 110 | 1.2 | 4:1 | 14.9 |
| 12 | 84 | 110 | 1.2 | 4:1 | 14.6 |
| 13 | 85 | 110 | 1.2 | 4:1 | 15.2 |
| 14 | 84 | 110 | 1.2 | 4:1 | 14.5 |
| 15 | 85 | 110 | 1.2 | 1:1 | 18.7 |
| 16 | 84 | 110 | 1.2 | 1:1 | 11.3 |
| 17 | 83 | 110 | 1.2 | 100% | 12.9 |
| 18 | 84 | 130 | 1.2 | 100% | 9.8 |
| 19 | 64 | 170 | 1.2 | 100% | 6.6. |

FIG. 18 is the GLC profile for the reaction product prior to distillation containing the compound having the structure;

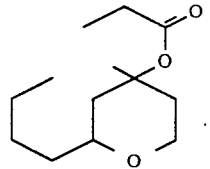

(Conditions: SE-30 column programmed at 180° C. isothermal).

FIG. 19 is the NMR spectrum for the compound having the structure:

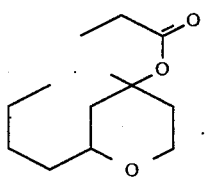

Fractions 6–14 of the foregoing distillation are bulked and bulked fractions 6–14 have a sweet, jasmine aroma with a soft woody (cabreuva) undertone.

EXAMPLE XI

PREPARATION OF 2-(2-PENYYL)-4-METHYL-TETRAHYDRO PYRANYL-4-ACETATE

Reaction:

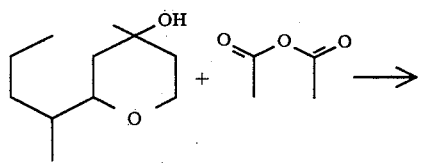

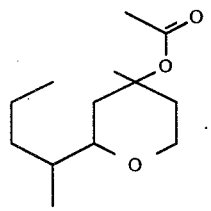

Into a 2 liter reaction flask equipped with stirrer, thermometer, reflux condenser and cooling bath is placed 144 grams of acetic anhydride and 1.5 grams of 98% methane sulfonic acid. The reaction mass is cooled to 15° C. and while maintaining the reaction mass at 15° C., 190 grams of 2-(2-pentyl)-4-methyl-tetrahydro pyranyl-4 is added to the reaction mass. The reaction mass is then maintained with stirring at 15° C. for a period of six hours.

At the end of the six hour period, the reaction mass is quenched with 500 ml water followed by 10 grams of solid sodium acetate followed by 500 ml water followed by 500 ml 5% aqueous sodium carbonate.

The reaction mass is then fractionally distilled on a 12" Goodloe column yielding the following fractions:

| Fraction No. | Vapor Temp. (°C.) | Liquid Temp. (°C.) | Vacuum mm/Hg. Pressure | Reflux Ratio | Weight of Fraction |
|---|---|---|---|---|---|
| 1 | 70/70 | 107/100 | 1.4/1.4 | 9:1/9:1 | 10.8 |
| 2 | 70 | 98 | 1.0 | 9:1 | 12.8 |
| 3 | 72 | 100 | 1.0 | 4:1 | 14.9 |
| 4 | 72 | 102 | 1.0 | 4:1 | 19.3 |
| 5 | 72 | 102 | 1.0 | 4:1 | 18.3 |
| 6 | 75 | 102 | 1.0 | 4:1 | 16.0 |
| 7 | 75 | 102 | 1.0 | 4:1 | 17.6 |
| 8 | 78 | 103 | 1.0 | 4:1 | 15.8 |
| 9 | 78 | 105 | 1.0 | 4:1 | 16.8 |
| 10 | 78 | 110 | 1.0 | 1:1 | 20.8 |
| 11 | 78 | 110 | 1.0 | 1:1 | 10.6 |
| 12 | 80 | 117 | 1.0 | 1:1 | 15.8 |
| 13 | 80 | 115 | 1.0 | 1:1 | 8.0 |
| 14 | 80 | 120 | 1.0 | 1:1 | 8.5 |
| 15 | 65 | 170 | 1.0 | 4:1. | |

-continued

FIG. 11 is the GLC profile for the reaction product prior to distillation containing the compound having the structure:

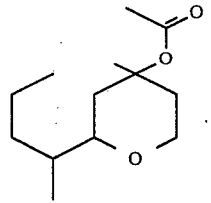

FIG. 21 is the NMR spectrum for the compound having the structure:

Distillation fractions 3–11 are bulked and the bulked distillation fractions have a non-descript aroma.

EXAMPLE XII

PREPARATION OF 1-(2-METHYL-1-PROPENYL)-4-METHYL-TET-RAHYDRO PYRANYL-4-ACETATE

Reaction:

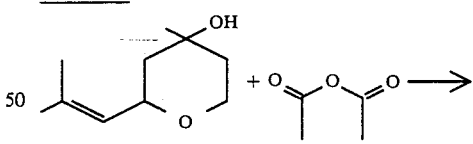

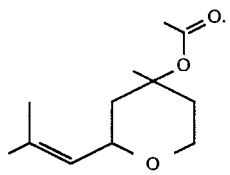

Into a 500 ml reaction flask equipped with stirrer, thermometer, reflux condenser, addition funnel and cooling bath is placed 136 grams of acetic anhydride and 3 grams of 98% methane sulfonic acid. While maintaining the reaction mass at 25° C. over a period of 0.5 hours, 150 grams of the compound having the structure:

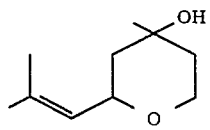

is added to the reaction mass. The reaction mass is then maintained with stirring at 25° C. for a period of 1.25 hours.

At the end of the 1.25 hour period, the reaction mass is quenched with 300 ml water followed by 300 ml aqueous 10% sodium carbonate followed by 300 ml water.

The reaction mass is then fractionally distilled on a 12" Goodloe column yielding the following fractions:

| Fraction No. | Vapor Temp. (°C.) | Liquid Temp. (°C.) | Vacuum mm/Hg. Pressure | Reflux Ratio | Weight of Fraction |
|---|---|---|---|---|---|
| 1 | 78/80 | 100/102 | 1.4/1.4 | 9:1/9:1 | 10.8 |
| 2 | 77 | 105 | 1.2 | 9:1 | 11.0 |
| 3 | 77 | 105 | 1.2 | 9:1 | 9.6 |
| 4 | 78 | 105 | 1.2 | 9:1 | 8.7 |
| 5 | 79 | 110 | 1.1 | 9:1 | 9.3 |
| 6 | 79 | 107 | 1.0 | 9:1 | 10.0 |
| 7 | 79 | 109 | 1.1 | 9:1 | 11.0 |
| 8 | 79 | 110 | 1.1 | 9:1 | 8.3 |
| 9 | 80 | 114 | 1.1 | 9:1 | 11.3 |
| 10 | 80 | 114 | 1.1 | 9:1 | 10.5 |
| 11 | 90 | 125 | 1.1 | 4:1 | 15.0 |
| 12 | 91 | 130 | 1.1 | 4:1 | 16.3 |
| 13 | 108 | 137 | 1.1 | 4:1 | 18.1 |
| 14 | 108 | 140 | 1.1 | 4:1 | 11.7 |
| 15 | 107 | 175 |  |  | 10.0 |
| 16 | 112 | 180 | 1.1 | 4:1 | 3.0. |

FIG. 22 is the GLC profile for the reaction product prior to distillation (Conditions: SE-30 column programmed at 180° C. isothermal).

The peaks indicated by reference numerals 220A and 220B are the peaks for isomers of the compound having the structure:

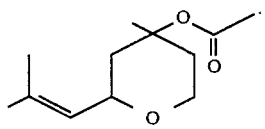

FIG. 23 is the NMR spectrum for the compound having the structure:

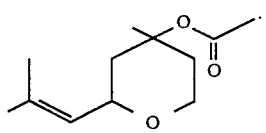

Distillation fractions 5-10 are bulked and the bulked distillation fractions 5-10 have a fruity, citrusy, green, rose (geranium) and piney aroma profile with floral (geranium), oatmeal and herbaceous undertones.

EXAMPLE XIII

PREPARATION OF 2-(2-METHYL-1-PROPENYL)-4-METHYL-TETRAHYDRO PYRANYL-4-PROPIONATE

Reaction:

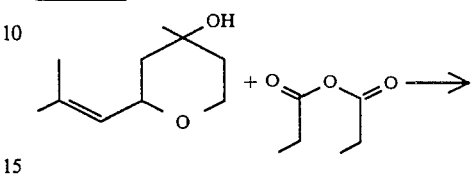

In to a 500 ml reaction flask equipped with stirrer, thermometer, reflux condenser, addition funnel and cooling bath is placed 156 grams of propionic anhydride and 3 grams of 98% methane sulfonic acid. While maintaining the reaction mass at 25° C. over a period of 0.5 hours, 150 grams of the compound having the structure:

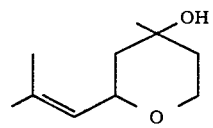

is added to the reaction mass. The reaction mass is then maintained at 25° C. with stirring for a period of four hours. At the end of the four hour period, the reaction mass is quenched with 500 ml water and distilled on a 12" Goodloe distillation column yielding the following fractions:

| Fraction No. | Vapor Temp. (°C.) | Liquid Temp. (°C.) | Vacuum mm/Hg. Pressure | Reflux Ratio | Weight of Fraction |
|---|---|---|---|---|---|
| 1 | 50/33 | 105/105 | 2.0 | 9:1 | 7.0 |
| 2 | 88 | 105 | 2.0 | 9:1 | 14.0 |
| 3 | 87 | 105 | 2.0 | 9:1 | 13.0 |
| 4 | 94 | 106 | 2.0 | 9:1 | 17.0 |
| 5 | 89 | 107 | 2.0 | 9:1 | 23.0 |
| 6 | 86 | 105 | 2.0 | 9:1 | 16.0 |
| 7 | 86 | 107 | 1.2 | 9:1 | 23.0 |
| 8 | 85 | 121 | 1.2 | 9:1 | 27.0 |
| 9 | 88 | 147 | 1.2 | 4:1 | 22.0 |
| 10 | 120 | 184 | 1.2 | 4:1 | 11.0 |
| 11 | 100 | 200 | 1.2 |  | 12.0 |
| 12 | 80 | 210 | 1.8 |  | 1.7. |

FIG. 24 is the GLC profile for the reaction product prior to distillation containing the compound having the structure:

FIG. 25 is the NMR spectrum for the compound having the structure:

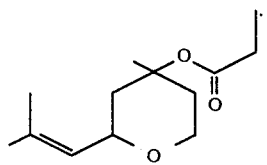

Distillation fractions 6–8 are bulked and bulked distillation fractions 6–8 have a green, floral (rose/muguet), lily, herbaceous and citrusy (grapefruit) aroma profile with floral, rose, spicy and black pepper undertones.

EXAMPLE XIV

The following Chypre formulations are prepared:

| Ingredients | Parts by Weight | | | |
| --- | --- | --- | --- | --- |
| | XIV(A) | XIV(B) | XIV(C) | XIV(D) |
| Musk ambrette | 40 | 40 | 40 | 40 |
| Musk ketone | 60 | 60 | 60 | 60 |
| Coumarin | 30 | 30 | 30 | 30 |
| Oil of bergamot | 150 | 150 | 150 | 150 |
| Oil of lemon | 100 | 100 | 100 | 100 |
| Methyl ionone | 50 | 50 | 50 | 50 |
| Hexyl cinnamic aldehyde | 100 | 100 | 100 | 100 |
| Hydroxycitronellal | 100 | 100 | 100 | 100 |
| Oil of Lavender | 50 | 50 | 50 | 50 |
| Texas cedarwood oil | 85 | 85 | 85 | 85 |
| Virginia cedarwood oil | 30 | 30 | 30 | 30 |
| Oil of sandalwood (East Indies) | 40 | 40 | 40 | 40 |
| Isoeugenol | 20 | 20 | 20 | 20 |
| Eugenol | 10 | 10 | 10 | 10 |
| Benzyl acetate | 30 | 30 | 30 | 30 |
| β-phenyl ethyl alcohol | 40 | 40 | 40 | 40 |
| α-phenyl ethyl alcohol | 30 | 30 | 30 | 30 |
| Oakmoss absolute | 30 | 30 | 30 | 30 |
| Vetiver oil Venezuela | 25 | 25 | 25 | 25 |
| The compound having the structure: 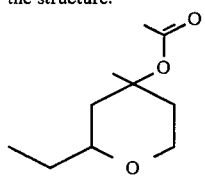 prepared according to Example I, bulked distillation fractions 5–9. | 62 | 0 | 0 | 0 |
| The compound having the structure: 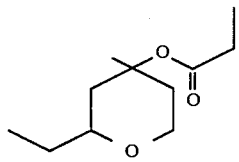 prepared according to Example II, bulked fractions 7–12. | 0 | 62 | 0 | 0 |
| The compound having the structure: 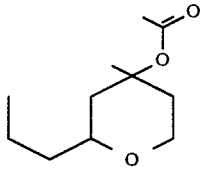 | 0 | 0 | 62 | 0 |

-continued

| Ingredients | Parts by Weight | | | |
|---|---|---|---|---|
| | XIV(A) | XIV(B) | XIV(C) | XIV(D) |
| prepared according to Example III, bulked fractions 7-11. The compound having the structure: 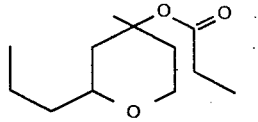 prepared according to Example IV, bulked distillation fractions 7-11. | 0 | 0 | 0 | 62 |

The compound having the structure:

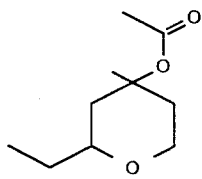

prepared according to Example I imparts to this Chypre formulation an intense and long-lasting fruity, green, chamomile and rose undertones. Accordingly, the formulation of Example XIV(A) can be described as "Chypre having a fruity, green, chamomile and rose undertones".

The compound having the structure:

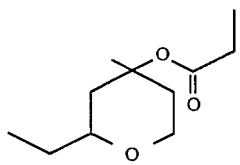

prepared according to Example II imparts to this Chypre formulation an intense and long-lasting fruity and chamomile undertones. Accordingly, the formulation of Example XIV(B) can be described as "Chypre having fruity and chamomile undertones".

The compound having the structure:

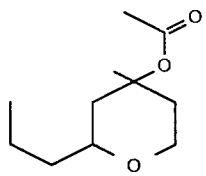

prepared according to Example III imparts to this Chypre formulation sauge sclaree, tobacco-like, mentha citrata, lavender and witch hazel topnotes with chamomile, rose, woody, sauge sclaree, lavender and winey undertones. Accordingly, the formulation of Example XIV(C) can be described as "Chypre having sauge sclaree, tobacco-like, mentha citrata, lavender and witch hazel topnotes with chamomile, rose, woody, sauge sclaree, lavender and winey undertones".

The compound having the structure:

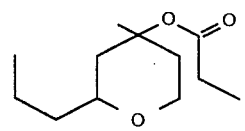

prepared according to Example IV imparts to this Chypre formulation a woody, live flower petal-like and green topnotes with floral, rose, woody and copaiba oil undertones. Accordingly, the formulation of Example XIV(D) can be described as "Chypre having woody, live flower petal-like and green topnotes with floral, rose, woody and copaiba oil undertones".

EXAMPLE XV

The following Chypre formulations are prepared:

| Ingredients | Parts by Weight | | | |
|---|---|---|---|---|
| | XV(A) | XV(B) | XV(C) | XV(D) |
| Musk ambrette | 40 | 40 | 40 | 40 |
| Musk ketone | 60 | 60 | 60 | 60 |
| Coumarin | 30 | 30 | 30 | 30 |
| Oil of bergamot | 150 | 150 | 150 | 150 |
| Oil of lemon | 100 | 100 | 100 | 100 |
| Methyl ionone | 50 | 50 | 50 | 50 |
| Hexyl cinnamic aldehyde | 100 | 100 | 100 | 100 |
| Hydroxycitronellal | 100 | 100 | 100 | 100 |
| Oil of Lavender | 50 | 50 | 50 | 50 |
| Texas cedarwood oil | 85 | 85 | 85 | 85 |
| Virginia cedarwood oil | 30 | 30 | 30 | 30 |
| Oil of sandalwood (East Indies) | 40 | 40 | 40 | 40 |
| Isoeugenol | 20 | 20 | 20 | 20 |
| Eugenol | 10 | 10 | 10 | 10 |
| Benzyl acetate | 30 | 30 | 30 | 30 |
| β-phenyl ethyl alcohol | 40 | 40 | 40 | 40 |
| α-phenyl ethyl alcohol | 30 | 30 | 30 | 30 |
| Oakmoss absolute | 30 | 30 | 30 | 30 |
| Vetiver oil Venezuela | 25 | 25 | 25 | 25 |
| The compound having the structure: 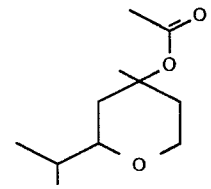 | 62 | 0 | 0 | 0 |

-continued

| Ingredients | Parts by Weight | | | |
|---|---|---|---|---|
| | XV(A) | XV(B) | XV(C) | XV(D) |
| prepared according to Example V, bulked distillation fractions 7-15. | | | | |
| The compound having the structure: 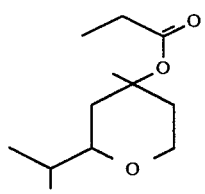 prepared according to Example VI, bulked distillation fractions 7-18. | 0 | 62 | 0 | 0 |
| The compound having the structure: 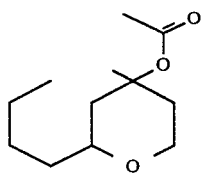 prepared according to Example VII, bulked distillation fractions 4-11. | | | | |
| The compound having structure: 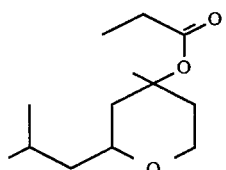 prepared according to Example VIII, bulked distillation fractions 6-11. | 0 | 0 | 0 | 62 |

The compound having the structure:

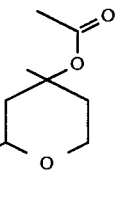

prepared according to Example V imparts to this Chypre formulation intense and long-lasting orris, earthy, early morning forest path-like and oolong tea-like topnotes with earthy, early morning forest path-like undertones. Accordingly, the formulation of Example XV(A) can be described as "Chypre having orris, earthy, early morning forest path-like and oolong tea-like topnotes with earthy and early morning forest path-like undertones".

The compound having the structure:

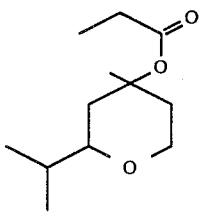

imparts to this Chypre formulation floral, rose, fruity, green, piney and woody undertones. Accordingly, the formulation of Examples XV(B) can be described as "Chypre having floral, rose, fruity, green, piney and woody undertones".

The compound having the structure:

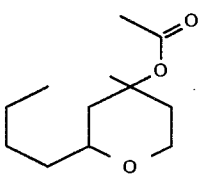

prepared according to Example XII imparts to this Chypre formulation ozoney and woody undertones. Accordingly, the formulation of Example XV(C) can be described as "Chypre having ozoney and woody undertones".

The compound having the structure:

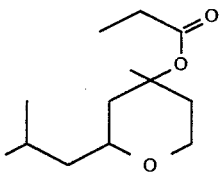

prepared according to Example VIII imparts to this Chypre formulation natural, waxy topnotes with fatty undertones. Accordingly, the formulation of Example XV(D) can be described as "Chypre having natural, waxy topnotes with fatty undertones".

EXAMPLE XVI

The following Chypre formulations are prepared:

| Ingredients | Parts by Weight | | | |
|---|---|---|---|---|
| | XVI(A) | XVI(B) | XVI(C) | XVI(D) |
| Musk ambrette | 40 | 40 | 40 | 40 |
| Musk ketone | 60 | 60 | 60 | 60 |
| Coumarin | 30 | 30 | 30 | 30 |
| Oil of bergamot | 150 | 150 | 150 | 150 |
| Oil of lemon | 100 | 100 | 100 | 100 |
| Methyl ionone | 50 | 50 | 50 | 50 |
| Hexyl cinnamic aldehyde | 100 | 100 | 100 | 100 |
| Hydroxycitronellal | 100 | 100 | 100 | 100 |
| Oil of Lavender | 50 | 50 | 50 | 50 |
| Texas cedarwood oil | 85 | 85 | 85 | 85 |
| Virginia cedarwood oil | 30 | 30 | 30 | 30 |
| Oil of sandalwood (East Indies) | 40 | 40 | 40 | 40 |
| Isoeugenol | 20 | 20 | 20 | 20 |
| Eugenol | 10 | 10 | 10 | 10 |
| Benzyl acetate | 30 | 30 | 30 | 30 |
| β-phenyl ethyl alcohol | 40 | 40 | 40 | 40 |
| α-phenyl ethyl alcohol | 30 | 30 | 30 | 30 |

-continued

| Ingredients | Parts by Weight | | | |
|---|---|---|---|---|
| | XVI(A) | XVI(B) | XVI(C) | XVI(D) |
| Oakmoss absolute | 30 | 30 | 30 | 30 |
| Vetiver oil Venezuela | 25 | 25 | 25 | 25 |
| The compound having the structure: 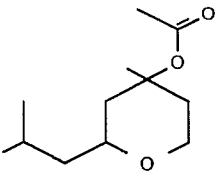 prepared according to Example IX, bulked fractions 11-17. | 62 | 0 | 0 | 0 |
| The compound having the structure: 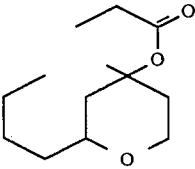 prepared according to Example X, bulked fractions 6-14. | 0 | 62 | 0 | 0 |
| The compound having the structure: 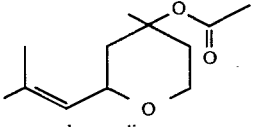 prepared according to Example XII, bulked fractions 5-10. | 0 | 0 | 62 | 0 |
| The compound having the structure: 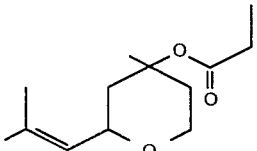 prepared according to Example XIII, bulked fractions 6-8. | 0 | 0 | 0 | 62 |

The compound having the structure:

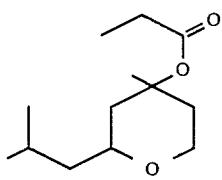

prepared according to Example IX imparts to this Chypre formulation a guiawood-like and floral and rose set of undertones. Accordingly, the formulation of Example XVI(A) can be described as "Chypre-like with guiawood-like, floral and rose undertones".

The compound having the structure:

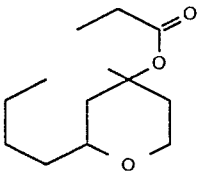

produced according to Example X imparts to this Chypre formulation sweet and jasmine topnotes with soft woody and cabreuva undertones. Accordingly, the formulation of Example XVI(B) can be described as "Chypre with sweet and jasmine topnotes and soft, woody and cabreuva undertones".

The compound having the structure:

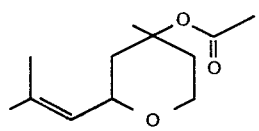

prepared according to Example XII imparts to this Chypre formulation an intense and long-lasting fruity, citrusy, green, rose, geranium and piney topnotes with floral, geranium, oatmeal and herbaceous undertones. Accordingly, the formulation of Example XVI(C) can be described as "Chypre with fruity, citrusy, green, rose, geranium and piney topnotes and floral, geranium, oatmeal and herbaceous undertones".

The compound having the structure:

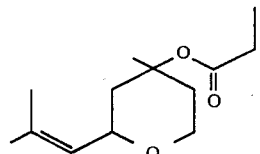

prepared according to Example XIII imparts to this Chypre formulation intense and long-lasting green, floral, rose, muguet, lily, herbaceous, citrusy and grapefruit topnotes with floral, rose, spicy and black pepper undertones. Accordingly, the formulation of Example XVI(D) can be described as "Chypre with green, floral, rose, muguet, lily, herbaceous, citrusy and grapefruit topnotes and floral, rose, spicy and black pepper undertones".

EXAMPLE XVII

PREPARATION OF COSMETIC POWDER COMPOSITIONS

Cosmetic powder compositions are prepared by mixing in a ball mill 100 grams of talcum powder with 0.25 grams of each of the substances set forth in Table III below. Each of the cosmetic powder compositions has an excellent aroma as described in Table III below:

TABLE III

| Substance | Aroma Description |
|---|---|
| The compound having the structure: | A fruity, green, chamomile and rose aroma profile. |

TABLE III-continued

| Substance | Aroma Description |
|---|---|
| 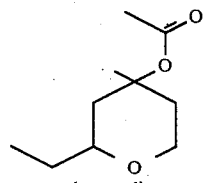 prepared according to Example I, bulked distillation fractions 5-9. The compound having the structure: | A fruity and chamomile aroma profile. |
| 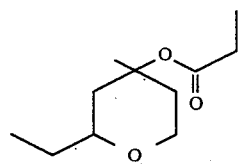 prepared according to Example II, bulked fractions 7-12. The compound having the structure: | A sauge sclaree, tobacco-like, mentha citrata, lavender and witch hazel aroma profile with chamomile, rose, woody, sauge sclaree, lavender and winey undertones. |
| 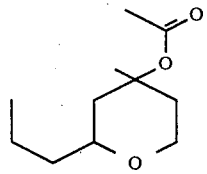 prepared according to Example III, bulked fractions 7-11. The compound having the structure: | A woody, live flower petal-like and green aroma profile with floral, rose and woody and copaiba oil undertones. |
| 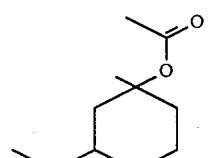 prepared according to Example IV, bulked fractions 7-11. The compound having the structure: | An orris, earthy (early morning forest path), oolong tea-like aroma with earthy (early morning forest path) undertones. |
| 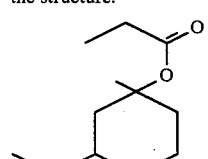 prepared acording to Example V, bulked fractions 7-15. The compound having the structure: | A floral (rose), fruity, green, piney and woody aroma profile. |
| 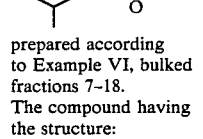 prepared according to Example VI, bulked fractions 7-18. The compound having the structure: | An ozoney and woody aroma profile. |

TABLE III-continued

| Substance | Aroma Description |
|---|---|
| 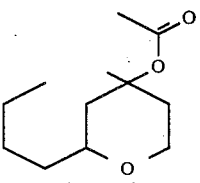 prepared according to Example VII, bulked fractions 4-11. The compound having the structure: | A natural, waxey aroma with fatty undertones. |
| 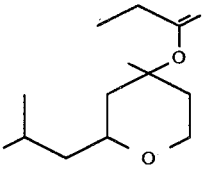 prepared according to Example VIII, bulked fractions 6-11. The compound having the structure: | A guiacwood-like and floral (rose) aroma profile. |
| 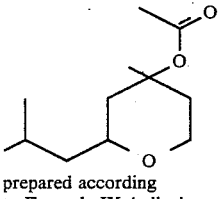 prepared according to Example IX, bulked fractions 11-17. The compound having the structure: | A sweet and jasmine aroma profile with soft, woody (copaiba oil) undertones. |
| 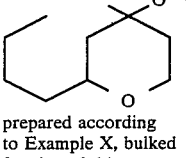 prepared according to Example X, bulked fractions 6-14. The compound having the structure: | A fruity, citrusy, green, rose (geranium) and piney aroma profile with floral (geranium) oatmeal and herbaceous undertones. |
| 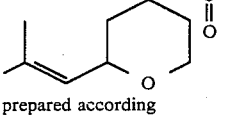 prepared according to Example XII, bulked fractions 5-10. The compound having the structure: | A green, floral (rose/muguet), lily, herbaceous and citrusy (grapefruit) aroma profile with floral, rose, spicy and black pepper-like undertones. |
| 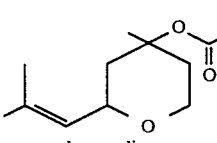 prepared according to Example XIII, bulked fractions 6-8. | |
| Perfume formulation of Example XIV(A). | Chypre having a fruity, green, chamomile and rose undertones. |
| Perfume formulation of | Chypre having fruity and |

TABLE III-continued

| Substance | Aroma Description |
| --- | --- |
| Example XIV(B). | chamomile undertones. |
| Perfume formulation of Example XIV(C). | Chypre having sauge sclaree, tobacco-like, mentha citrata, lavender and witch hazel topnotes with chamomile, rose, woody, sauge sclaree, lavender and winey undertones. |
| Perfume formulation of Example XIV(D). | Chypre having woody, live flower peal-like and green topnotes with floral, rose, woody and copaiba oil undertones. |
| Perfume formulation of Example XV(A). | Chypre having orris, earthy, early morning forest-path-like and oolong tea-like topnotes with earthy and early morning forest parh-like undertones. |
| Perfume formulation of Example XV(B). | Chypre having floral, rose, fruity, green, piney and woody undertones. |
| Perfume formulation of Example XV(C). | Chypre having ozoney and woody undertones. |
| Perfume formulation of Example XV(D) | Chypre having natural, waxy topnotes with fatty undertones. |
| Perfume formulation of Example XVI(A). | Chypre-like with guiawood-like, floral and rose undertones. |
| Perfume formulation of Example XVI(B). | Chypre with sweet and jasmine topnotes and soft, woody and cabreuva undertones. |
| Perfume formulation of Example XVI(C). | Chypre with fruity, citrusy, green, rose, geranium and piney topnotes and floral, geranium, oatmeal and herbacious undertones. |
| Perfume formulation of Example XVI(D). | Chypre with green, floral, rose, spicy and black pepper undertones. |

EXAMPLE XVIII

PERFUMED LIQUID DETERGENTS

Concentrated liquids detergents (Lysine salt of n-dodecylbenzene sulfonic acid as more specifically described in U.S. Pat. No. 3,948,818 issued on Apr. 6, 1976) with aroma nuances as set forth in Table III of Example XVII are prepared containing 0.10%, 0.15%, 0.20%, 0.25%, 0.30% and 0.35% of the substance set forth in Table III of Example XVII. They are prepared by adding and homogeneously mixing the appropriate quantity of substance set forth in Table III of Example XVII in the liquid detergent. The detergents all possess excellent aromas as set forth in Table III of Example XVII, the intensity increasing with greater concentrations of substance as set forth in Table III of Example XVII.

EXAMPLE XIX

PREPARATION OF COLOGNES AND HANDKERCHIEF PERFUMES

Compositions as set forth in Table III of Example XVII are incorporated into colognes at concentrations of 2.0%, 25.0%, 3.0%, 3.5%, 4.0%, 4.5% and 5.0% in 80%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table III of Example XVII are imparted to the colognes and to the handkerchief perfumes at all levels indicated.

EXAMPLE XX

PREPARATION OF SOAP COMPOSITIONS

One hundred grams of soap chips [per sample]-(IVORY ®, produced by the Procter & Gamble Company of Cincinnati, Ohio), are each mixed with one gram samples of substances as set forth in Table III of Example XVII until homogeneous compositions are obtained. In each of the cases, the homogeneous compositions are heated under 8 atmospheres pressure at 180° C. for a period of three hours and the resulting liquids are placed into soap molds. The resulting soap cakes, on cooling, manifest aromas as set forth in Table III of Example XVII.

EXAMPLE XXI

PREPARATION OF SOLID DETERGENT COMPOSITIONS

Detergents are prepared using the following ingredients according to Example I of Canadian Pat. No. 1,007,948:

| Ingredient | Percent By Weight |
| --- | --- |
| "NEODO ® 45-11" (a $C_{14}$-$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a phosphate-free detergent. Samples of 100 grams of this detergent are admixed with 0.10, 0.15, 0.20 and 0.25 grams of each of the substances as set forth in Table III of Example XVII. Each of the detergent samples has an excellent aroma as indicated in Table III of Example XVII.

EXAMPLE XXII

Utilizing the procedure of Example I at column 15 of U.S. Pat. No. 3,632,396, non-woven cloth substrates useful as dry-added fabric softening articles of manufacture are prepared wherein the substrate, the substrate coating and the outer coating and the perfuming material are as follows:

1. A water "dissolvable" paper ("Dissolvo Paper");
2. Adogen 448 (m.p. about 140° F.) as the substrate coating; and
3. An outer coating having the following formulation (m.p. about 150° F.):
   15%—$C_{20-22}$ HAPS
   22%—isopropyl alcohol
   20%—antistatic agent
   1%—of one of the substances as set forth in Table III of Example XVII.

Fabric softening compositions prepared according to Example I at column 15 of U.S. Pat. No. 3,632,396 having aroma characteristics as set forth in Table III of Example XVII, consist of a substrate coating having a weight of about 3 grams per 100 square inches of substrate; a first coating on the substrate coating consisting of about 1.85 grams per 100 square inches of substrate; and an outer coating coated on the first coating consisting of about 1.4 grams per 100 square inches of substrate. One of the substances of Table III of Example XVII is admixed in each case with the outer coating mixture, thereby providing a total aromatized outer coating weight ratio to substrate of about 0.5:1 by weight of the substrate. the aroma characteristics are imparted in a pleasant manner to the head space in a dryer on operation thereof in each case using said dryer-added fabric softener non-woven fabrics and these aroma characteristics are described in Table III of example XVII.

EXAMPLE XXIII

HAIR SPRAY FORMULATIONS

The following hair spray formulation is prepared by first dissolving PVP/VA E-735 copolymer manufactured by the GAF Corporation of 140 West 51St Street, New York, N.Y., in 91.62 grams of 95% food grade ethanol, 8.0 grams of the polymer is dissolved in the alcohol. The following ingredients are added to the PVP/VA alcoholic solution:

| Ingredients | Weight Percent |
|---|---|
| Dioctyl sebacate | 0.05 |
| Benzyl alcohol | 0.10 |
| Dow Corning 473 fluid (prepared by the Dow Corning Corporation) | 0.10 |
| Tween 20 surfactant (prepared by ICI America Corporation) | 0.03 |
| of the perfumery One of the perfumery substances as set forth in Table III of Example XVII | 0.10 |

The perfuming substances as set forth in Table III of Example XVII add aroma characteristics as set forth in Table III of Example XVII which are rather intense and aesthetically pleasing to the users of the soft-feel, good-hold pump hair sprays.

EXAMPLE XXIV

CONDITIONING SHAMPOOS

Monoamid CMA (prepared by the Mona Industries Company) (3.0 weight percent) is method with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of Union Carbide Corporation)(1.4 weight percent). The resulting melt is admixing with Stepanol WAT produced by the Stepan Chemical Company (35.0 weight percent). The resulting mixture is heated to 60° C. and mixed until a clear solution is obtained (at 60° C.).

GAEQUAT® 775N polymer (manufactured by GAF Corporation of 140 West 51st Street, New York, N.Y.)(5.0 weight percent) is admixed with 0.1 weight percent sodium sulfite and 1.4 weight percent polyethylene glycol 6000 distearate produced by Armak Corporation.

The resulting material is then mixed and cooled to 45° C. and 0.3 weight percent of perfuming substance as set forth in Table III of Example XVII is added to the mixture. The resulting mixture is cooled to 40° C. and blending is carried out for an additional one hour in each case. At the end of this blending period, the resulting material has a pleasant fragrance as indicated in Table III of Example XVII.

EXAMPLE XXV

Four drops of each of the substances as set forth in Table III of Example XVII, supra, is added separately to two grams of AROMOX® DMC-W to produce a clear premix. The clear premix is added to 200 grams of CLOROX® with stirring resulting in a clear stable, single phase solution. Sufficient 1M aqueous NaOH is added to bring the pH of the mixture up to 12.8. The solution remains substantially stable at 120° F. for a period of seven days. When the 5% aqueous sodium hypochlorite solution is used as a laundry bleach, the resulting laundry, on dry-out in an atmosphere of 65% relative humidity yields substantially no characteristic "hypochlorite" odor, but does have a faint pleasant aroma as set forth in Table III of Example XVII. Furthermore, no such characteristic "hypochlorite" aroma is retained on the hands of the individual handling such laundry in both the wet and the dry states.

EXAMPLE XXVI

AROMOX® DMMC-W in various quantities is mixed with 0.1 grams of one of the substances set forth in Table III of Example XVII, supra. The resulting premixes are then added to 200 grams of an aqueous 5% sodium hypochlorite solution. Sufficient 12.5M aqueous NaOH is added to bring the pH of the mixture up to 13. The following results are obtained:

| Percentage AROMOX® DMMC-W | Clarity of Hypochlorite Solution after addition of Premix |
|---|---|
| 0.23% | Clear after three days |
| 0.15% | Clear after three days |
| 0.08% | Initially slightly turbid; two phases exist after three days. |

When the 5% aqueous sodium hypochlorite solution is used as a laundry bleach, the resulting laundry on dry-out, in an atmosphere of 65% relative humidity, yields substantially no characteristic "hypochlorite" odor, but does have a faint, pleasant aroma as set forth in Table III of Example XVII. Furthermore, no such characteristic "hypochlorite" aromas is retained on the hands of the individual handling such laundry in both the wet and dry states.

EXAMPLE XXVII

Two grams of AROMOX® DMMC-W is admixed with eight drops of one of the substances set forth in Table III of Example XVII, supra. The premix is then added with stirring to 200 grams of a 7% aqueous solution of lithium hypochlorite. Sufficient 3M aqueous LiOH is added to bring the pH of the solution to 13.4. The mixture is then heated to 120° F. and maintained at that temperature with stirring for a period of one week. The resulting solution remains clear in a single phase. When used as a laundry bleach, the resulting bleached laundry, on dry-out in an atmosphere of 50% relative humidity retains a "clean" warm aroma as set forth in Table III of Example XVII, supra; whereas without the use of the substance set forth in Table III of Example XVII, supra, the bleached laundry has a faint characteristic disagreeable "hypochlorite" aroma.

EXAMPLE XXVIII

Two grams of AROMOX ® DMMC-W is admixed with eight drops of one of the substance of Table III of Example XVII, supra. This premix is then added, with stirring to 200 grams of a mixture containing 4.5% aqueous sodium hypochlorite. Sufficient 4M aqueous LiOH is added to bring the pH of the solution to 13.4. The mixture is then heated to 120° F. and maintained at that temperature for a period of one week. The resulting solution remains clear in a single phase. When used as a laundry bleach, the resulting bleached laundry on dry-out in an atmosphere of 50% relative humidity retains a "clean fresh" warm aroma as set forth in Table III of Example XVII, supra; whereas without the use of the substrate set forth in Table III of Example XVII, supra, the bleached laundry has a faint characteristic disagreeable "hypochlorite" aroma.

EXAMPLE XXIX

Two grams of AROMOX ® DMMC-W is admixed with eight drops of one of the substances as set forth in Table III of Example XVII, supra. This premix is then added with stirring to 200 grams of a mixture containing 4.5% aqueous sodium hypochlorite and 4.5% aqueous lithium hypochlorite. Sufficient 2M aqueous NaOH is added to bring the pH of the solution to 13.4. The mixture is then heated to 110° F. and maintained at that temperature with stirring for a period of 2 weeks. The resulting solution remains clear as a single phase when used as a laundry bleach. The resulting laundry bleach, on dry-out in an atmosphere of 50% relative humidity, retains an aroma as set forth in Table III of Example XVII, supra, whereas without the use of the substance set forth in Table III of Example XVII, supra, the bleached laundry has a faint characteristic disagreeable "hypochlorite" aroma.

EXAMPLE XXX

Four drops of one of the substances set forth in Table III of Example XVII, supra, is added to 1.5 grams of AROMOX ® to produce a clear premix. The clear premix is added to 200 grams of CLOROX ® with stirring resulting in a clear stable single phase solution. Sufficient 1M aqueous NaOH is added to bring the pH of the mixture up to 12.8. The solution remains substantially stable at 120° F. for a period of 7 days. When the 5% aqueous sodium hypochlorite solution is used as a laundry bleach, the resulting laundry on dry-out in an atomsphere of 65% relative humidity yields substantially no characteristic "hypochlorite" odor but does have a faint pleasant warm, long-lasting aroma as set forth in Table III of Example XVII, supra. Furthermore, no such characteristic "hypochlorite" aroma is retained on the hands of the individual handling such laundry in both the wet and dry states.

EXAMPLE XXXI

Four drops of one of the substances set forth in Table III of Example XVII, supra, is added to 1 gram n-undecyl dimethyl amine oxide to produce a clear premix. The clear premix is added to 200 grams of CLOROX ® with stirring resulting in a clear stable single phase solution. Sufficient 1M aqueous NaOH is added to bring the pH of the mixture up to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic "hypochlorite" odor but does have a faint pleasant warm aroma as set forth in Table III of Example XVII, supra. Furthermore, no such characteristic "hypochlorite" aroma is retained on the hands of the individual handling such laundry in both the wet and the dry states.

EXAMPLE XXXII

Four drops of one of the substances as set forth in Table III of Example XVII, supra, are added to 1 gram of n-dedecyl dimethyl amine oxide to produce a clear premix. The clear premix is added to 200 grams of CLOROX ® with stirring resulting in a clear, stable single phase solution. Sufficient 1M aqueous NaOH is added to bring the pH of the mixture up to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristics "hypochlorite" aroma, but does have a warm, pleasant, long-lasting aroma as set forth in Table III of Example XVII, supra. Furthermore, no such characteristic "hypochlorite" aroma is retained on the hands of the individual handling such laundry in both the wet and dry states.

EXAMPLE XXXIII

One gram of n-tridecyl dimethyl amine oxide is admixed with eight drops of one of the substances as set forth in Table III of Example XVII, supra. This premix is then added with stirring to 200 grams of a 7% aqueous solution of lithium hypochlorite. Sufficient 3M aqueous LiOH is added to bring the pH of the solution to 13.4. The mixture is then heated to 120° F. and maintained at that temperature with stirring for a period of one week. The resulting solution remains clear in a single phase. When used as a laundry bleach, the resulting bleached laundry on dry-out in an atmosphere of 50% relative humidity retains a warm, fresh aroma described in Table III of Example XVII, supra, whereas without the use of one of the substances of Table III of Example XVII, supra, the bleached laundry has a faint characteristic disagreeable "hypochlorite" aroma.

EXAMPLE XXXIV

Four drops of the compound having the structure:

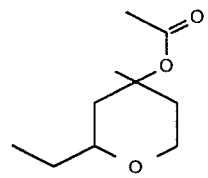

prepared according to Example I, bulked fractions 5-9 is added to 2 grams of AROMOX ® DMC-W to produce a clear premix. The clear premix is added to 200 grams of CLOROX ® with stirring resulting in a clear stable single phase solution. Sufficient 1M aqueous NaOH is added to bring the pH of the mixture up to 12.8. The solution remains substantially stable at 120° F. for a period of seven days. When the 5% aqueous sodium hypochlorite solution is used as a laundry bleach, the resulting laundry on dry-out in an atmosphere of 65% relative humidity yields substantially no characteristic "hypochlorite" odor but does have a fruity, green, chamomile and rose aroma. Furthermore, no such characteristic "hypochlorite" aroma is retained on the hands of the individual handling such laundry in both the wet and the dry states.

EXAMPLE XXXV

AROMOX ® DMMC-W in various quantities is mixed with 0.1 grams of the compound having the structure:

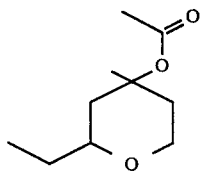

prepared according to Example I, bulked fractions 5-9. The resulting premixes is then added to 200 grams of an aqueous 5% sodium hypochlorite solution. Sufficient 12.5M aqueous NaOH is added to bring the pH of the mixture up to 13.

The following results are obtained:

| Percentage AROMOX ® DMMC-W | Clarity of Hypochlorite Solution After Additon of Premix |
|---|---|
| 0.23% | Clear after three days. |
| 0.15% | Clear after three days. |
| 0.08% | Initially slightly turbid: two phases exist after three days. |

When the 5% aqueous sodium hypochlorite solutions are used as laundry bleaches, the resulting laundry batches on dry-out in an atmosphere of 65% relative humidty yields substantially no characteristic "hypochlorite" odor, but do have fruity, green, chamomile and rose aroma. Furthermore, no such characteristics "hypochlorite" aroma is retained on the hands of the individual handling such laundry batches in both the wet and the dry states.

EXAMPLE XXXVI

Two grams of AROMOX ® DMMC-W are admixed with eight drops of the the compound having the structure:

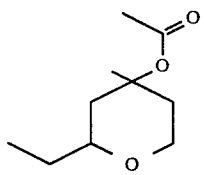

prepared according to Example I, bulked fractions 5-9. The premix is then added with stirring to 200 grams of a 7% aqueous solution on lithium hypochlorite. Sufficient 3M aqueous LiOH is added to bring the pH of the solution to 13.4. The mixtures are then heated to 120° F. and maintained at that temperature with stirring for a period of one week. The resulting solution remains clear in a single phase. When used as laundry bleaches, the resulting bleached laundry batches on dry-out in an atmosphere of 50% relative humidity retain a fruity, green, chamomile and rose aroma; whereas without the the compound having the structure:

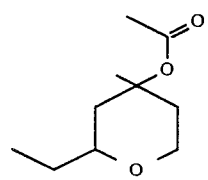

prepared according to Example I, bulked fractions 5-9, the bleached laundry batches have a faint characteristic disagreeable "hypochlorite" aroma.

EXAMPLE XXXVII

Two grams of AROMOX ® DMMC-W are admixed with eight drops of the compound having the structure:

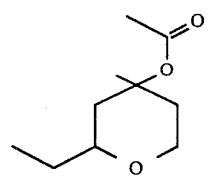

prepared according to Example I, bulked fractions 5-9. The premix is then added with stirring to 200 grams of a mixture containing 4.5% aqueous sodium hypochlorite and 4.5% aqueous lithium hypochlorite, Sufficient 4M aqueous LiOH is added to bring the pH of the solution to 13.4. The mixture is then heated to 120° F. and maintained at that temperature for a period of one week. The resulting solution remains clear in a single phase. When used as a laundry bleach, the resulting bleached laundry batches on dry-out in an atmosphere of 50% relative humidity retain a fruity, green, chamomile and rose aroma; whereas without the use of the the compound having the structure:

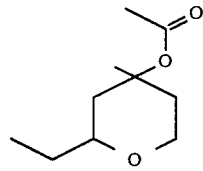

prepared according to Example I, bulked fractions 5-9, the bleached laundry dry batches having faint characteristic disagreaable "hypochlorite" aroma.

EXAMPLE XXXVIII

Two grams of AROMOX ® DMMC-W are admixed with eight drops of either (a) the compound having the structure:

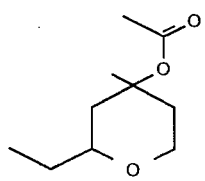

prepared according to Example I, bulked fractions 5-9; or (b) a 50—50 mixture the compound having the structure:

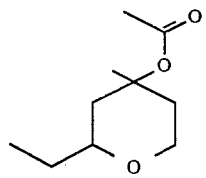

prepared according to Example I, bulked fractions 5-9 and diisoamylene epoxide produced according to Example II of application for U.S. Pat. Ser. No. 277,131 filed on June 25, 1981, the disclosure of which is incorporated herein by reference. These premixes are then added with stirring to 200 grams of a mixture containing 4% aqueous sodium hypochlorite and 4% aqueous lithium hypochlorite. Sufficient 2M aqueous NaOH is added to bring the pH of the solutions to 13.4. The mixtures are then heated to 110° F. and maintained at that temperature with stirring for a period of two weeks. The resulting solutions remains clear as a single phase when used as laundry bleaches. The resulting bleached laundry batches on dry-out in an atmosphere of 50% relative humidity retain either "fruity, green, chamomile and rose" aromas (when using the compound having the structure:

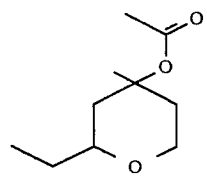

prepared according to Example I, bulked fractions 5-9) or retain fruity, green, chamomile and rose aromas when using the mixture of the diisoamylene epoxide and the compound having the structure:

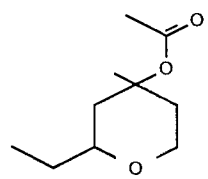

prepared according to Example I, bulked fractions 5-9; whereas without the use of the compound having the structure:

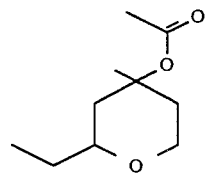

prepared according to Example I, bulked fractions 5-9 containing compositions of matter the bleached laundry batches having faint characteristic disagreeable "hypochlorite" aromas.

EXAMPLE XXXIX

Four drops of the compound having the structure:

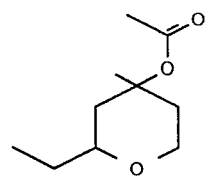

prepared according to Example I, bulked fractions 5-9 are added to 1.5 grams of AROMOX ® NCMD-W to produce a clear premix. The clear premix is added to 200 grams of CLOROX ® with stirring resulting in a clear stable single phase solution. Sufficient 1M aqueous NaOH is added to bring the pH of the mixture up to 12.8. The solution remains substantially stable at 120° F. for a period of seven days. When the 5% aqueous sodium hypochlorite solution is used as a laundry bleach, the resulting laundry on dry-out in an atmosphere of 65% relative humidity yields substantially no characteristic "hypochlorite" odor but does have a fruity, green, chamomile and rose aroma. Furthermore, no such characteristic "hyprochlorite" aroma is retained on the hands of the individual handling such laundry in both the wet and the dry states.

EXAMPLE XL

Four drops of the compound having the structure:

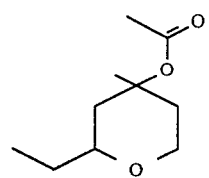

prepared according to Example I, bulked fractions 5-9, is added to 1 gram of n-undecyl dimethyl amine oxide to produce a clear premix. The clear premix is added to 200 grams of CLOROX ® with stirring resulting in a clear stable single phase solution. Sufficient 1M aqueous NaOH is added to bring the pH of the mixture of 12.8. The solution remains substantially stable at 120° F. for a period of seven days. When the 5% aqueous sodium hypochlorite solution is used as a laundry bleach the resulting laundry on dry-out in an atmosphere of 65% relative humidity yields substantially no characteristic "hypochlorite" odor but does have a "fruity, green, chamomile and rose" aroma. Furthermore, no such characteristic "hypochlorite" aroma is retained on the hands of the individual handling such laundry in both the wet and the dry states.

EXAMPLE XLI

One drop of n-tridecyl dimethyl amine oxide is admixed with eight drops of a 50:50 mixture of the diisoamylene epoxide prepared according to Example II of application for U.S. Pat. Ser. No. 277,131 filed on June 25, 1981 and the compound having the structure:

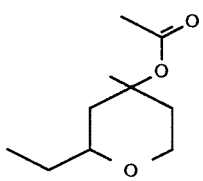

prepared according to Example I, bulked fractions 5-9, supra. This premix is then added with stirring to 200 grams of a 7% aqueous solution of lithium hypochlorite. Sufficient 3M aqueous LiOH is added to bring the pH of the solution to 13.4. The mixture is then heated to 120° F. and maintained at that temperature with stirring for a period of one week. The resulting solution remains clear in a single phase. When used as a laundry bleach, the resulting bleached laundry on dry-out in an atmosphere of 50% relative humidity retains a "fruity, green, chamomile and rose" aroma with stemmy nuances; whereas without the use of the mixture of diisoamylene epoxide and the compound having the structure:

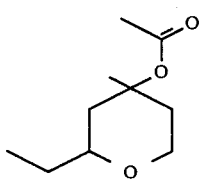

prepared according to Example I, bulked fractions 5-9 bleached laundry has a faint characteristic disagreeable "hypochlorite" aroma.

EXAMPLE XLII

AROMAX® DMMC-W in various quantities is mixed with 0.1 gram of a 25:75 weight:weight mixture of diisoamylene epoxide: the compound having the structure:

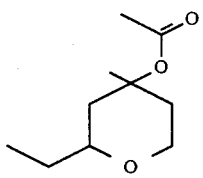

prepared according to Example I, bulked fractions 5-9.

The resulting premixes are then added to 200 grams of an aqueous 5% sodium hypochlorite solution. Sufficient 12.5M aqueous NaOH is added to bring the pH of the mixture up to 13. The following results are obtained:

| Percentage AROMOX ® DMMC-W | Clarity of Hypochlorite Solution After Additon of Premix |
|---|---|
| 0.23% | Clear after three days. |
| 0.15% | Clear after three days. |
| 0.08% | Initially slightly turbid: two phases exist after three days. |

When used as laundry bleaches, the resulting bleached laundries on dry-out in an atmosphere of 50% relative humidity in each of the three cases above retain a "fruity, green, chamomile and rose" with stemmy nuances, whereas without the use of the composition of matter set forth above containing diisoamylene epoxide and the compound having the structure:

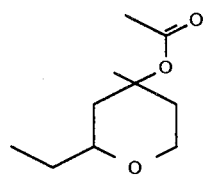

prepared according to Example I, bulked fractions 5-9 the bleached laundry has the same characteristic disagreeable "hypochlorite" aroma.

EXAMPLE XLIII

DOWFAX® 2A1 (see Note 1, infra) in various quantities, as set forth below, is mixed with 0.1 grams of a 50:50 mixture of (a) one of the diisoamylene epoxide compositions prepared according to Example II of application for U.S. Pat. Ser. No. 277,131 filed on June 25, 1981 and (b) the compound having the structure:

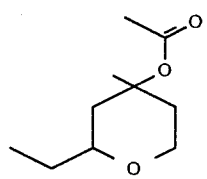

prepared according to Example I, bulked fractions 5-9. The resulting premixes are then added to 200 grams of an aqueous 7% sodium hypochlorite solution. Sufficient 12.5M aqueous sodium hydroxide is added to bring the pH of the mixture up to 13.5. The following results are obtained:

| Percentage of DOWFAX ® 2A1 | Clarity of Hypochlorite Solution After Addition of Premix |
|---|---|
| 0.23% | Clear after seven days. |
| 0.15% | Clear after five days. |
| 0.08% | Clear after three days. |
| 0.01% | Initially slightly turbid: two phases exist after three days. |

FIG. 5A represents a graph of percent residual chlorine versus time in hours for hypochlorite solutions containing DOWFAX® 2A1 (a registered trademark of the Dow Chemical Company of Midland, Mich.) identifying the compound having the structure:

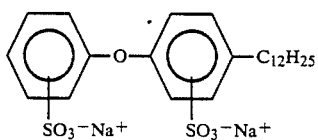

wherein the $C_{12}-H_{25}$ moiety is branched chain and the $SO_3-Na+$ moieties are at various positions on each of the enzene rings of AROMOX® DMMC-W, a 30% aqueous solution of dimethylcocoamine oxide having the structure:

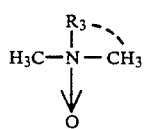

a trademark of Akzo Corporation of Chicago, Ill. (product produced by Armax, Division of Akzo Corporation of Chicago, Ill.) with the ratio of AROMOX® DMMC-W:base being 0.8:99 and the ratio of DOWFAX® 2A1:base being 0.8:99.

FIG. 5B is a graph of percent residual chlorine versus time in hours for hypochlorite solutions of (1) DOWFAX®2A1 and AROMOX®DMMC-W in absence of any fragrance or essential oils with the weight ratios of AROMOX®DMMC-W:base being 1.8.99 and 3.8:96 and the weight of ratios of DOWFAX®2A1:base being 1.8:99 and 3.8:99.

FIG. 6A is a graph of percent residual chlorine versus time in hours comparing hypochlorite solutions of DOWFAX®2A1 versus AROMOX®DMMC-W with the perfuming material being a 50:50 mixture of one of the diisoamylene products produced according to Example II, of application for U.S. Letters Patent, Ser. No. 277,131 filed on June 25, 1981 and the compound having the structure:

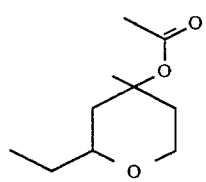

prepared according to Example I, bulked fractions 5-9, supra, wherein the weight ratio of AROMOX®DMMC-W:mixture of diisoamylene epoxide and the compound having the structure:

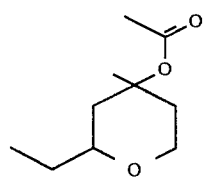

prepared according to Example I, bulked fractions 5-9:-base being either 0.8:0.2:9 or 1.8:0.2:9 and the weight ratio of DOWFAX®2A1:mixture of diisoamylene epoxide and the compound having the structure:

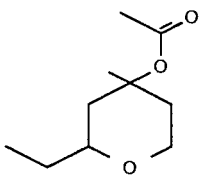

prepared according to Example I, bulked fractions 5-9:-base being either 0.8:0.2:9 or 1.8:0.2:9 and the weight ratio of DOWFAX®2A1:mixture of diisoamylene epoxide and the compound having the structure:

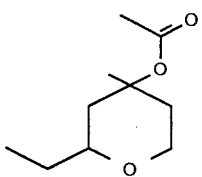

prepared according to Example I, bulked fractions 5-9:-base being 0.8:0.2:9 or 1.8:0.1:9.

FIG. 6B is a graph of percent residual chlorine versus time in hours comparing the performance of hypochlorite solutions containing (i) DOWFAX®2A1 versus (ii) AROMOX®DMMC-W using a 50:50 mixture of diisoamylene product produced according to Example II of application of U.S. Letters Patent, Ser. No. 277,131 filed on June 25, 1981 and the compound having the structure:

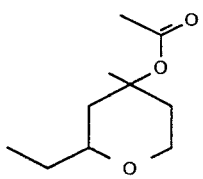

prepared according to Example I, bulked fractions 5-9, supra, or not using any fragrance or essential oils with the weight ratio of AROMOX®DMMC-W:mixture of diisoamylene epoxide and the compound having the structure:

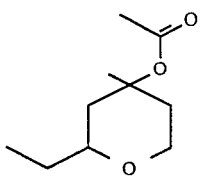

prepared according to Example I, bulked fractions 5-9:-base being 3.8:0.2:9 and the ratio of DOWFAX®2A1:-diisoamylene epoxide-the compound having the structure:

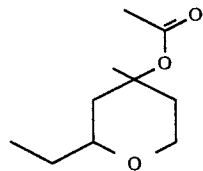

prepared according to Example I, bulked fractions 5-9:- base being 3.8:0.2:9.

Note 1: DOWFAX®2A1 is a material consisting essentially of the compound having the structure:

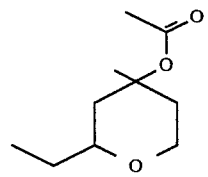

prepared according to Example I, bulked fractions 5-9 wherein the $C_{12}H_{25}$ moiety is branched chain and the $SO_3$-Na+ moieties are at various positions on each of the benzene rings.

EXAMPLE XLV

Four drops of a 25:75 weight/weight mixture of diisoamylene epoxide prepared according to Example II of application for U.S. Letters Patent, Ser. No. 277,131 the compound having the structure:

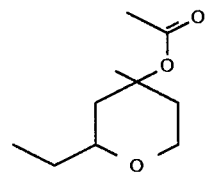

prepared according to Example I, bulked fractions 5-9, supra, is added to grams of DOWFAX®3B2 and 0.5 grams of AROMOX®DMC-W to produce a clear premix. The clear premix is added to 200 grams of CLOROX® with stirring resulting in a clear stable single phase solution. Sufficient 1M aqueous NaOH is added to bring the pH of the mixture of 12.8. The solution remains substantially stable at 120° F. for a period of seven days. When the 5% aqueous sodium hypochlorite solution is used as a laundry bleach, the resulting laundry on dry-out in an atmosphere of 65% relative humidity yields substantially no characteristic "hypochlorite" odor but does have a fruity, green, chamomile and rose aroma with stemmy nuances. Furthermore, no such characteristic "hypochlorite" aroma is retained on the hands of the individual handling such laundry in both the wet and the dry states.

EXAMPLE XLVI

One grams of DOWFAX®3B2; one gram of DOWFAX®2A1 and 0.25 grams of AROMOX®DMMC-W is admixed with eight drops of the compound having the structure:

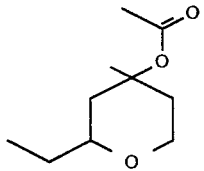

prepared according to Example I, bulked fractions 5-9. This premix is then added, with stirring to 200 grams of a mixture containing 4.5% aqueous sodium hypochlorite and 4.5% aqueous lithium hypochlorite. Sufficient 4M aqueous LiOH is added to bring the pH of the solution to 13.4. The mixture is then heated to 120° F. and maintained at that temperature for a period of one week. The resulting solution remains clear in a single phase. When used as a laundry bleach, the resulting bleached laundry on dry-out in an atmosphere of 50% relative humidity retains a fruity, green, chamomile and rose aroma; whereas the use of the compound having the structure:

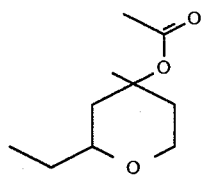

prepared according to Example I, bulked fractions 5-9, supra, the bleached laundry has a faint characteristic disagreeable "hypochlorite" aroma.

EXAMPLE XLVII

One gram of DOWFAX®2A1 and one gram of DOWFAX®3B2 is admixed with eight drops of a 50:50 mixture of one of the diisoamylene epoxide compositions of Example II of application for U.S. Letters Patent, Ser. No. 277,131 filed on June 25, 1981 and the compound having the structure:

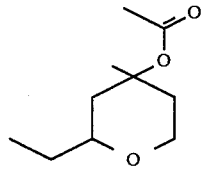

prepared according to Example I, bulked fractions 5-9. This premix is then added, with stirring to 200 grams of a mixture containing 4.5% aqueous sodium hypochlorite. Sufficient 4M aqueous LiOH is added to bring the pH of the solution to 13.4. The mixture is then heated to 120° F. and maintained at that temperature for a period of one week. The resulting solution remains clear in a single phase. When used as a laundry bleach, the resulting bleached laundry on dry-out in an atmosphere of 50% relative humidity remains a fruity, green, chamomile and rose aroma with stemmy nuances; whereas without the use of the perfume composition which is a mixture of diisoamylene epoxide and the compound having the structure:

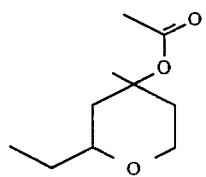

prepared according to Example I, bulked fractions 5-9, the bleached laundry has a faint characteristic disagreeable "hypochlorite" aroma.

EXAMPLE XLVIII

Four drops of a 50:50 mixture of one of the diisoamylene epoxide mixtures produced according to Example II of application for U.S. Letters Patent, Ser. No. 277,131 filed on June 25, 1981 and the compound having the structure:

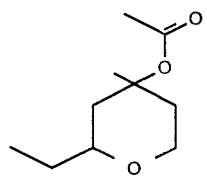

prepared according to Example I, bulked fractions 5-9, supra. is added to 1.0 grams of DOWFAX ®3B2 and 0.25 grams of AROMOX ®NCMD-W to produce a clear premix. The clear premix is added to 200 grams of CLOROX ® resulting in a clear stable single phase solution. Sufficient 1M aqueous NaOH is added to bring the pH of the mixture up to 12.8. The solution remains substantially stable at 120° F. for a period of seven days. When the 5% aqueous sodium hypochlorite solution is used as a laundry bleach, the resulting laundry on dry-out in an atmosphere of 65% relative humidity yields substantially no characteristic "hypochlorite" odor, but does have a fruity, green, chamomile and rose aroma with stemmy nuances. Furthermore, no such characteristic "hypochlorite" aroma is retained on the hands of the individual handling such laundry in both the wet and the dry states.

EXAMPLE XLIX

Four drops of the compound having the structure:

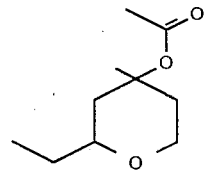

prepared according to Example I, bulked fractions 5-9, is added to 0.1 grams n-undecyl dimethyl amine oxide and 0.9 grams of DOWFAX ®3B2 to produce a clear premix. The clear premix is added to 200 grams of CLOROX ® with stirring resulting in a clear single phase solution. Sufficient 1M aqueous NaOH is added to bring the pH of the mixture up to 12.8. The solution remains substantially stable at 120° F. for a period of seven days. When the 5% aqueous sodium hypochlorite solution is used as a laundry bleach, the resulting laundry on dry-out in an atmosphere of 65% relative humidity yields substantially no characteristic "hypochlorite" odor, but does have a faint pleasant fruity, green, chamomile and rose aroma. Furthermore, no such characteristic "hypochlorite" aroma is retained on the hands of the individual handling such laundry in both the wet and the dry states.

EXAMPLE L

Four drops of a 50:50 mixture of diisoamylene epoxide produced according to Example II of application of U.S. Letters Patent, Ser. No. 277,131 filed on June 25, 1981 and the compound having the structure:

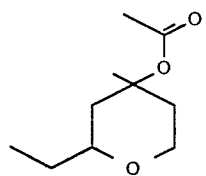

prepared according to Example I, bulked fractions 5-9, supra, is added to 0.1 gram of n-dodecyl dimethyl amine oxide and 0.9 grams of DOWFAX ®2A1 to produce a clear premix. The clear premix is added to 200 grams of CLOROX ® with stirring resulting in a clear stable single phase solution. Sufficient 1M aqueous NaOH is added to bring the pH of the mixture up to 12.8. The solution remains substantially stable at 120° F. for a period of seven days. When the 5% aqueous sodium hypochlorite solution is used as a laundry bleach, the resulting laundry on dry-out in an atmosphere of 65% relative humidity yields substantially no characteristic "hypochlorite" odor but does have a fruity, green, chamomile and rose aroma with stemmy nuances. Furthermore, no such characteristic "hypochlorite" aroma is retained on the hands of the individual handling such laundry in both the wet and the dry states.

EXAMPLE LI 0.2 Grams of n-tridecyl dimethyl amine oxide and 0.7 grams of DOWFAX ®3B2 are admixed with eight drops of the compound having the structure:

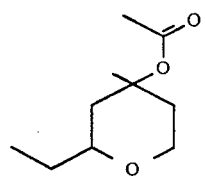

prepared according to Example I, bulked fractions 5-9, supra. This premix is then added with stirring to 200 grams of a 7% aqueous solution of lithium hypochlorite. Sufficient 3M aqueous LiOH is added to bring the pH of the solution to 13.4. The mixture is then heated to 120° F. and maintained at that temperature with stirring for a period of one week. The resulting solution remains clear in a single phase. When used as a laundry bleach, the resulting bleached laundry on dry-out in an atmosphere of 50% relative humidity retains a fruity, green, chamomile and rose aroma; whereas without the use of the compound having the structure:

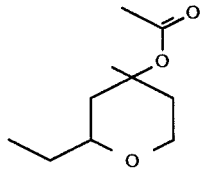

prepared according to Example I, bulked fractions 5-9 bleached laundry has a faint characteristic disagreeable "hypochlorite" aroma.

EXAMPLE LII

A mixture is prepare consisting of 39 grams of DOW-FAX®2A1 (60.75%); 4.5 grams of sodium palmitate (7.00%); and 20.7 grams of water (32.25%). The mixture is heated while stirring followed by ultrasonic dispersion thereby yielding a homogeneous gel. 64.2 Grams of this material is used as follows: 4 drops of the compound having the structure:

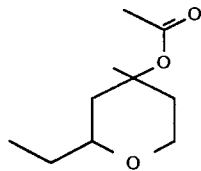

prepared according to Example I, bulked fractions 5-9 is added to 2.0 grams of the foregoing gel to produce a clear premix. The clear premix is added to 200 grams of CLOROX® with stirring resulting in a clear stable phase solution. Sufficient 1M aqueous NaOH is added to bring the pH of the mixture up to 12.8. The solution remains substantially stable at 120° F. for a period of seven days. When the 5% aqueous sodium hypochlorite solution is used as a laundry bleach, the resulting laundry on dry-out in an atmosphere of 65% relative humidity yields substantially no characteristic "hypochlorite" odor but does have a fruity, green, chamomile and rose aroma. Furthermore, no such characteristic "hypochlorite" aroma is retained on the hands of the individual handling such laundry in both the wet and the dry states.

EXAMPLE LIII

A mixture is prepared consisting of 39 grams of DOWFAX®2A1 (60.75); 4.5 grams sodium laurate (7.00%); and 20.7 grams of water (32.25%). The mixture is heated while stirring followed by ultrasonic dispersion thereby yielding a homogeneous gel. 64.2 Grams of this material is used as follows: 4 drops of (a) one of the diisoamylene epoxide mixtures produced according to Example II of application for U.S. Letters Patent, Ser. No. 277,131 filed on June 25, 1981 and (b) the compound having the structure:

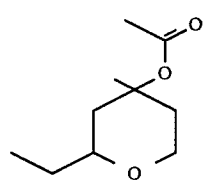

prepared according to Example I, bulked fractions 5-9, supra, is added to 2.0 grams of the foregoing gel to produce a clear premix. The clear premix is added to 200 grams of CLOROX® with stirring resulting in a clear stable single phase solution. Sufficient 1M aqueous NaOH is added to bring the pH of the mixture up to 12.8. The solution remains substantially stable at 120° F. for a period of seven days. When the 5% aqueous sodium hypochlorite solution is used as a laundry bleach, the resulting laundry on dry-out in an atmosphere of 65% relative humidity yields substantially no characteristic "hypochlorite" odor but does have a fruity, green, chamomile and rose aroma with stemmy nuances. Furthermore, no such characteristic "hypochlorite" aroma is retained on the hands of the individual handling such laundry in both the wet and the dry states.

EXAMPLE XIV

A mixture is prepared consisting of 20.1 grams DOWFAX®2A1 (60.75); 2.0 grams of sodium palmitate (7.00%); and 20.0 grams of water (32.25%). The mixture is heated while stirring followed by ultrasonic dispersion thereby yielding a homogeneous gel. 64.2 Grams of this material is used as follows: 4 drops of the compound having the structure:

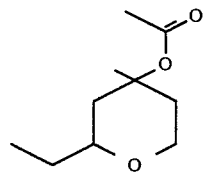

prepared according to Example I, bulked fractions 5-9, supra, is added to 2.0 grams of the foregoing gel to produce a clear premix. The clear premix is added to 200 grams of CLOROX® with stirring resulting in a clear stable single phase solution. Sufficient 1M aqueous NaOH is added to bring the pH of the mixture up to 12.8. The solution remains substantially stable at 120° F. for a period for seven days. When the 5% aqueous sodium hypochlorite solution is used as a laundry bleach, the resulting laundry on dry-out in an atmosphere of 65% relative humidity yields substantially no characteristic "hypochlorite" odor but does have a fruity, green, chamomile and rose aroma. Furthermore, no such characteristic "hypochlorite" aroma is retained on the hands of the individual handling such laundry in both the wet and the dry states.

EXAMPLE LV

A mixture is prepared consisting of 10 grams of DOWFAX® 2A1 and 10 grams of DOWFAX® 3B1 (60.75); and 2.0 grams of sodium laurate (7.00%); and 20.0 grams of water (32.25%). The mixture is heated while stirring followed by ultrasonic dispersion thereby yielding a homogeneous gel. 64.2 Grams of this material is used as follows: 4 drops of the compound having the structure:

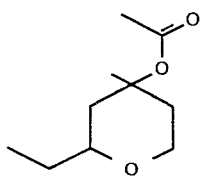

prepared according to Example I, bulked fractions 5-9, supra, is added to 2.0 grams of the foregoing gel to produce a clear premix. The clear premix is added to 200 grams of CLOROX ® with stirring resulting in a clear stable single phase solution. Sufficient 1M aqueous NaOH is added to bring the pH of the mixture up to 12.8. The solution remains substantially stable at 120° F. for a period of seven days. When the 5% aqueous sodium hypochlorite solution is used as a laundry bleach, the resulting laundry on dry-out in an atmosphere of 65% relative humidity yields substantially no characteristic "hypochlorite" odor but does have a fruity, green, chamomile and rose aroma. Furthermore, no such characteristic "hypochlorite" aroma is retained on the hands of the individual handling such laundry in both the wet and the dry states.

EXAMPLE LVI

A mixture is prepared consisting of 60 grams of AROMOX® DMMC-W, 30 grams DOWFAX® 2A1; 6.0 grams lauric acid; 9.0 grams KOH; and 500 grams water. The mixture is heated while stirring followed by ultrasonic dispersion thereby yielding a homogeneous gel. 64.2 Grams of this material is used as follows: 4 drops of the compound having the structure:

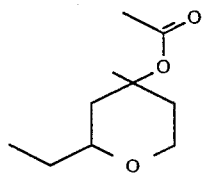

prepared according to Example I, bulked fractions 5-9 is added to 2.0 grams of the foregoing gel to produce a clear premix. The clear premix is added to 200 grams of CLOROX ® with stirring resulting in a clear stable single phase solution. Sufficient 1M aqueous NaOH is added to bring the pH of the mixture up to 12.8. The solution means substantially stable at 120° F. or a period of seven days. When the 5% aqueous sodium hypochlorite solution is used as a laundry bleach, the resulting laundry on dry-out in an atmosphere of 65% relative humidity yields substantially no characteristic "hypochlorite" odor but does have a fruity, green, chamomile and rose aroma. Furthermore, no such characteristic "hypochlorite" aroma is retained on the hands of the individual handling such laundry in both the wet and the dry states.

It is noteworthy that the viscosity of the solution subsequent to heating is 26.75 centipoises.

EXAMPLE LVII

A mixture is prepared consisting of 60 grams of AROMOX® DMMC-W, 21 grams of DOWFAX® 2A1; 3.6 grams of lauric acid; 10.5 grams of KOH and 508 grams of water. The mixture is heated while stirring followed by ultrasonic dispersion thereby yielding a homogeneous gel having a viscosity of 23.45 centipoises. 64.2 Grams of this material is used as follows: 4 drops of a 50:50 mixture of (a) one of the diisoamylene epoxide mixtures produced according to Example II of application for U.S. Letters Patent, Ser. No. 277,131 filed on June 25, 1981 and (b) the compound having the structure:

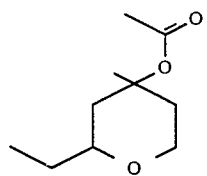

prepared according to Example I, bulked fractions 5-9, supra, is added to 2.0 grams of the foregoing gel to produce a clear premix. The clear premix is added to 200 grams of CLOROX ® with stirring resulting in a clear stable single phase solution. Sufficient 1M aqueous NaOH is added to bring the pH of the mixture up to 12.8. The solution remains substantially stable at 120° F. for a period of seven days. When the 5% aqueous sodium hypochlorite solution is used as a laundry bleach, the resulting laundry on dry-out in an atmosphere of 65% relative humidity yields substantially no characteristic "hypochlorite" odor but does have a fruity, green, chamomile and rose aroma with stemmy nuances. Furthermore, no such characteristic "hypochlorite" aroma is retained on the hands of the individual handling such laundry in both the wet and the dry states.

What is claimed is:

1. A 2,4,4-trisubstituted tetrahydro pyranyl ester defined according to the structure:

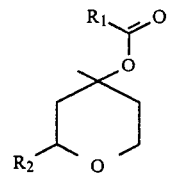

wherein $R_1$ represents methyl or ethyl and $R_2$ represents $C_2$-$C_4$ straight chain or branched chain alkyl or alkenyl.

2. The compound of claim 1 having the structure:

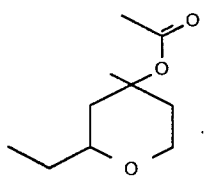

3. The compound of claim 1 having the structure:

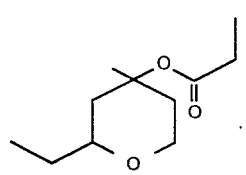

4. The compound of claim 1 having the structure:

5. The compound of claim 1 having the structure:

6. The compound of claim 1 having the structure:

7. The compound of claim 1 having the structure:

8. The compound of claim 1 having the structure:

9. The compound of claim 1 having the structure:

10. The compound of claim 1 having the structure:

11. The compound of claim 1 having the structure:

12. The compound of claim 1 having the structure:

13. The compound of claim 1 having the structure:

14. A process for augmenting or enhancing the aroma of a consumable material selected from the group consisting of perfume compositions, perfumed articles and perfumed polymers comprising the step of intimately admixing with said consumable material, an aroma augmenting or enhancing quantity of at least one compound defined according to claim 1.

15. A process for augmenting or enhancing the aroma of a consumable material selected from the group consisting of perfume compositions, perfumed articles and perfumed polymers comprising the step of intimately admixing with said consumable material, an aroma augmenting or enhancing quantity of at least one compound defined according to claim 2.

16. A process for augmenting or enhancing the aroma of a consumable material selected from the group consisting of perfume compositions, perfumed articles and perfumed polymers comprising the step of intimately admixing with said consumable material, an aroma augmenting or enhancing quantity of at least one compound defined according to claim 3.

17. A process for augmenting or enhancing the aroma of a consumable material selected from the group consisting of perfume compositions, perfumed articles and perfumed polymers comprising the step of intimately admixing with said consumable material, an aroma augmenting or enhancing quantity of at least one compound defined according to claim 4.

18. A process for augmenting or enhancing the aroma of a consumable material selected from the group consisting of perfume compositions, perfumed articles and perfumed polymers comprising the step of intimately admixing with said consumable material, an aroma augmenting or enhancing quantity of at least one compound defined according to claim 5.

19. A process for augmenting or enhancing the aroma of a consumable material selected from the group consisting of perfume compositions, perfumed articles and perfumed polymers comprising the step of intimately admixing with said consumable material, an aroma augmenting or enhancing quantity of at least one compound defined according to claim 6.

20. A process for augmenting or enhancing the aroma of a consumable material selected from the group consisting of perfume compositions, perfumed articles and perfumed polymers comprising the step of intimately admixing with said consumable material, an aroma augmenting or enhancing quantity of at least one compound defined according to claim 7.

21. A process for augmenting or enhancing the aroma of a consumable material selected from the group consisting of perfume compositions, perfumed articles and perfumed polymers comprising the step of intimately admixing with said consumable material, an aroma augmenting or enhancing quantity of at least one compound defined according to claim 8.

22. A process for augmenting or enhancing the aroma of a consumable material selected from the group consisting of perfume compositions, perfumed articles and perfumed polymers comprising the step of intimately admixing with said consumable material, an aroma augmenting or enhancing quantity of at least one compound defined according to claim 9.

23. A process for augmenting or enhancing the aroma of a consumable material selected form the group consisting of perfume compositions, perfumed articles and perfumed polymers comprising the step of intimately admixing with said consumable material, an aroma augmenting or enhancing quantity of at least one compound defined according to claim 10.

24. A process for augmenting or enhancing the aroma of a consumable material selected from the group consisting of perfume compositions, perfumed articles and perfumed polymers comprising the step of intimately admixing with said consumable material, an aroma augmenting or enhancing quantity of at least one compound defined according to claim 11.

25. A process for augmenting or enhancing the aroma of a consumable material selected from the group consisting of perfume compositions, perfumed articles and perfumed polymers comprising the step of intimately admixing with said consumable material, an aroma augmenting or enhancing quantity of at least one compound defined according to claim 12.

26. A process for augmenting of enhancing the aroma of a consumable material selected from the group consisting of perfume compositions, perfumed articles and perfumed polymers comprising the step of intimately admixing with said consumable material, an aroma augmenting or enhancing quantity of at least one compound defined according to claim 13.

27. A chlorine-containing bleach composition comprising:
(a) a chlorine bleach base; and
(b) intimately admixed therewith at least one compound defined according to claim 1.

28. A process for producing a stable single phase aqueous alkaline metal hypochlorite solution having a pleasant fragrance consisting, in sequential order, of the steps of (a) adjusting the pH of an aqueous alkali metal hypochlorite solution to the range of 11–14.0; (b) admixing a composition of matter selected from the group consisting of (i) a chemical compound having the structure:

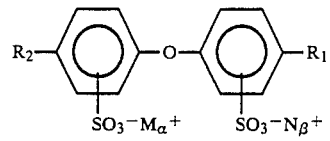

wherein at least one of $R_1$ and $R_2$ is $C_{10}$–$C_{12}$ straight chain or branched chain alkyl and $M_\alpha$ and $M_\beta$ are the same or different and each represents lithium, potassium or sodium; and (ii) a mixture of at least one compound having the structure:

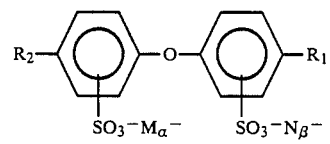

and a compound having the structure:

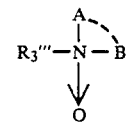

wherein $R_3'''$ is straight chain alkyl; wherein more than 55% of the $R_3'''$ moieties consist of straight chain alkyl having from 11 to 13 carbon atoms and wherein "A" and "B" are each separately methyl or taken together complete a morpholine ring with at least one compound defined according to claim 1 and (c) adding said premix to the pH adjusted hypochlorite solution.

29. A perfumed aqueous alkali metal hypochlorite solution comprising as a sole detergent a composition of matter selected from the group consisting of (1) at least one substance defined according to the structure:

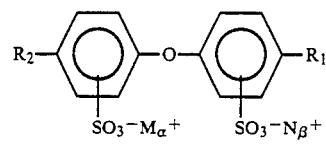

wherein at least one of $R_1$ and $R_2$ is $C_{10}$–$C_{12}$ straight chain or branched chain alkyl; when one of $R_1$ or $R_2$ is $C_{10}$–$C_{12}$ straight chain or branched chain alkyl and the other of $R_1$ or $R_2$ is hydrogen; wherein $M_\alpha$ and $M_\beta$ are the same or different and each represents alkalki metal selected from the group consisting of sodium, potassium and lithium and (2) a mixture comprising a material having the structure:

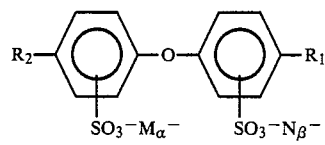

and intimately admixed therewith (i) a substance having the structure:

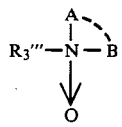

wherein $R_3'''$ is straight chain alkyl, wherein more than 55% of the $R_3'''$ moieties consist of straight chain alkyl having from 11 up to 13 carbon atoms and wherein "A" and "B" are each separately methyl, (ii) up to 0.2% of one or more compatible perfume oils, and (iii) an aroma augmenting or enhancing quantity of at least one compound defined according to claim 1, such hypochlorite solution having a pH of from 11 up to 14.0.

30. The composition of matter of claim 29 which is thickened using a thickening quantity of $C_{10}$–$C_{20}$ alkanoic acid salt thickener in a concentration such that the viscosity of the composition is 20–60 centipoises at a temperature of 20°–40° C.

31. The composition of claim 29 wherein the compound having the structure:

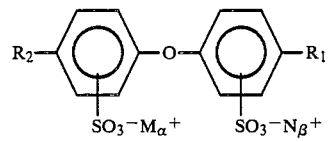

is selected from the group of materials having the structures:

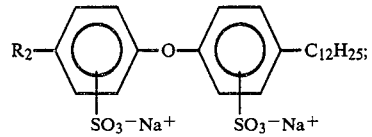

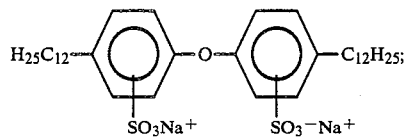

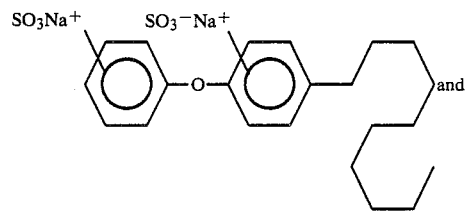

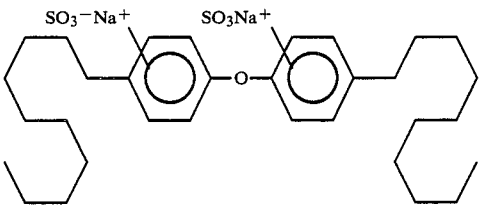

32. The process of claim 35 wherein the composition of matter admixed in step (b) also includes diisoamylene epoxide.

* * * * *